US012649774B2

(12) United States Patent
He et al.

(10) Patent No.: US 12,649,774 B2
(45) Date of Patent: Jun. 9, 2026

(54) CAR-T CELL COMPOSITIONS, METHODS OF USE THEREOF

(71) Applicant: AUGUSTA UNIVERSITY RESEARCH INSTITUTE, INC., Augusta, GA (US)

(72) Inventors: Yukai He, Martinez, GA (US); Leidy D. Caraballo Galva, Augusta, GA (US); Xiaotao Jiang, Augusta, GA (US)

(73) Assignee: AUGUSTA UNIVERSITY RESEARCH INSTITUTE, INC., Augusta, GA (US)

( * ) Notice: Subject to any disclaimer, the term of this patent is extended or adjusted under 35 U.S.C. 154(b) by 963 days.

(21) Appl. No.: 17/762,186

(22) PCT Filed: Sep. 21, 2020

(86) PCT No.: PCT/US2020/051798
§ 371 (c)(1),
(2) Date: Mar. 21, 2022

(87) PCT Pub. No.: WO2021/055942
PCT Pub. Date: Mar. 25, 2021

(65) Prior Publication Data
US 2022/0288124 A1 Sep. 15, 2022

Related U.S. Application Data

(60) Provisional application No. 62/903,776, filed on Sep. 21, 2019.

(51) Int. Cl.
| | |
|---|---|
| *C07K 14/725* | (2006.01) |
| *A61K 40/11* | (2025.01) |
| *A61K 40/31* | (2025.01) |
| *A61K 40/42* | (2025.01) |
| *A61P 35/00* | (2006.01) |
| *C07K 14/705* | (2006.01) |
| *C07K 16/30* | (2006.01) |
| *C12N 5/0783* | (2010.01) |

(52) U.S. Cl.
CPC .......... *C07K 14/7051* (2013.01); *A61K 40/11* (2025.01); *A61K 40/31* (2025.01); *A61K 40/4261* (2025.01); *A61P 35/00* (2018.01); *C07K 16/303* (2013.01); *C12N 5/0636* (2013.01); *A61K 2239/38* (2023.05); *A61K 2239/53* (2023.05); *C07K 2317/34* (2013.01); *C07K 2317/92* (2013.01); *C07K 2319/33* (2013.01)

(58) Field of Classification Search
CPC .................................................. C07K 14/7051
See application file for complete search history.

(56) References Cited

U.S. PATENT DOCUMENTS

2014/0170114 A1* 6/2014 Kaplan .................. C07K 16/18
530/387.5

OTHER PUBLICATIONS

International Search Report dated Nov. 26, 2020 for PCT/US2020/051798, pp. 1-3.
Written Opinion dated Nov. 26, 2020 for PCT/US2020/051798, pp. 1-3.

* cited by examiner

*Primary Examiner* — Christopher M Babic
*Assistant Examiner* — Hanan Isam Abuzeineh
(74) *Attorney, Agent, or Firm* — PABST PATENT GROUP LLP

(57) ABSTRACT

Chimeric antigen receptor T cell (CARTs) compositions and methods of their use are provided. One embodiment provides a chimeric antigen receptor T cell composition including 8F8 chimeric antigen receptor T cells. Another embodiment provides a chimeric antigen receptor T cell composition including 6G11 chimeric antigen receptor T cells. Still another embodiment provide a chimeric antigen receptor T cell composition including 12D7 chimeric antigen receptor T cells. The disclosed CARTs can be used to treat cancer, for example hepatocellular carcinoma.

20 Claims, 53 Drawing Sheets

Specification includes a Sequence Listing.

| mAbs | 2D7 | 2H7 | 3H1 | 3H4 | 4C1 | 5D5 | 5G10 | 6D6 | 6B12 | 6G11 | 7E5 | 7G11 | 8C8 | 8F8 | 10C6 | 11A3 | 11E2 | 11G11 | 12D7 | 12E6 | 12F1 | 13A6 |
|---|---|---|---|---|---|---|---|---|---|---|---|---|---|---|---|---|---|---|---|---|---|---|
| Ig Class | M | G1 | G1 | M | G1 | G2a | M | G1 | M | M | A | G2b | G2a | G2a | M | G1 | G2b | G2b | M | M | G1 | G1 |
| L-Chain | K | K | K | K | K | K | K | K | K | K | K | K | K | K | K | K | K | K | K | K | K | K |
| HepG2 | +++ | ++ | - | +++ | - | +++ | +++ | - | +++ | +++ | - | +/- | ++ | +++ | +++ | - | +++ | ++ | +++ | +++ | - | - |
| N/C | N | N | - | N | - | C | N | - | N | N | - | - | C | C | N | - | N | N | N | N | - | - |

FIG. 1A

HepG2   6G11   8C8   8F8   12D7   12E6

FIG. 1B hGPC3-N — EF1α p — [ 1-358 ]

hGPC3-C — EF1α p — [ 359-580 ]

FIG. 1C

| | Liver Tissues | | | Immunoscores on the positive tumor tissuses |
|---|---|---|---|---|
| mAbs | Healthy | ANL | HCC | |
| 6G11 | 0/6 | 0/6 | 3/6 | 3, 3, 4 |
| 8C8 | 6/6 | 6/6 | 6/6 | |
| 8F8 | 0/6 | 0/8 | 5/8 | 5, 3, 5, 5, 3 |
| 12D7 | 0/6 | 0/6 | 3/5 | 4, 3, 3 |
| 12E6 | 3/6 | 3/6 | 4/6 | |

| Ab | KD (M) | KD Error | kon(1/Ms) | kon Error | kdis(1/s) | kdis Error | R^2 |
|---|---|---|---|---|---|---|---|
| 6G11 | 7.43E-09 | 8.68E-11 | 5.24E+04 | 4.12E+02 | 3.89E-04 | 3.37E-06 | 0.9939 |
| 12D7 | 9.76E-09 | 9.61E-11 | 4.15E+04 | 2.81E+02 | 4.05E-04 | 2.89E-06 | 0.9958 |
| 8F8 | 2.29E-08 | 2.90E-10 | 8.97E+03 | 8.02E+01 | 2.06E-04 | 1.83E-06 | 0.9993 |

FIG. 3D CONTINUED

Days after adoptive transfer mAb 6G11-VL (SEQ ID NOS 4 and 5, respectively, in order of appearance)

Original Sq of 6G11_VL+part of C (465 bp)

mAb 6G11-VH (SEQ ID NOS 6 and 7, respectively, in order of appearance)

Original Sq of 6G11_VH+part of C (507 bp)

mAb 8F8-VL (SEQ ID NOS 8 and 9, respectively, in order of appearance)

Original Sq of 8F8-VL+part of C (450 bp)

mAb 8F8-VH (SEQ ID NOS 10 and 11, respectively, in order of appearance)

Original Sq of 8F8-VH+part of C (420 bp)

mAb 12D7-VL (SEQ ID NOS 12 and 13, respectively, in order of appearance)

Original Sq of 12D7-VL+part of C (671 bp)

mAb 12D7-VH (SEQ ID NOS 14 and 15, respectively, in order of appearance)

Original Sq of 12D7-VH+part of C (510 bp)

Recombinant mAb 6G11 amino acid sequences (SEQ ID NOS 16 and 17, respectively, in order of appearance)

Recombinant mAb 6G11-H chain

Recombinant mAb 6G11-L chain

Recombinant mAb 8F8 amino acid sequences (SEQ ID NOS 18 and 19, respectively, in order of appearance)

Recombinant mAb 12D7 amino acid sequences (SEQ ID NOS 20 and 21, respectively, in order of appearance)

12D-H chain

12D7-L chain

6G11-CAR (SEQ ID NOS 1 and 22, respectively, in order of appearance)

FIG. 13A

8F8-CAR (SEQ ID NOS 2 and 23, respectively, in order of appearance)

12D7-CAR sequences (SEQ ID NOS 3 and 24, respectively, in order of appearance)

FIG. 13C

SEQUENCE LISTING

```
<160> NUMBER OF SEQ ID NOS: 31

<210> SEQ ID NO 1
<211> LENGTH: 1470
<212> TYPE: DNA
<213> ORGANISM: Artificial Sequence
<220> FEATURE:
<223> OTHER INFORMATION: Description of Artificial Sequence: Synthetic
```

-continued

```
         polynucleotide

<400> SEQUENCE: 1
atggctctgc cagtgacagc tctgctgctg cctctggctc tgctgctgca cgcagctagg      60
cccgacatcc agatgaacca gagcccttct tctctgagcg cctctctggg agacaccatc     120
accatcactt gccacgcctc ccagaacatc aacgtctggc tgtcttggta ccagcagaaa     180
cccggcaaca tccccaagct gctgatctac aaggccagca acctgcacac cggagtgcct     240
agcagattca gcggcagcgg aagcggaacc ggctttaccc tgaccatcag cagcctgcag     300
cccgaggaca tcgccaccta ctattgccag cagggccagt cttacccttg acattcggc      360 ggaggcacca agctggagat caagagaggc ggaggaggaa gcggaggagg aggatcagga     420
ggaggaggat ctcaggtgca gctgcagcag ccaggatcag aactcgtgag acccggagct     480
agcgtgaagc tgtcttgcaa ggccagcggc tacaccttca cctcttgttg gatgcattgg     540
gtgaagcaga accaggacac gggcctggag tggattggca acatctaccc cggctacggc     600
aacaccaact acgacgagaa gttcaagaac aaggccaccc tgaccgtgga cacctctagc     660
agcaccgcct acatgcagct gagcggactg acaagcgagg atagcgccgt gtactattgc     720
accaggggca gctacctgta cgccatggac tattggggcc agggaaccag cgtgacagtg     780
tctagcacca ccacaccagc ccctagacct cctacaccag cccctacaat cgcctctcag     840
cctctgagcc tgacaccga gcttgtaga ccagccgcag gaggagctgt gcataccagg      900
ggcctggact cgcttgcga ctttttgggtg ctggtggtcg tgggaggagt gctggcttgt     960
tacagcctgc tggtgaccgt ggctttcatc atcttttggg tcaagagggg ccggaagaag    1020
ctgctgtaca tcttcaagca gcccttcatg aggcccgtgc agacaacaca ggaggaggac    1080
ggctgttctt gcaggttccc agaggaagaa gagggcggtt gcgagctgag agtgaagttc    1140
agcagaagcg ccgacgctcc agcttatcag cagggccaga accagctgta caacgagctg    1200
aacctgggca ggaggaggaa atacgacgtg ctggacaagc ggagaggcag agatccagag    1260
atgggcggca gcctcagag aaggaagaac ccccaggagg gcctgtacaa cgagctgcag    1320
aaggacaaga tggccgaggc ttacagcgag atcggcatga aggcgagag gagaagaggc     1380 aagggccacg acggactgta ccagggactg agcacagcca ccaaggatac ctacgacgcc    1440
ctgcatatgc aggctctgcc tcccaggtaa                                    1470

<210> SEQ ID NO 2
<211> LENGTH: 1482
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
atggctctgc cagtgacagc tctgctgctg cctctggctc tgctgctgca cgcagctaga      60
cctgacgtcg tgatgacaca gaccccctctg accctgagcg tgacaatcgg acagccagct     120
agcatcagct gcaagagcag ccagtccctc ctggacagcg acggcgagac ctacctgaat     180
tggctgctgc agagaccagg acagtctcct aagcggctga tctacctggt gtccaagctg     240
gacagcggcg tgccagatag attcacaggc agcggaagcg gcaccgattt caccctgaag     300
atcagcagag tggaggccga ggatctggga gtctactact gttggcaggg cacccacttc     360
cctctgacat ttggagccgg caccaagctg gagctgaaaa gaggcggagg aggaagcgga     420
```

```
ggaggaggaa gcggaggagg aggaagcgaa gtgaagctgg tggagagcgg aggagatctg     480
gtgaagccag gcggaagcct gaagctgtct tgcgccgcca gcggcttcac cttcagcaga     540
tacggactgt cttgggtccg gcagacacca gagaagcgac tcgagtgggt ggctaccatc     600
agcggaagcg gcagctacac ctactaccca gacagcgtga agggcaggtt caccatcagc     660
cgggacaacg ccaagaacaa cctgtacctg cagatgagca gcctgagaag cgaggacacc     720
gctctgtact attgcgtgcg cagaggcacc tacggctacg acaattgggg ccagggaacc     780
accctgacag tgtctagcac caccacccca gctcctagac ctcctacacc agcccctaca     840
atcgcctctc agcctctgag cctgagacct gaagcttgta gaccagccgc aggaggagct     900
gtgcatacca ggggcctgga cttcgcttgc gacttttggg tgctggtggt cgtgggagga     960
gtgctggctt gttacagcct gctggtgacc gtggctttca tcatcttttg ggtcaagagg    1020
ggccggaaga agctgctgta catcttcaag cagcccttca tgaggcccgt gcagacaaca    1080
caggaggagg acggctgttc ttgcaggttc ccagaggaag aagagggcgg ttgcgagctg    1140
agagtgaagt tcagcagaag cgccgacgct ccagcttatc agcagggcca gaaccagctg    1200
tacaacgagc tgaacctggg caggagggag gaatacgacg tgctggacaa gcggagaggc    1260
agagatccag atgggcggg caagcctcag agaaggaaga accccagga gggcctgtac    1320 aacgagctgc agaaggacaa gatggccgag gcttacagcg agatcggcat gaagggcgag    1380
aggagaagag gcaagggcca cgacggactg taccaggac tgagcacagc caccaaggat    1440
acctacgacg ccctgcatat gcaggctctg cctcccaggt aa                       1482
```

```
<210> SEQ ID NO 3
<211> LENGTH: 1470
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
```

```
atggctctgc cagtgacagc tctgctgctg cctctggctc tgctgctgca cgcagctaga      60
cccgacatcg tgatgaccca gagccagaag ttcatgagca ccagcgtggg ggacagagtg     120
tccgtgactt gcaaggccag ccagaacgtg ggaaccaacg tggcttggta ccagcagaag     180
ccaggacaga gccctaaggc cctgatctac agcgccagct acagatacag cggagtgcca     240
gacagattca ccggcagcgg aagcggcaca gacttcaccc tgaccatcag caacgtgcag     300
agcgaggacc tggccgagta cttttgccag cagtacaaca gctaccccct gaccttcgga     360
gccggaacca gctggagct gaagagagga ggaggaggaa gcggaggagg aggaagcgga     420
ggaggaggat ctcaggtgca gctgcagcag ccaggatcag aactcgtgag accaggagcc     480
agcgtgaagc tgtcttgcaa ggctagcggc tacaccttca ccagctactg gatgcattgg     540
gtgaagcaga ctgggacag gggactggag tggatcggca acatctaccc aggcagcgga     600
agcaccaact acgacgagaa gttcaagagc aagggcaccc tgacagtgga cacctctagc     660
agcaccgcct acatgcacct gagctctctg accagcgagg acagcgccgt gtactattgc     720 accagggcg actacgattg ggtgttcgct tattggggcc agggcacact ggtgacagtg     780
agcgccacaa caacaccagc ccctagacct cctacaccag cccctacaat cgcctctcag     840
cctctgagcc tgaggccaga agcttgcaga ccagccgcag gaggagctgt gcataccagg     900
ggcctggact tcgcttgcga cttttgggtg ctggtggtcg tgggaggagt gctggcttgt     960
```

-continued

```
tacagcctgc tggtgaccgt ggctttcatc atcttttggg tcaagagggg ccggaagaag    1020
ctgctgtaca tcttcaagca gcccttcatg aggcccgtgc agacaacaca ggaggaggac    1080
ggctgttctt gcaggttccc agaggaagaa gagggcggtt gcgagctgag agtgaagttc    1140
agcagaagcg ccgacgctcc agcttatcag caggggccaga accagctgta caacgagctg    1200
aacctgggca ggagggagga atacgacgtg ctggacaagc ggagaggcag agatccagag    1260
atgggcggca agcctcagag aaggaagaac ccccaggagg gcctgtacaa cgagctgcag    1320
aaggacaaga tggccgaggc ttacagcgag atcggcatga agggcgagag gagaagaggc    1380
aagggccacg acggactgta ccagggactg agcacagcca ccaaggatac ctacgacgcc    1440
ctgcatatgc aggctctgcc tcccaggtaa                                     1470
```

<210> SEQ ID NO 4
<211> LENGTH: 465
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
atgagggtcc ttgctgagct cctggggctg ctgctgttct gcttttttagg tgtgagatgt     60 gacatccaga tgaaccagtc tccatccagt ctgtctgcat cccttggaga cacaattacc    120
atcacttgcc atgccagtca gaacattaat gtttggttaa gctggtacca gcagaaacca    180
ggaaatattc ctaaactatt gatctataag gcttccaact tgcacacagg cgtcccatca    240
agatttagtg gcagtggatc tggaacaggt ttcacattaa ccatcagcag cctgcagcct    300
gaagacattg ccacttacta ctgtcaacag ggtcaaagtt atccgtggac gttcggtgga    360
ggcaccaagc tggaaatcaa acgggctgat gctgcaccaa ctgtatccat cttcccacca    420
tccagtgagc agttaacatc tggaggtgcc tcagtcgtgt gcttc                    465
```

<210> SEQ ID NO 5
<211> LENGTH: 155
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

```
Met Arg Val Leu Ala Glu Leu Leu Gly Leu Leu Leu Phe Cys Phe Leu
1               5                   10                  15

Gly Val Arg Cys Asp Ile Gln Met Asn Gln Ser Pro Ser Ser Leu Ser
            20                  25                  30

Ala Ser Leu Gly Asp Thr Ile Thr Ile Thr Cys His Ala Ser Gln Asn
        35                  40                  45

Ile Asn Val Trp Leu Ser Trp Tyr Gln Gln Lys Pro Gly Asn Ile Pro
    50                  55                  60

Lys Leu Leu Ile Tyr Lys Ala Ser Asn Leu His Thr Gly Val Pro Ser
65                  70                  75                  80

Arg Phe Ser Gly Ser Gly Ser Gly Thr Gly Phe Thr Leu Thr Ile Ser
                85                  90                  95

Ser Leu Gln Pro Glu Asp Ile Ala Thr Tyr Tyr Cys Gln Gln Gly Gln
            100                 105                 110

Ser Tyr Pro Trp Thr Phe Gly Gly Gly Thr Lys Leu Glu Ile Lys Arg
            115                 120                 125
```

-continued

```
Ala Asp Ala Ala Pro Thr Val Ser Ile Phe Pro Pro Ser Ser Glu Gln
    130                 135                 140

Leu Thr Ser Gly Gly Ala Ser Val Val Cys Phe
145                 150                 155

<210> SEQ ID NO 6
<211> LENGTH: 507
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
atgggatgga gctctatcat cctcttcttg gtagcaacag cctcaggtgt ccactcccag      60
gtccaactgc agcaacctgg gtctgagctg gtgaggcctg gagcttcagt gaagctgtcc     120
tgcaaggctt ctggctacac tttcaccagc tgctggatgc actgggtgaa gcagaggcct     180
ggacaaggcc ttgagtggat tggaaatatt tatcctggtt atggtaatac taactacgat     240
gagaagttca gaacaaggc cacactgact gtagacacat cctccagcac tgcctacatg     300
cagctcagcg gcctgacatc tgaggactct gcggtctatt attgtacaag aggatcgtat     360
ctctatgcta tggactactg gggtcaagga acctcagtca ccgtctcctc agagagtcag     420
tccttcccaa atgtcttccc cctcgtctcc tgcgagagcc ccctgtctga taagaatctg     480
gtggccatgg gctgcctggc ccgggac                                          507

<210> SEQ ID NO 7
<211> LENGTH: 169
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Gly Trp Ser Ser Ile Ile Leu Phe Leu Val Ala Thr Ala Ser Gly
1               5                  10                  15

Val His Ser Gln Val Gln Leu Gln Gln Pro Gly Ser Glu Leu Val Arg
                20                  25                  30

Pro Gly Ala Ser Val Lys Leu Ser Cys Lys Ala Ser Gly Tyr Thr Phe
            35                  40                  45

Thr Ser Cys Trp Met His Trp Val Lys Gln Arg Pro Gly Gln Gly Leu
        50                  55                  60

Glu Trp Ile Gly Asn Ile Tyr Pro Gly Tyr Gly Asn Thr Asn Tyr Asp
65                  70                  75                  80

Glu Lys Phe Lys Asn Lys Ala Thr Leu Thr Val Asp Thr Ser Ser Ser
                85                  90                  95

Thr Ala Tyr Met Gln Leu Ser Gly Leu Thr Ser Glu Asp Ser Ala Val
            100                 105                 110

Tyr Tyr Cys Thr Arg Gly Ser Tyr Leu Tyr Ala Met Asp Tyr Trp Gly
        115                 120                 125

Gln Gly Thr Ser Val Thr Val Ser Ser Glu Ser Gln Ser Phe Pro Asn
    130                 135                 140

Val Phe Pro Leu Val Ser Cys Glu Ser Pro Leu Ser Asp Lys Asn Leu
145                 150                 155                 160

Val Ala Met Gly Cys Leu Ala Arg Asp
                165
```

-continued

```
<210> SEQ ID NO 8
<211> LENGTH: 450
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
atgagtcctg cccagttcct gtttctgtta gtgctctgga ttcgggtttc agaaaccaac      60
ggtgatgttg tgatgaccca gactccactc actttgtcgg ttaccattgg acaaccagcc     120
tccatctctt gcaagtcaag tcagagcctc ttagatagtg atggagagac atatttgaat     180
tggttgttac agaggccagg ccagtctcca aagcgcctaa tctatctggt gtctaaactg     240
gactctggag tccctgacag gttcactggc agtggatcag ggacagattt cacactgaaa     300
atcagcagag tggaggctga agatttggga gtttactatt gctggcaagg tacacatttt     360
cctctcacgt tcggtgctgg gaccaagctg gagctgaaac gggctgatgc tgcaccaact     420
gtatccatct tcccaccatc cagtgaatca                                      450

<210> SEQ ID NO 9
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Ser Pro Ala Gln Phe Leu Phe Leu Leu Val Leu Trp Ile Arg Val
1               5                   10                  15

Ser Glu Thr Asn Gly Asp Val Val Met Thr Gln Thr Pro Leu Thr Leu
                20                  25                  30

Ser Val Thr Ile Gly Gln Pro Ala Ser Ile Ser Cys Lys Ser Ser Gln
            35                  40                  45

Ser Leu Leu Asp Ser Asp Gly Glu Thr Tyr Leu Asn Trp Leu Leu Gln
        50                  55                  60

Arg Pro Gly Gln Ser Pro Lys Arg Leu Ile Tyr Leu Val Ser Lys Leu
65                  70                  75                  80

Asp Ser Gly Val Pro Asp Arg Phe Thr Gly Ser Gly Ser Gly Thr Asp
                85                  90                  95

Phe Thr Leu Lys Ile Ser Arg Val Glu Ala Glu Asp Leu Gly Val Tyr
            100                 105                 110

Tyr Cys Trp Gln Gly Thr His Phe Pro Leu Thr Phe Gly Ala Gly Thr
        115                 120                 125

Lys Leu Glu Leu Lys Arg Ala Asp Ala Ala Pro Thr Val Ser Ile Phe
    130                 135                 140

Pro Pro Ser Ser Glu Ser
145                 150

<210> SEQ ID NO 10
<211> LENGTH: 420
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
```

```
atgaacttcg ggctcagctt gattttcctt gtcctaattt taaaaggtgt ccagtgtgaa          60
gtgaagctgg tggagtctgg gggagactta gtgaagcctg gagggtccct gaaactctcc         120
tgtgcagcct ctggattcac tttcagtagg tatggcctgt cttgggttcg ccagactccg         180
gagaagaggc tggagtgggt cgcaaccatt agtggtagtg gtagttacac ctactatcca         240
gacagtgtga aggggcgatt caccatctcc agagacaatg ccaagaacaa cctgtacctc         300
caaatgagca gtctgaggtc tgaggacacg gccttgtatt actgtgtaag acagagggacg         360 tatggttacg acaactgggg ccaaggcacc actctcacag tctcctcagc caaaacaaca         420
```

```
<210> SEQ ID NO 11
<211> LENGTH: 140
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Asn Phe Gly Leu Ser Leu Ile Phe Leu Val Leu Ile Leu Lys Gly
1               5                   10                  15

Val Gln Cys Glu Val Lys Leu Val Glu Ser Gly Gly Asp Leu Val Lys
            20                  25                  30

Pro Gly Gly Ser Leu Lys Leu Ser Cys Ala Ala Ser Gly Phe Thr Phe
        35                  40                  45

Ser Arg Tyr Gly Leu Ser Trp Val Arg Gln Thr Pro Glu Lys Arg Leu
    50                  55                  60

Glu Trp Val Ala Thr Ile Ser Gly Ser Gly Ser Tyr Thr Tyr Tyr Pro
65                  70                  75                  80

Asp Ser Val Lys Gly Arg Phe Thr Ile Ser Arg Asp Asn Ala Lys Asn
                85                  90                  95

Asn Leu Tyr Leu Gln Met Ser Ser Leu Arg Ser Glu Asp Thr Ala Leu
            100                 105                 110

Tyr Tyr Cys Val Arg Arg Gly Thr Tyr Gly Tyr Asp Asn Trp Gly Gln
        115                 120                 125

Gly Thr Thr Leu Thr Val Ser Ser Ala Lys Thr Thr
    130                 135                 140
```

```
<210> SEQ ID NO 12
<211> LENGTH: 671
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
gaaggcgagt cgcatgctcc ggccgccatg gcggccgcgg gaattcgatt cactgccatc          60
aatcttccac ttgtattttg ggctgttatg ttctctctct ttttaataca tcagatcagc         120
atgggcatca agatggagtc acagactcag gtctttgtat acatgttgct gtggttgtct         180
ggtgttgatg gagacattgt gatgacccag tctcaaaaat tcatgtccac atcagtagga         240
gacagggtca gcgtcacctg caaggccagt cagaatgtgg gtactaatgt agcctggtat         300
caacagaaac cagggcaatc tcctaaagca ctgatttact cggcatccta ccggtacagt         360
ggagtccctg atcgcttcac aggcagtgga tctgggacag atttcactct caccatcagc         420
aatgtgcagt ctgaagactt ggcagagtat ttctgtcagc aatataacag ctatcctctc         480
```

-continued

```
acgttcggtg ctgggaccaa gctggagctg aaacgggctg atgctgcacc aactgtatcc      540
atcttcccac catccagtga gcagttaaca tctggaggtg cctcagtcgt gtgcttcttg      600
aacaacttct accccaaaga catcaatgtc aagtggaaga ttgatggcag tgaatcacta      660
gtgaattcgc g                                                          671
```

<210> SEQ ID NO 13
<211> LENGTH: 179
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Met Glu Ser Gln Thr Gln Val Phe Val Tyr Met Leu Leu Trp Leu Ser
1               5                   10                  15

Gly Val Asp Gly Asp Ile Val Met Thr Gln Ser Gln Lys Phe Met Ser
            20                  25                  30

Thr Ser Val Gly Asp Arg Val Ser Val Thr Cys Lys Ala Ser Gln Asn
        35                  40                  45

Val Gly Thr Asn Val Ala Trp Tyr Gln Gln Lys Pro Gly Gln Ser Pro
    50                  55                  60

Lys Ala Leu Ile Tyr Ser Ala Ser Tyr Arg Tyr Ser Gly Val Pro Asp
65                  70                  75                  80

Arg Phe Thr Gly Ser Gly Ser Gly Thr Asp Phe Thr Leu Thr Ile Ser
            85                  90                  95

Asn Val Gln Ser Glu Asp Leu Ala Glu Tyr Phe Cys Gln Gln Tyr Asn
            100                 105                 110

Ser Tyr Pro Leu Thr Phe Gly Ala Gly Thr Lys Leu Glu Leu Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Ser Leu
                165                 170                 175

Val Asn Ser
```

<210> SEQ ID NO 14
<211> LENGTH: 510
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
gaccggtcct tgactaaggt cattgttctc actacagtta ctgagcacac agacctcacc       60
atgggatgga gctgtatcat cctcttcttg gtagcaacag ctacaggtgt ccactcccag      120
gtccaactgc agcaacctgg gtctgagctg gtgaggcctg gagcttcagt gaagctgtcc      180
tgcaaggctt ctggctacac attcaccagc tactggatgc actgggtgaa gcagaggctt      240
ggacaaggcc ttgagtggat tggaaatatt tatcctggta gtggtagtac taactacgat      300
gagaagttca gagcaagggg cacgctgact gtagacacat cctccagcac agcctacatg      360
cacctcagca gcctgacatc tgaggactct gcggtctatt actgtacaag aggtgattac      420
```

```
gactgggttt ttgcttactg gggccaaggg actctggtca ctgtctctgc agagagtcag      480
tccttcccaa atgtcttccc ccaatcacta                                       510

<210> SEQ ID NO 15
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Gly Trp Ser Cys Ile Ile Leu Phe Leu Val Ala Thr Ala Thr Gly
1               5                   10                  15

Val His Ser Gln Val Gln Leu Gln Gln Pro Gly Ser Glu Leu Val Arg
                20                  25                  30

Pro Gly Ala Ser Val Lys Leu Ser Cys Lys Ala Ser Gly Tyr Thr Phe
            35                  40                  45

Thr Ser Tyr Trp Met His Trp Val Lys Gln Arg Leu Gly Gln Gly Leu
        50                  55                  60

Glu Trp Ile Gly Asn Ile Tyr Pro Gly Ser Gly Ser Thr Asn Tyr Asp
65                  70                  75                  80

Glu Lys Phe Lys Ser Lys Gly Thr Leu Thr Val Asp Thr Ser Ser Ser
                85                  90                  95

Thr Ala Tyr Met His Leu Ser Ser Leu Thr Ser Glu Asp Ser Ala Val
            100                 105                 110

Tyr Tyr Cys Thr Arg Gly Asp Tyr Asp Trp Val Phe Ala Tyr Trp Gly
            115                 120                 125

Gln Gly Thr Leu Val Thr Val Ser Ala Glu Ser Gln Ser Phe Pro Asn
        130                 135                 140

Val Phe Pro Gln Ser Leu
145                 150

<210> SEQ ID NO 16
<211> LENGTH: 464
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Gly Trp Ser Cys Ile Ile Leu Phe Leu Val Ala Thr Ala Thr Gly
1               5                   10                  15

Gln Val Gln Leu Gln Gln Pro Gly Ser Glu Leu Val Arg Pro Gly Ala
                20                  25                  30

Ser Val Lys Leu Ser Cys Lys Ala Ser Gly Tyr Thr Phe Thr Ser Cys
            35                  40                  45

Trp Met His Trp Val Lys Gln Arg Pro Gly Gln Gly Leu Glu Trp Ile
        50                  55                  60

Gly Asn Ile Tyr Pro Gly Tyr Gly Asn Thr Asn Tyr Asp Glu Lys Phe
65                  70                  75                  80

Lys Asn Lys Ala Thr Leu Thr Val Asp Thr Ser Ser Ser Thr Ala Tyr
                85                  90                  95

Met Gln Leu Ser Gly Leu Thr Ser Glu Asp Ser Ala Val Tyr Tyr Cys
            100                 105                 110

Thr Arg Gly Ser Tyr Leu Tyr Ala Met Asp Tyr Trp Gly Gln Gly Thr
```

-continued

```
            115                 120                 125
Ser Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
                180                 185                 190

Ser Ser Gly Leu Tyr Ser Leu Ser Ser Val Val Thr Val Pro Ser Ser
                195                 200                 205

Ser Leu Gly Thr Gln Thr Tyr Ile Cys Asn Val Asn His Lys Pro Ser
    210                 215                 220

Asn Thr Lys Val Asp Lys Arg Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
                260                 265                 270

Thr Pro Glu Val Thr Cys Val Val Val Asp Val Ser His Glu Asp Pro
                275                 280                 285

Glu Val Lys Phe Asn Trp Tyr Val Asp Gly Val Glu Val His Asn Ala
    290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
                340                 345                 350

Ile Ser Lys Ala Lys Gly Gln Pro Arg Glu Pro Gln Val Tyr Thr Leu
                355                 360                 365

Pro Pro Ser Arg Glu Glu Met Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
                420                 425                 430

Arg Trp Gln Gln Gly Asn Val Phe Ser Cys Ser Val Met His Glu Ala
                435                 440                 445

Leu His Asn His Tyr Thr Gln Lys Ser Leu Ser Leu Ser Pro Gly Lys
    450                 455                 460
```

```
<210> SEQ ID NO 17
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Gly Trp Ser Cys Ile Ile Leu Phe Leu Val Ala Thr Ala Thr Gly
1               5                   10                  15
```

-continued

```
Asp Ile Gln Met Asn Gln Ser Pro Ser Ser Leu Ser Ala Ser Leu Gly
            20              25              30

Asp Thr Ile Thr Ile Thr Cys His Ala Ser Gln Asn Ile Asn Val Trp
        35              40              45

Leu Ser Trp Tyr Gln Gln Lys Pro Gly Asn Ile Pro Lys Leu Leu Ile
    50              55              60

Tyr Lys Ala Ser Asn Leu His Thr Gly Val Pro Ser Arg Phe Ser Gly
65              70              75              80

Ser Gly Ser Gly Thr Gly Phe Thr Leu Thr Ile Ser Ser Leu Gln Pro
                85              90              95

Glu Asp Ile Ala Thr Tyr Tyr Cys Gln Gln Gly Gln Ser Tyr Pro Trp
            100             105             110

Thr Phe Gly Gly Gly Thr Lys Leu Glu Ile Lys Arg Arg Thr Val Ala
            115             120             125

Ala Pro Ser Val Phe Ile Phe Pro Pro Ser Asp Glu Gln Leu Lys Ser
    130             135             140

Gly Thr Ala Ser Val Val Cys Leu Leu Asn Asn Phe Tyr Pro Arg Glu
145             150             155             160

Ala Lys Val Gln Trp Lys Val Asp Asn Ala Leu Gln Ser Gly Asn Ser
            165             170             175

Gln Glu Ser Val Thr Glu Gln Asp Ser Lys Asp Ser Thr Tyr Ser Leu
            180             185             190

Ser Ser Thr Leu Thr Leu Ser Lys Ala Asp Tyr Glu Lys His Lys Val
            195             200             205

Tyr Ala Cys Glu Val Thr His Gln Gly Leu Ser Ser Pro Val Thr Lys
    210             215             220

Ser Phe Asn Arg Gly Glu Cys
225             230
```

<210> SEQ ID NO 18
<211> LENGTH: 463
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Met Gly Trp Ser Cys Ile Ile Leu Phe Leu Val Ala Thr Ala Thr Gly
1               5               10              15

Glu Val Lys Leu Val Glu Ser Gly Gly Asp Leu Val Lys Pro Gly Gly
            20              25              30

Ser Leu Lys Leu Ser Cys Ala Ala Ser Gly Phe Thr Phe Ser Arg Tyr
        35              40              45

Gly Leu Ser Trp Val Arg Gln Thr Pro Glu Lys Arg Leu Glu Trp Val
    50              55              60

Ala Thr Ile Ser Gly Ser Gly Ser Tyr Thr Tyr Tyr Pro Asp Ser Val
65              70              75              80

Lys Gly Arg Phe Thr Ile Ser Arg Asp Asn Ala Lys Asn Asn Leu Tyr
            85              90              95

Leu Gln Met Ser Ser Leu Arg Ser Glu Asp Thr Ala Leu Tyr Tyr Cys
            100             105             110

Val Arg Arg Gly Thr Tyr Gly Tyr Asp Asn Trp Gly Gln Gly Thr Thr
            115             120             125

Leu Thr Val Ser Ser Ala Ser Thr Lys Gly Pro Ser Val Phe Pro Leu
    130             135             140
```

Ala Pro Ser Ser Lys Ser Thr Ser Gly Gly Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Ser
        195                 200                 205

Leu Gly Thr Gln Thr Tyr Ile Cys Asn Val Asn His Lys Pro Ser Asn
    210                 215                 220

Thr Lys Val Asp Lys Arg Val Glu Pro Lys Ser Cys Asp Lys Thr His
225                 230                 235                 240

Thr Cys Pro Pro Cys Pro Ala Pro Glu Leu Leu Gly Gly Pro Ser Val
                245                 250                 255

Phe Leu Phe Pro Pro Lys Pro Lys Asp Thr Leu Met Ile Ser Arg Thr
                260                 265                 270

Pro Glu Val Thr Cys Val Val Val Asp Val Ser His Glu Asp Pro Glu
            275                 280                 285

Val Lys Phe Asn Trp Tyr Val Asp Gly Val Glu Val His Asn Ala Lys
    290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
            340                 345                 350

Ser Lys Ala Lys Gly Gln Pro Arg Glu Pro Gln Val Tyr Thr Leu Pro
        355                 360                 365

Pro Ser Arg Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
    450                 455                 460

<210> SEQ ID NO 19
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Gly Trp Ser Cys Ile Ile Leu Phe Leu Val Ala Thr Ala Thr Gly
1               5                   10                  15

Asp Val Val Met Thr Gln Thr Pro Leu Thr Leu Ser Val Thr Ile Gly
                20                  25                  30

Gln Pro Ala Ser Ile Ser Cys Lys Ser Ser Gln Ser Leu Leu Asp Ser

-continued

```
            35                  40                  45

Asp Gly Glu Thr Tyr Leu Asn Trp Leu Leu Gln Arg Pro Gly Gln Ser
    50                  55                  60

Pro Lys Arg Leu Ile Tyr Leu Val Ser Lys Leu Asp Ser Gly Val Pro
65                  70                  75                  80

Asp Arg Phe Thr Gly Ser Gly Ser Gly Thr Asp Phe Thr Leu Lys Ile
                85                  90                  95

Ser Arg Val Glu Ala Glu Asp Leu Gly Val Tyr Tyr Cys Trp Gln Gly
            100                 105                 110

Thr His Phe Pro Leu Thr Phe Gly Ala Gly Thr Lys Leu Glu Leu Lys
            115                 120                 125

Arg Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 20
<211> LENGTH: 464
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Gly Trp Ser Cys Ile Ile Leu Phe Leu Val Ala Thr Ala Thr Gly
1               5                   10                  15

Gln Val Gln Leu Gln Gln Pro Gly Ser Glu Leu Val Arg Pro Gly Ala
            20                  25                  30

Ser Val Lys Leu Ser Cys Lys Ala Ser Gly Tyr Thr Phe Thr Ser Tyr
            35                  40                  45

Trp Met His Trp Val Lys Gln Arg Leu Gly Gln Gly Leu Glu Trp Ile
    50                  55                  60

Gly Asn Ile Tyr Pro Gly Ser Gly Ser Thr Asn Tyr Asp Glu Lys Phe
65                  70                  75                  80

Lys Ser Lys Gly Thr Leu Thr Val Asp Thr Ser Ser Ser Thr Ala Tyr
                85                  90                  95

Met His Leu Ser Ser Leu Thr Ser Glu Asp Ser Ala Val Tyr Tyr Cys
            100                 105                 110

Thr Arg Gly Asp Tyr Asp Trp Val Phe Ala Tyr Trp Gly Gln Gly Thr
            115                 120                 125

Leu Val Thr Val Ser Ala Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160
```

-continued

```
Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
                180                 185                 190

Ser Ser Gly Leu Tyr Ser Leu Ser Ser Val Val Thr Val Pro Ser Ser
                195                 200                 205

Ser Leu Gly Thr Gln Thr Tyr Ile Cys Asn Val Asn His Lys Pro Ser
    210                 215                 220

Asn Thr Lys Val Asp Lys Arg Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
                260                 265                 270

Thr Pro Glu Val Thr Cys Val Val Val Asp Val Ser His Glu Asp Pro
                275                 280                 285

Glu Val Lys Phe Asn Trp Tyr Val Asp Gly Val Glu Val His Asn Ala
    290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
                340                 345                 350

Ile Ser Lys Ala Lys Gly Gln Pro Arg Glu Pro Gln Val Tyr Thr Leu
                355                 360                 365

Pro Pro Ser Arg Glu Glu Met Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
                420                 425                 430

Arg Trp Gln Gln Gly Asn Val Phe Ser Cys Ser Val Met His Glu Ala
                435                 440                 445

Leu His Asn His Tyr Thr Gln Lys Ser Leu Ser Leu Ser Pro Gly Lys
    450                 455                 460
```

```
<210> SEQ ID NO 21
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21
```

```
Met Gly Trp Ser Cys Ile Ile Leu Phe Leu Val Ala Thr Ala Thr Gly
1               5                   10                  15

Asp Ile Val Met Thr Gln Ser Gln Lys Phe Met Ser Thr Ser Val Gly
                20                  25                  30

Asp Arg Val Ser Val Thr Cys Lys Ala Ser Gln Asn Val Gly Thr Asn
            35                  40                  45

Val Ala Trp Tyr Gln Gln Lys Pro Gly Gln Ser Pro Lys Ala Leu Ile
    50                  55                  60
```

-continued

```
Tyr Ser Ala Ser Tyr Arg Tyr Ser Gly Val Pro Asp Arg Phe Thr Gly
65                  70                  75                  80

Ser Gly Ser Gly Thr Asp Phe Thr Leu Thr Ile Ser Asn Val Gln Ser
                85                  90                  95

Glu Asp Leu Ala Glu Tyr Phe Cys Gln Gln Tyr Asn Ser Tyr Pro Leu
            100                 105                 110

Thr Phe Gly Ala Gly Thr Lys Leu Glu Leu Lys Arg Arg Thr Val Ala
            115                 120                 125

Ala Pro Ser Val Phe Ile Phe Pro Pro Ser Asp Glu Gln Leu Lys Ser
        130                 135                 140

Gly Thr Ala Ser Val Val Cys Leu Leu Asn Asn Phe Tyr Pro Arg Glu
145                 150                 155                 160

Ala Lys Val Gln Trp Lys Val Asp Asn Ala Leu Gln Ser Gly Asn Ser
                165                 170                 175

Gln Glu Ser Val Thr Glu Gln Asp Ser Lys Asp Ser Thr Tyr Ser Leu
            180                 185                 190

Ser Ser Thr Leu Thr Leu Ser Lys Ala Asp Tyr Glu Lys His Lys Val
            195                 200                 205

Tyr Ala Cys Glu Val Thr His Gln Gly Leu Ser Ser Pro Val Thr Lys
        210                 215                 220

Ser Phe Asn Arg Gly Glu Cys
225                 230

<210> SEQ ID NO 22
<211> LENGTH: 489
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Ala Leu Pro Val Thr Ala Leu Leu Leu Pro Leu Ala Leu Leu Leu
1               5                   10                  15

His Ala Ala Arg Pro Asp Ile Gln Met Asn Gln Ser Pro Ser Ser Leu
                20                  25                  30

Ser Ala Ser Leu Gly Asp Thr Ile Thr Ile Thr Cys His Ala Ser Gln
            35                  40                  45

Asn Ile Asn Val Trp Leu Ser Trp Tyr Gln Gln Lys Pro Gly Asn Ile
        50                  55                  60

Pro Lys Leu Leu Ile Tyr Lys Ala Ser Asn Leu His Thr Gly Val Pro
65                  70                  75                  80

Ser Arg Phe Ser Gly Ser Gly Ser Gly Thr Gly Phe Thr Leu Thr Ile
                85                  90                  95

Ser Ser Leu Gln Pro Glu Asp Ile Ala Thr Tyr Tyr Cys Gln Gln Gly
            100                 105                 110

Gln Ser Tyr Pro Trp Thr Phe Gly Gly Gly Thr Lys Leu Glu Ile Lys
            115                 120                 125

Arg Gly Gly Gly Gly Ser Gly Gly Gly Gly Ser Gly Gly Gly Gly Ser
        130                 135                 140

Gln Val Gln Leu Gln Gln Pro Gly Ser Glu Leu Val Arg Pro Gly Ala
145                 150                 155                 160

Ser Val Lys Leu Ser Cys Lys Ala Ser Gly Tyr Thr Phe Thr Ser Cys
                165                 170                 175

Trp Met His Trp Val Lys Gln Arg Pro Gly Gln Gly Leu Glu Trp Ile
```

-continued

```
              180             185             190
Gly Asn Ile Tyr Pro Gly Tyr Gly Asn Thr Asn Tyr Asp Glu Lys Phe
        195             200             205

Lys Asn Lys Ala Thr Leu Thr Val Asp Thr Ser Ser Ser Thr Ala Tyr
        210             215             220

Met Gln Leu Ser Gly Leu Thr Ser Glu Asp Ser Ala Val Tyr Tyr Cys
225             230             235             240

Thr Arg Gly Ser Tyr Leu Tyr Ala Met Asp Tyr Trp Gly Gln Gly Thr
            245             250             255

Ser Val Thr Val Ser Ser Thr Thr Thr Pro Ala Pro Arg Pro Pro Thr
            260             265             270

Pro Ala Pro Thr Ile Ala Ser Gln Pro Leu Ser Leu Arg Pro Glu Ala
        275             280             285

Cys Arg Pro Ala Ala Gly Gly Ala Val His Thr Arg Gly Leu Asp Phe
        290             295             300

Ala Cys Asp Phe Trp Val Leu Val Val Val Gly Gly Val Leu Ala Cys
305             310             315             320

Tyr Ser Leu Leu Val Thr Val Ala Phe Ile Ile Phe Trp Val Lys Arg
            325             330             335

Gly Arg Lys Lys Leu Leu Tyr Ile Phe Lys Gln Pro Phe Met Arg Pro
            340             345             350

Val Gln Thr Thr Gln Glu Glu Asp Gly Cys Ser Cys Arg Phe Pro Glu
            355             360             365

Glu Glu Glu Gly Gly Cys Glu Leu Arg Val Lys Phe Ser Arg Ser Ala
        370             375             380

Asp Ala Pro Ala Tyr Gln Gln Gly Gln Asn Gln Leu Tyr Asn Glu Leu
385             390             395             400

Asn Leu Gly Arg Arg Glu Glu Tyr Asp Val Leu Asp Lys Arg Arg Gly
            405             410             415

Arg Asp Pro Glu Met Gly Gly Lys Pro Gln Arg Arg Lys Asn Pro Gln
            420             425             430

Glu Gly Leu Tyr Asn Glu Leu Gln Lys Asp Lys Met Ala Glu Ala Tyr
            435             440             445

Ser Glu Ile Gly Met Lys Gly Glu Arg Arg Arg Gly Lys Gly His Asp
        450             455             460

Gly Leu Tyr Gln Gly Leu Ser Thr Ala Thr Lys Asp Thr Tyr Asp Ala
465             470             475             480

Leu His Met Gln Ala Leu Pro Pro Arg
                485

<210> SEQ ID NO 23
<211> LENGTH: 493
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Ala Leu Pro Val Thr Ala Leu Leu Leu Pro Leu Ala Leu Leu Leu
1               5               10              15

His Ala Ala Arg Pro Asp Val Val Met Thr Gln Thr Pro Leu Thr Leu
            20              25              30

Ser Val Thr Ile Gly Gln Pro Ala Ser Ile Ser Cys Lys Ser Ser Gln
        35              40              45
```

-continued

```
Ser Leu Leu Asp Ser Asp Gly Glu Thr Tyr Leu Asn Trp Leu Leu Gln
    50              55              60

Arg Pro Gly Gln Ser Pro Lys Arg Leu Ile Tyr Leu Val Ser Lys Leu
65              70              75              80

Asp Ser Gly Val Pro Asp Arg Phe Thr Gly Ser Gly Ser Gly Thr Asp
            85              90              95

Phe Thr Leu Lys Ile Ser Arg Val Glu Ala Glu Asp Leu Gly Val Tyr
            100             105             110

Tyr Cys Trp Gln Gly Thr His Phe Pro Leu Thr Phe Gly Ala Gly Thr
        115             120             125

Lys Leu Glu Leu Lys Arg Gly Gly Gly Ser Gly Gly Gly Gly Ser
    130             135             140

Gly Gly Gly Gly Ser Glu Val Lys Leu Val Glu Ser Gly Gly Asp Leu
145             150             155             160

Val Lys Pro Gly Gly Ser Leu Lys Leu Ser Cys Ala Ala Ser Gly Phe
            165             170             175

Thr Phe Ser Arg Tyr Gly Leu Ser Trp Val Arg Gln Thr Pro Glu Lys
        180             185             190

Arg Leu Glu Trp Val Ala Thr Ile Ser Gly Ser Gly Ser Tyr Thr Tyr
        195             200             205

Tyr Pro Asp Ser Val Lys Gly Arg Phe Thr Ile Ser Arg Asp Asn Ala
    210             215             220

Lys Asn Asn Leu Tyr Leu Gln Met Ser Ser Leu Arg Ser Glu Asp Thr
225             230             235             240

Ala Leu Tyr Tyr Cys Val Arg Arg Gly Thr Tyr Gly Tyr Asp Asn Trp
            245             250             255

Gly Gln Gly Thr Thr Leu Thr Val Ser Ser Thr Thr Thr Pro Ala Pro
            260             265             270

Arg Pro Pro Thr Pro Ala Pro Thr Ile Ala Ser Gln Pro Leu Ser Leu
        275             280             285

Arg Pro Glu Ala Cys Arg Pro Ala Ala Gly Gly Ala Val His Thr Arg
    290             295             300

Gly Leu Asp Phe Ala Cys Asp Phe Trp Val Leu Val Val Val Gly Gly
305             310             315             320

Val Leu Ala Cys Tyr Ser Leu Leu Val Thr Val Ala Phe Ile Ile Phe
            325             330             335

Trp Val Lys Arg Gly Arg Lys Lys Leu Leu Tyr Ile Phe Lys Gln Pro
        340             345             350

Phe Met Arg Pro Val Gln Thr Thr Gln Glu Glu Asp Gly Cys Ser Cys
        355             360             365

Arg Phe Pro Glu Glu Glu Glu Gly Gly Cys Glu Leu Arg Val Lys Phe
    370             375             380

Ser Arg Ser Ala Asp Ala Pro Ala Tyr Gln Gln Gly Gln Asn Gln Leu
385             390             395             400

Tyr Asn Glu Leu Asn Leu Gly Arg Arg Glu Glu Tyr Asp Val Leu Asp
            405             410             415

Lys Arg Arg Gly Arg Asp Pro Glu Met Gly Gly Lys Pro Gln Arg Arg
            420             425             430

Lys Asn Pro Gln Glu Gly Leu Tyr Asn Glu Leu Gln Lys Asp Lys Met
        435             440             445

Ala Glu Ala Tyr Ser Glu Ile Gly Met Lys Gly Glu Arg Arg Arg Gly
    450             455             460

Lys Gly His Asp Gly Leu Tyr Gln Gly Leu Ser Thr Ala Thr Lys Asp
```

-continued

```
465                 470                 475                 480
Thr Tyr Asp Ala Leu His Met Gln Ala Leu Pro Pro Arg
                485                 490

<210> SEQ ID NO 24
<211> LENGTH: 489
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Ala Leu Pro Val Thr Ala Leu Leu Leu Pro Leu Ala Leu Leu Leu
1               5                   10                  15

His Ala Ala Arg Pro Asp Ile Val Met Thr Gln Ser Gln Lys Phe Met
                20                  25                  30

Ser Thr Ser Val Gly Asp Arg Val Ser Val Thr Cys Lys Ala Ser Gln
            35                  40                  45

Asn Val Gly Thr Asn Val Ala Trp Tyr Gln Gln Lys Pro Gly Gln Ser
        50                  55                  60

Pro Lys Ala Leu Ile Tyr Ser Ala Ser Tyr Arg Tyr Ser Gly Val Pro
65                  70                  75                  80

Asp Arg Phe Thr Gly Ser Gly Ser Gly Thr Asp Phe Thr Leu Thr Ile
                85                  90                  95

Ser Asn Val Gln Ser Glu Asp Leu Ala Glu Tyr Phe Cys Gln Gln Tyr
            100                 105                 110

Asn Ser Tyr Pro Leu Thr Phe Gly Ala Gly Thr Lys Leu Glu Leu Lys
            115                 120                 125

Arg Gly Gly Gly Gly Ser Gly Gly Gly Gly Ser Gly Gly Gly Gly Ser
        130                 135                 140

Gln Val Gln Leu Gln Gln Pro Gly Ser Glu Leu Val Arg Pro Gly Ala
145                 150                 155                 160

Ser Val Lys Leu Ser Cys Lys Ala Ser Gly Tyr Thr Phe Thr Ser Tyr
                165                 170                 175

Trp Met His Trp Val Lys Gln Arg Leu Gly Gln Gly Leu Glu Trp Ile
            180                 185                 190

Gly Asn Ile Tyr Pro Gly Ser Gly Ser Thr Asn Tyr Asp Glu Lys Phe
            195                 200                 205

Lys Ser Lys Gly Thr Leu Thr Val Asp Thr Ser Ser Ser Thr Ala Tyr
        210                 215                 220

Met His Leu Ser Ser Leu Thr Ser Glu Asp Ser Ala Val Tyr Tyr Cys
225                 230                 235                 240

Thr Arg Gly Asp Tyr Asp Trp Val Phe Ala Tyr Trp Gly Gln Gly Thr
                245                 250                 255

Leu Val Thr Val Ser Ala Thr Thr Thr Pro Ala Pro Arg Pro Pro Thr
                260                 265                 270

Pro Ala Pro Thr Ile Ala Ser Gln Pro Leu Ser Leu Arg Pro Glu Ala
            275                 280                 285

Cys Arg Pro Ala Ala Gly Gly Ala Val His Thr Arg Gly Leu Asp Phe
        290                 295                 300

Ala Cys Asp Phe Trp Val Leu Val Val Val Gly Gly Val Leu Ala Cys
305                 310                 315                 320

Tyr Ser Leu Leu Val Thr Val Ala Phe Ile Ile Phe Trp Val Lys Arg
                325                 330                 335
```

```
Gly Arg Lys Lys Leu Leu Tyr Ile Phe Lys Gln Pro Phe Met Arg Pro
            340                 345                 350

Val Gln Thr Thr Gln Glu Glu Asp Gly Cys Ser Cys Arg Phe Pro Glu
        355                 360                 365

Glu Glu Glu Gly Gly Cys Glu Leu Arg Val Lys Phe Ser Arg Ser Ala
        370                 375                 380

Asp Ala Pro Ala Tyr Gln Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Gln Arg Arg Lys Asn Pro Gln
            420                 425                 430

Glu Gly Leu Tyr Asn Glu Leu Gln Lys Asp Lys Met Ala Glu Ala Tyr
        435                 440                 445

Ser Glu Ile Gly Met Lys Gly Glu Arg Arg Arg Gly Lys Gly His Asp
        450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485
```

```
<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (8)..(9)
<223> OTHER INFORMATION: Inosine
<220> FEATURE:
<221> NAME/KEY: modified_base
<222> LOCATION: (13)..(14)
<223> OTHER INFORMATION: Inosine
<220> FEATURE:
<221> NAME/KEY: modified_base
<222> LOCATION: (18)..(19)
<223> OTHER INFORMATION: Inosine

<400> SEQUENCE: 25
caccgggnng ggnngggnng g                                              21

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cctggatgac ttcagtgttg ttctg                                         25

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
```

-continued

```
cactgccatc aatcttccac ttg                                        23

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gggggaagac atttgggaag g                                          21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cactggatgg tgggaagatg g                                          21

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ggttacagtc actgagctgc tg                                         22

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ggagccagtt gtatctccac ac                                         22
```

CAR-T CELL COMPOSITIONS, METHODS OF USE THEREOF

CROSS-REFERENCE TO RELATED APPLICATION

This application is a national stage application, filed under 35 U.S.C. § 371, of International Patent Application No. PCT/US2020/051798 filed on Sep. 21, 2020, which claims benefit of and priority to U.S. Provisional Patent Application No. 62/903,776 filed on Sep. 21, 2019, which are incorporated herein by reference in their entirety.

STATEMENT REGARDING FEDERALLY SPONSORED RESEARCH

This invention was made with government support under RO1 CA168912 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Sep. 10, 2020, is named 064466_117_SL.txt and is 54,038 bytes in size.

TECHNICAL FIELD OF THE INVENTION

Aspects of the invention are generally directed to immunotherapy; in particular, to antibodies and chimeric antigen receptor T cells and methods of their use.

BACKGROUND OF THE INVENTION

There are annually 850,000 new cases of liver cancers, making it the 6th most common cancer worldwide (1). The majority (80-90%) of liver cancers are hepatocellular carcinoma (HCC). While HCC has leveled off in Asia thanks to HBV vaccination (2), the HCC incidence rate increases significantly in the developed countries due to obesity/diabetes (3, 4). According to Center for Disease Control of the United States, the incidence rate of liver cancer has doubled in the last 2 decades, making it the fastest increasing cancer. Treatment options for liver cancer are limited. Although liver resection is curative, most HCC are diagnosed at later stage, disqualifying them for surgery. In addition, the lack of adjuvant therapies results in ~70% 5 yr recurrence rate (5), which makes liver cancer the 2nd leading cause of cancer death among adult men (1). Thus, novel therapies are urgently needed.

Immunotherapy has a great potential for malignant tumors (6-10). Checkpoint blockade has shown therapeutic effect on HCC (9, 11), but it requires the presence of tumor-infiltrating T cells, which do not always exist (12). One approach to generate tumor-specific T cells is to redirect patient's autologous T cells with specific T cell receptors (TCR) (13, 14). However, the TCR's WIC-restriction limits its applications. An WIC-independent method is to utilize chimeric antigen receptor (CAR) genes to engineer T cells to target tumor surface antigens. A CAR combines the high affinity and specificity of monoclonal antibody (mAb) with TCR signaling that can activate T cells and mediate strong and specific killing of tumor cells independent of MHC (15, 16). T cells engineered with CAR genes (CARTs) have demonstrated strong antitumor effects in treating hematologic cancers (16-18).

CARTs are also being intensively studied for treating solid tumors including HCC (19). Glypican 3 (GPC3) is a member of the heparin sulfate (HS) proteoglycans family that is attached to cell membrane via a glycosylphosphatidylinositol (GPI) anchor (20, 21) and is involved in wnt/β-catenin signaling (22, 23). Approximately 70-80% of HCC tumor cells, but not normal hepatocytes, express GPC3. And its level has been associated with poor patient survival rate (24). Thus, GPC3 might be a great target for HCC immunotherapy (25). Several hGPC3-specific mAbs (GC33, YP7, HN3, and MDX-1414) have been tested for their antitumor effects (26-28). But only GC33 has advanced to clinical trials (29), without significant antitumor benefits (30). Recently, several groups have been investigating the antitumor effects of the GC33 derived CARTs (31-33), and their antitumor benefits remain to be evaluated. At the same time, it is unknown whether CARTs developed from different mAbs, especially those mAbs targeting different regions of hGPC3 will generate different antitumor effects. In addition, although GC33 mAb has been proved safe in clinical trials, a recent study showed that 7 out of 34 non-HCC tumor tissues were stained positive by GC33 (34). Thus, there is a need to generate more CARTs of high specificity and effectiveness for HCC immunotherapy.

One object of the invention provides antibody compositions and methods of their use.

Another object of the invention provides chimeric antigen receptor T-cell compositions and methods of their use.

Still another object of the invention is to provide methods and compositions for treating cancer.

SUMMARY OF THE INVENTION

Chimeric antigen receptor T cell (CARTs) compositions and methods of their use are provided. One embodiment provides a chimeric antigen receptor T cell composition including 8F8 chimeric antigen receptor T cells. Another embodiment provides a chimeric antigen receptor T cell composition including 6G11 chimeric antigen receptor T cells. Still another embodiment provides a chimeric antigen receptor T cell composition including 12D7 chimeric antigen receptor T cells. The disclosed CARTs can be used to treat cancer, for example hepatocellular carcinoma.

Other embodiments are directed to antibodies used to produce the CARTs. One embodiment provides a recombinant monoclonal antibody having a mAb 6G11 variable light chain and a mAb 6G11 variable heavy chain. Another embodiment provides a recombinant monoclonal antibody having mAb 8F8 variable light chain and mAb 8F8 variable heavy chain. Still another embodiment provides a recombinant monoclonal antibody comprising mAb 12D7 variable light chain and mAb 12D7 variable heavy chain.

One embodiment provides a pharmaceutical composition including the disclosed antibodies and or CARTs.

Yet another embodiment provides a method for treating liver cancer by administering to a subject in need thereof an effective amount of 6G11, 8F8, or 12D7 chimeric antigen receptor T cells to treat cancer, for example hepatocellular carcinoma.

One embodiment provides a method for treating hepatocellular carcinoma in a subject in need thereof including the steps of isolating T cells from the subject, transfecting the isolated T cells with a vector containing 6G11-CAR nucleic acid sequences, optionally expanding the transfected cells in cell culture, and administering an effective mount of the transfected cells to the subject to treat hepatocellular carcinoma.

One embodiment provides a method for treating hepatocellular carcinoma in a subject in need thereof including the steps of isolating T cells from the subject, transfecting the isolated T cells with a vector containing 8F8-CAR nucleic acid sequences, optionally expanding the transfected cells in cell culture, and administering an effective mount of the transfected cells to the subject to treat hepatocellular carcinoma.

One embodiment provides a method for treating hepatocellular carcinoma in a subject in need thereof including the steps of isolating T cells from the subject, transfecting the isolated T cells with a vector containing 12D7-CAR nucleic acid sequences, optionally expanding the transfected cells in cell culture, and administering an effective mount of the transfected cells to the subject to treat hepatocellular carcinoma.

One embodiment provides a chimeric antigen receptor immune cell comprising a nucleic acids having 85, 90, 95, 99, or 100% sequence identity to SEQ ID NO:1, 2, or 3.

BRIEF DESCRIPTION OF THE DRAWINGS

FIG. 1A is a table of 22 hGPC3-specific mAbs identified by ELISA assay. Their Ig class, staining of HepG2 cells, and binding of the hGPC3 N- or C-fragment were provided. The mAbs in grey shade did not stain HepG2 cells. FIG. 1B is a panel of micrographs showing representative immunofluorescent stainings of HepG2 tumor cells by 5 mAbs. FIG. 1C is a diagram of plasmids expressing the N- and C-fragments of hGPC3.

FIG. 6A shows representative dot plots of CARTs after HepG2 stimulation. FIG. 6B is graph showing the summary of fold changes of the CAR+ T cells before and after HepG2 stimulation. Statistics was done with student t-test. FIGS. 6C and 6D are line graphs showing cytotoxicity and cytokine production of the CARTs. At Day 20 after transduction (6 days after HepG2 stimulation), the non-stimulated (FIG. 6C) and HepG2 stimulated (FIG. 6D) CARTs were co-cultured with HepG2 cells for 20 hrs. Cytotoxicity and IFNg and IL2 were measured by LDH and ELISA. Data show Mean+/−SD, statistics was done with 2way ANOVA. Experiment was repeated thrice with similar observations. FIG. 6E are graphs showing the 6G11 CARTs killed the hGPC3low Huh7 tumor cells, but not the hGPC3-293T cells. FIG. 6F shows 8F8 CARTs, but not 12D7 CARTs (FIG. 6G) could kill Huh7 tumor cells.

FIG. 7A is a graph showing CARTs were co-cultured with HepG2 or with different concentration of soluble hGPC3 20 hrs and ELISA was conducted to determine the IFNg. FIGS. 7B and 7V are graphs showing CARTs were co-cultured with HepG2 (2:1 ratio) in the presence of different concentrations of hGPC3 protein for 20 hrs. Cytotoxicity was measured by LDH assay and cytokines were evaluated by ELISA. Student t-test was used for statistical analysis. ns: not significant. The experiment was repeated twice with similar observation.

FIG. 8A is an illustration of the experimental scheme. FIG. 8B are line graphs of tumor growth curves in different treatment groups. Each line represents one tumor. FIG. 8C-8E show the analysis of the transferred CARTs. The gating strategy was shown FIG. 8C. Mouse CD45+ cells were used as internal reference. The kinetics of human CD45+ (FIG. 8D) and % of CAR+ T cells (FIG. 8E) in NSG mice were summarized. Each line represents one mouse. The color matched to the tumor size curve in B. (FIG. 8F) Pictures of the tumor bearing mice at 40 days after tumor inoculation (33 days after treatment). This experiment was repeated 5 times with similar observations.

DETAILED DESCRIPTION OF THE INVENTION

I. Definitions

Figure 1D:
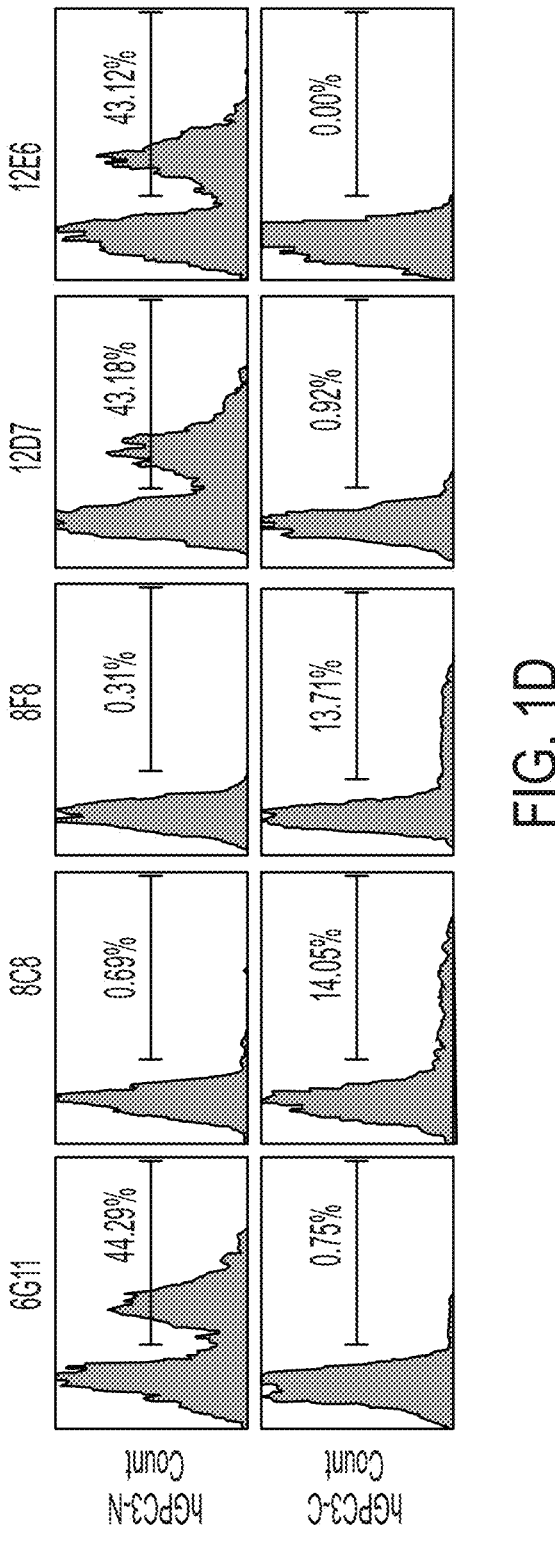
FIG. 1D is a panel of graphs showing 293 cells transfected with either hGPC3-N or hGPC3-C plasmid intracellularly stained with indicated mAbs. The gate was set by the parental 293T cells without transfection.

As used herein, a molecule is said to be able to "immunospecifically bind" a second molecule if such binding exhibits the specificity and affinity of an antibody to its cognate antigen. Antibodies are said to be capable of immunospecifically binding to a target region or conformation ("epitope") of an antigen if such binding involves the antigen recognition site of the immunoglobulin molecule. An antibody that immunospecifically binds to a particular antigen may bind to other antigens with lower affinity if the other antigen has some sequence or conformational similarity that is recognized by the antigen recognition site as determined by, e.g., immunoassays, BIACORE® assays, or other assays known in the art, but would not bind to a totally unrelated antigen. Preferably, however, antibodies (and their antigen binding fragments) will not cross-react with other antigens. Antibodies may also bind to other molecules in a way that is not immunospecific, such as to FcR receptors, by virtue of binding domains in other regions/domains of the molecule that do not involve the antigen recognition site, such as the Fc region.

As used herein, a molecule is said to "physiospecifically bind" a second molecule if such binding exhibits the specificity and affinity of a receptor to its cognate binding ligand. A molecule can be capable of physiospecifically binding to more than one other molecule.

As used herein, the term "antibody" is intended to denote an immunoglobulin molecule that possesses a "variable region" antigen recognition site. The term "variable region" is intended to distinguish such domain of the immunoglobulin from domains that are broadly shared by antibodies (such as an antibody Fc domain). The variable region includes a "hypervariable region" whose residues are responsible for antigen binding. The hypervariable region includes amino acid residues from a "Complementarity Determining Region" or "CDR" (i.e., typically at approximately residues 24-34 (L1), 50-56 (L2) and 89-97 (L3) in the light chain variable domain and at approximately residues 27-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, MD. (1991)) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; CHOTHIA et al., J Mol Biol, 196:901-917 (1987). "Framework Region" or "FR" residues are those variable domain residues other than the hypervariable region residues as herein defined. The term antibody includes monoclonal antibodies, multi-specific antibodies, human antibodies, humanized antibodies, synthetic antibodies, chimeric antibodies, camelized antibodies (See e.g., Muyldermans et al., Trends Biochem Sci, 26:230 (2001); Nuttall et al., Cur Pharm Biotech, 1:253 (2000); Reichmann et al., J Immunol Meth, 231:25 (1999); International Publication Nos. WO 94/04678 and WO 94/25591; U.S. Pat. No. 6,005,079), single-chain Fvs (scFv) (see, e.g., see Pluckthun in The Pharmacology of Monoclonal Antibodies, Vol. 113, Rosenburg and Moore Eds. Springer-Verlag, New York, pp. 269-315 (1994)), single chain antibodies, disulfide-linked Fvs (sdFv), intrabodies, and anti-idiotypic (anti-Id) antibodies (including, e.g., anti-Id and anti-anti-Id antibodies to antibodies). In particular, such antibodies include immunoglobulin molecules of any type (e.g., IgG, IgE, IgM, IgD, IgA and IgY), class (e.g., IgG1, IgG2, IgG3, IgG4, IgA1 and IgA2) or subclass.

As used herein, the term "antigen binding fragment" of an antibody refers to one or more portions of an antibody that contain the antibody's Complementarity Determining Regions ("CDRs") and optionally the framework residues that include the antibody's "variable region" antigen recognition site, and exhibit an ability to immunospecifically bind antigen. Such fragments include Fab', F(ab')2, Fv, single chain (ScFv), and mutants thereof, naturally occurring variants, and fusion proteins including the antibody's "variable region" antigen recognition site and a heterologous protein (e.g., a toxin, an antigen recognition site for a different antigen, an enzyme, a receptor or receptor ligand, etc.).

As used herein, the term "fragment" refers to a peptide or polypeptide including an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues.

As used herein, the terms "treat," "treating," "treatment" and "therapeutic use" refer to the elimination, reduction or amelioration of one or more symptoms of a disease or disorder.

As used herein, a "therapeutically effective amount" refers to that amount of a therapeutic agent sufficient to mediate a clinically relevant elimination, reduction or amelioration of such symptoms. An effect is clinically relevant if its magnitude is sufficient to impact the health or prognosis of a recipient subject. A therapeutically effective amount may refer to the amount of therapeutic agent sufficient to delay or minimize the onset of disease, e.g., delay or minimize the spread of cancer. A therapeutically effective amount may also refer to the amount of the therapeutic agent that provides a therapeutic benefit in the treatment or management of a disease.

As used herein, an "immune cell" refers to any cell from the hemopoietic origin including, but not limited to, T cells, B cells, natural killer cells, NKT cells, monocytes, dendritic cells, macrophages, neutrophils, eosinophils, basophils, mast cells, innate lymphoid cells (ILCs), and myeloid derived suppressor cells (MDSCs).

As used herein, the terms "individual," "host," "subject, and "patient" are used interchangeably herein, and refer to a mammal, including, but not limited to, humans, rodents, such as mice and rats, and other laboratory animals.

II. Chimeric Antigen Receptor T Cells

Chimeric antigen receptor T cell (CARTs) compositions and methods of their use are provided. CARTs are synthetic constructs that are designed to be expressed in host T cells or NK cells and to induce an immune response against a specific target antigen and cells expressing that antigen. The CAR typically comprises an antibody fragment, such as a scFv or Fab fragment, incorporated in a fusion protein that also comprises additional components, such as a CD3- or CD28 transmembrane domain and selective T-cell activating moieties, including the endodomains of CD3-CD28, OX40, 4-1 BB, Lck and/or ICOS. Generally, the constructs may comprise a leader sequence linked to a scFv, Fab or other antibody moiety, generally with a hinge or other linker between the scEv and a transmembrane domain. The transmembrane domain will be attached to an intracellular signaling domain, such as CD28 or CD3-, and typically will include one or more co-stimulatory domains as dis cussed below. CARs are designed with an activation domain, costimulatory domain, transmembrane domain and antigen-binding domain. The activation domain is an intracellular domain, such as CD3. The costimulatory domain can increase the activity of the CAR T cell, like proliferation and persistence. The transmembrane domain plays a role of the structural anchor. The antigen-binding domain which can combine with the target antigen is an important component of CARs and usually includes a single chain variable fragment (scFvs).

As described in U.S. Pat. Nos. 5,359,046, 5,686,281 and 6,103,521, the extracellular domain may be obtained from any of the wide variety of extracellular domains or secreted proteins associated with ligand binding and/or signal transduction. The extracellular domain may be part of a protein which is monomeric, homodimeric, heterodimeric, or associated with a larger number of proteins in a non-covalent complex. In particular, the extracellular domain may consist of an Ig heavy chain which may in turn be covalently associated with Ig light chain by virtue of the presence of CH1 and hinge regions, or may become covalently associated with other Ig heavy/light chain complexes by virtue of the presence of hinge, CH2 and CH3 domains. In the latter case, the heavy/light chain complex that becomes joined to the chimeric construct may constitute an antibody with a specificity distinct from the antibody specificity of the chimeric construct. Depending on the function of the antibody, the desired structure and the signal transduction, the entire chain may be used or a truncated chain may be used, where all or a part of the CH1, CH2, or CH3 domains may be removed or all or part of the hinge region may be removed.

Chimeric antigen receptor T cells (CAR-T cells) are T cells that have been genetically engineered to express and produce a chimeric T cell receptor. This gives the engineered T cells the ability to target a specific protein. The basis of CAR-T immunotherapy is to modify T cells to recognize cancer cells in order to more effectively target and destroy them. T cells are harvested from a subject by leukapheresis, followed by elutriation to remove myeloid cells, T lymphocyte enrichment, transgene delivery, and ex vivo expansion. The resulting CAR-T cells are infused into subjects to attack their tumors. CAR-T cells can be either derived from T cells in a subject's own blood (autologous) or derived from the T cells of another healthy donor (allogeneic). Once isolated from a subject, these T cells are genetically engineered to express a specific CAR, which programs them to target an antigen that is present on the surface of tumors. For safety, CAR-T cells are engineered to be specific to an antigen expressed on a tumor that is not expressed on healthy cells.

Methods of producing CAR T cells are known in the art and is described in U.S. Pat. Nos. 7,446,190, 7,741,465, 9,181,527, and 9,629,877.

Genetic modification for introduction of the CAR construct into T cells can be accomplished by transducing (or otherwise delivering) a T cell composition with a recombinant DNA or RNA construct, such as for example, a vector. A vector may be any agent capable of delivering or maintaining nucleic acid in a host cell, and includes viral vectors (e.g. retroviral vectors, lentiviral vectors, adenoviral vectors, or adeno-associated viral vectors), plasmids, naked nucleic acids, nucleic acids complexed with polypeptide or other molecules and nucleic acids immobilized onto solid phase particles. The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art. To achieve durable clinical responses to cell-based gene therapies, permanent transgene expression is often required. Murine gammaretroviruses and lentiviruses are two available clinical gene therapy vector systems that afford long-term CAR transgene expression. Considerable clinical evidence shows that retroviral vectors are safe when expressed in human T cells.

Selection of promoter and other regulatory sequences for protein expression are well known to those of skill in the art.

Cell specific promoters for expression in T-cells include, but are not limited to, human CD2, distal Lck, and proximal Lck. In other embodiments, non-tissue specific promoters such as non-tissue specific promoters including viral promoters such as cytomegalovirus (CMV) promoter, B-actin promoter phosphoglycerate kinase (PGK) promoter, ubiquitin promoter, and EF-1a promoter can be used. This list is not meant to be limiting. An expression construction preferably also includes sequences to allow for the replication of the expression construct. Transcription of the DNA encoding the polypeptides of the present invention by higher eukaryotes may be increased by inserting an enhancer sequence into the vector. Enhancers are cis-acting elements of DNA, usually about from 10 to 300 by that act on a promoter to increase its transcription. Examples including the SV40 enhancer on the late side of the replication origin by 100 to 270, a cytomegalovirus early promoter enhancer, the polyoma enhancer on the late side of the replication origin, and adenovirus enhancers. Preferably, a retroviral vector (either gamma-retroviral or lentiviral) is employed for the introduction of the CAR nucleic acid construct into the cell. For example, a polynucleotide encoding a co-stimulatory ligand protein (e.g., tumor necrosis factor (TNF) ligand, such as 4-1BBL, OX40L, CD70, LIGHT, and CD30L, or an Ig superfamily ligand, such as CD80 and CD86), or a receptor that binds an antigen, or a variant, or a fragment thereof, can be cloned into a retroviral vector and expression can be driven from its endogenous promoter, from the retroviral long terminal repeat, or from a promoter specific for a target cell type of interest. Non-viral vectors may be used as well.

One embodiment provides a chimeric antigen receptor T cell composition including 8F8 chimeric antigen receptor T cells. Another embodiment provides a chimeric antigen receptor T cell composition including 6G11 chimeric antigen receptor T cells. Still another embodiment provides a chimeric antigen receptor T cell composition including 12D7 chimeric antigen receptor T cells. The disclosed CARTs can be used to treat cancer, for example hepatocellular carcinoma.

Other embodiments are directed to antibodies used to produce the CARTs. One embodiment provides a recombinant monoclonal antibody having a mAb 6G11 variable light chain and a mAb 6G11 variable heavy chain. Another embodiment provides a recombinant monoclonal antibody having mAb 8F8 variable light chain and mAb 8F8 variable heavy chain. Still another embodiment provides a recombinant monoclonal antibody comprising mAb 12D7 variable light chain and mAb 12D7 variable heavy chain.

One embodiment provides a pharmaceutical composition including the disclosed antibodies and or CARTs.

Yet another embodiment provides a method for treating liver cancer by administering to a subject in need thereof an effective amount of 6G11, 8F8, or 12D7 chimeric antigen receptor T cells to treat cancer, for example hepatocellular carcinoma.

One embodiment provides a method for treating hepatocellular carcinoma in a subject in need thereof including the steps of isolating T cells from the subject, transfecting the isolated T cells with a vector containing 6G11-CAR nucleic acid sequences, optionally expanding the transfected cells in cell culture, and administering an effective mount of the transfected cells to the subject to treat hepatocellular carcinoma.

One embodiment provides a method for treating hepatocellular carcinoma in a subject in need thereof including the steps of isolating T cells from the subject, transfecting the isolated T cells with a vector containing 8F8-CAR nucleic acid sequences, optionally expanding the transfected cells in cell culture, and administering an effective mount of the transfected cells to the subject to treat hepatocellular carcinoma.

One embodiment provides a method for treating hepatocellular carcinoma in a subject in need thereof including the steps of isolating T cells from the subject, transfecting the isolated T cells with a vector containing 12D7-CAR nucleic acid sequences, optionally expanding the transfected cells in cell culture, and administering an effective mount of the transfected cells to the subject to treat hepatocellular carcinoma.

III. Pharmaceutical Compositions

The antibodies and CARTs described herein can be formulated into pharmaceutical compositions. Pharmaceutical compositions containing antibodies and/or the CARTs can be formulated for parenteral administration including by not limited to intramuscular, intraperitoneal, intravenous (IV) or subcutaneous injection.

In some in vivo approaches, the compositions disclosed herein are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected.

For the disclosed antibodies, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. Generally, for intravenous injection or infusion, dosage may be lower.

The dosage administered to a patient is typically 0.01 mg/kg to 100 mg/kg of the patient's body weight. The dosage administered to a patient can be, for example, between 0.01 mg/kg and 20 mg/kg, 0.01 mg/kg and 10 mg/kg, 0.01 mg/kg and 5 mg/kg, 0.01 and 2 mg/kg, 0.01 and 1 mg/kg, 0.01 mg/kg and 0.75 mg/kg, 0.01 mg/kg and 0.5 mg/kg, 0.01 mg/kg to 0.25 mg/kg, 0.01 to 0.15 mg/kg, 0.01 to 0.10 mg/kg, 0.01 to 0.05 mg/kg, or 0.01 to 0.025 mg/kg of the patient's body weight. Exemplary specific dosages include, but are not limited to 0.2 mg/kg, 0.3 mg/kg, 1 mg/kg, 3 mg/kg, 6 mg/kg or 10 mg/kg. A dose as low as 0.01 mg/kg is believed to be suitable to have appreciable pharmacodynamic effects. Dose levels of 0.10-1 mg/kg are predicted to be most appropriate. Higher doses (e.g., 1-30 mg/kg) would also be expected to be active. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention or fragments thereof may be reduced by enhancing uptake and tissue penetration of the antibodies by modifications such as, for example, lipidation.

In certain embodiments, the antibodies and/or CARTs are administered locally, for example by injection directly into a site to be treated.

In some embodiments, compositions disclosed herein, are administered in an aqueous solution, by parenteral injection or infusion. The formulation may also be in the form of a suspension or emulsion. In general, pharmaceutical compositions are provided including effective amounts of antibodies and/or CARTs, and optionally include pharmaceutically acceptable diluents, preservatives, solubilizers, emulsifiers, adjuvants and/or carriers. Such compositions optionally include one or more for the following: diluents, sterile water, buffered saline of various buffer content (e.g., Tris-HCl, acetate, phosphate), pH and ionic strength; and additives such as detergents and solubilizing agents (e.g., TWEEN® 20 (polysorbate-20), TWEEN® 80 (polysorbate-80)), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

IV. Combination Therapies

The disclosed antibodies and/or CARTs can be administered to a subject in need thereof alone or in combination with one or more additional therapeutic agents. In some embodiments, the additional therapeutic agents are administered separately, but simultaneously. The additional therapeutic agent can also be administered as part of the same composition. In other embodiments, the antibodies and/or CARTs and the second therapeutic agent are administered separately and at different times, but as part of the same treatment regime.

The subject can be administered a first therapeutic agent 1, 2, 3, 4, 5, 6, or more hours, or 1, 2, 3, 4, 5, 6, 7, or more days before administration of a second therapeutic agent. In some embodiments, the subject can be administered one or more doses of the first agent every 1, 2, 3, 4, 5, 6 7, 14, 21, 28, 35, or 48 days prior to a first administration of second agent. antibodies and/or CARTs can be the first or the second therapeutic agent. In some embodiments, the antibodies and/or CARTs s are administered in combination with a second therapeutic agent. The antibodies and/or CARTs and the additional therapeutic agent can be administered as part of a therapeutic regimen. For example, if a first therapeutic agent can be administered to a subject every fourth day, the second therapeutic agent can be administered on the first, second, third, or fourth day, or combinations thereof. The first therapeutic agent or second therapeutic agent may be repeatedly administered throughout the entire treatment regimen.

Exemplary additional therapeutic agents include, but are not limited to, cytokines, chemotherapeutic agents, radionuclides, other immunotherapeutics, enzymes, antibiotics, antivirals (especially protease inhibitors alone or in combination with nucleosides for treatment of HIV or Hepatitis B or C), anti-parasites (helminths, protozoans), growth factors, growth inhibitors, hormones, hormone antagonists, antibodies and bioactive fragments thereof (including humanized, single chain, and chimeric antibodies), antigen and vaccine formulations (including adjuvants), peptide drugs, anti-inflammatories, ligands that bind to Toll-Like Receptors (including but not limited to polyinosinic:polycytidylic acid (polyI:C) and CpG oligonucleotides) to activate the innate immune system, molecules that mobilize and optimize the adaptive immune system, other molecules that activate or up-regulate the action of cytotoxic T lymphocytes, natural killer cells and helper T-cells, and other molecules that deactivate or down-regulate suppressor or regulatory T-cells.

The additional therapeutic agents are selected based on the condition, disorder or disease to be treated. For example, the antibodies and/or CARTs can be co-administered with one or more additional agents that function to enhance or promote an immune response or reduce or inhibit an immune response.

A. Chemotherapeutic Agents

The antibodies and/or CARTs can be combined with one or more chemotherapeutic agents and pro-apoptotic agents. Representative chemotherapeutic agents include, but are not limited to amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epirubicin, etoposide, fludarabine, fluorouracil, gemcitabine, hydroxycarbamide, idarubicin, ifosfamide, irinotecan, leucovorin, liposomal doxorubicin, liposomal daunorubicin, lomustine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, tegafur-uracil, temozolomide, teniposide, thiotepa, tioguanine, topotecan, treosulfan, vinblastine, vincristine, vindesine, vinorelbine, or a combination thereof. Representative pro-apoptotic agents include, but are not limited to fludarabinetaurosporine, cycloheximide, actinomycin D, lactosylceramide, 15d-PGJ(2) and combinations thereof.

B. Other Immunomodulators

1. PD-1 Antagonists

In some embodiments, the antibodies and/or CARTs are co-administered with a PD-1 antagonist. Programmed Death-1 (PD-1) is a member of the CD28 family of receptors that delivers a negative immune response when induced on T cells. Contact between PD-1 and one of its ligands (B7-H1 or B7-DC) induces an inhibitory response that decreases T cell multiplication and/or the strength and/or duration of a T cell response. Suitable PD-1 antagonists are described in U.S. Pat. Nos. 8,114,845, 8,609,089, and 8,709,416, which are specifically incorporated by reference herein in their entities, and include compounds or agents that either bind to and block a ligand of PD-1 to interfere with or inhibit the binding of the ligand to the PD-1 receptor, or bind directly to and block the PD-1 receptor without inducing inhibitory signal transduction through the PD-1 receptor.

In some embodiments, the PD-1 receptor antagonist binds directly to the PD-1 receptor without triggering inhibitory signal transduction and also binds to a ligand of the PD-1 receptor to reduce or inhibit the ligand from triggering signal transduction through the PD-1 receptor. By reducing the number and/or amount of ligands that bind to PD-1 receptor and trigger the transduction of an inhibitory signal, fewer cells are attenuated by the negative signal delivered by PD-1 signal transduction and a more robust immune response can be achieved.

It is believed that PD-1 signaling is driven by binding to a PD-1 ligand (such as B7-H1 or B7-DC) in close proximity to a peptide antigen presented by major histocompatibility complex (MEW) (see, for example, Freeman, Proc Natl Acad Sci U.S.A, 105:10275-10276 (2008)). Therefore, proteins, antibodies or small molecules that prevent co-ligation of PD-1 and TCR on the T cell membrane are also useful PD-1 antagonists.

In some embodiments, the PD-1 receptor antagonists are small molecule antagonists or antibodies that reduce or interfere with PD-1 receptor signal transduction by binding to ligands of PD-1 or to PD-1 itself, especially where co-ligation of PD-1 with TCR does not follow such binding, thereby not triggering inhibitory signal transduction through the PD-1 receptor. Other PD-1 antagonists contemplated by the methods of this invention include antibodies that bind to PD-1 or ligands of PD-1, and other antibodies.

Suitable anti-PD-1 antibodies include, but are not limited to, those described in the following U.S. Pat. Nos. 7,332, 582, 7,488,802, 7,521,051, 7,524,498, 7,563,869, 7,981,416, 8,088,905, 8,287,856, 8,580,247, 8,728,474, 8,779,105, 9,067,999, 9,073,994, 9,084,776, 9,205,148, 9,358,289, 9,387,247, 9,492,539, 9,492,540, all of which are incorporated by reference in their entireties.

See also Berger et al., Clin Cancer Res, 14:30443051 (2008).

Exemplary anti-B7-H1 (also referred to as anti-PD-L1) antibodies include, but are not limited to, those described in the following U.S. Pat. Nos. 8,383,796, 9,102,725, 9,273, 135, 9,393,301, and 9,580,507 all of which are specifically incorporated by reference herein in their entirety.

For anti-B7-DC (also referred to as anti-PD-L2) antibodies see U.S. Pat. Nos. 7,411,051, 7,052,694, 7,390,888, 8,188,238, and 9,255,147 all of which are specifically incorporated by reference herein in their entirety.

Other exemplary PD-1 receptor antagonists include, but are not limited to B7-DC polypeptides, including homologs and variants of these, as well as active fragments of any of the foregoing, and fusion proteins that incorporate any of these. In some embodiments, the fusion protein includes the soluble portion of B7-DC coupled to the Fc portion of an antibody, such as human IgG, and does not incorporate all or part of the transmembrane portion of human B7-DC.

The PD-1 antagonist can also be a fragment of a mammalian B7-H1, for example from mouse or primate, such as a human, wherein the fragment binds to and blocks PD-1 but does not result in inhibitory signal transduction through PD-1. The fragments can also be part of a fusion protein, for example an Ig fusion protein.

Other useful polypeptides PD-1 antagonists include those that bind to the ligands of the PD-1 receptor. These include the PD-1 receptor protein, or soluble fragments thereof, which can bind to the PD-1 ligands, such as B7-H1 or B7-DC, and prevent binding to the endogenous PD-1 receptor, thereby preventing inhibitory signal transduction. B7-H1 has also been shown to bind the protein B7.1 (Butte et al., Immunity, Vol. 27, pp. 111-122, (2007)). Such fragments also include the soluble ECD portion of the PD-1 protein that includes mutations, such as the A99L mutation, that increases binding to the natural ligands (Molnar et al., PNAS, 105:10483-10488 (2008)). B7-1 or soluble fragments thereof, which can bind to the B7-H1 ligand and prevent binding to the endogenous PD-1 receptor, thereby preventing inhibitory signal transduction, are also useful.

PD-1 and B7-H1 anti-sense nucleic acids, both DNA and RNA, as well as siRNA molecules can also be PD-1 antagonists. Such anti-sense molecules prevent expression of PD-1 on T cells as well as production of T cell ligands, such as B7-H1, PD-L1 and/or PD-L2. For example, siRNA (for example, of about 21 nucleotides in length, which is specific for the gene encoding PD-1, or encoding a PD-1 ligand, and which oligonucleotides can be readily purchased commercially) complexed with carriers, such as polyethyleneimine (see Cubillos-Ruiz et al., J. Clin. Invest. 119(8): 2231-2244 (2009), are readily taken up by cells that express PD-1 as well as ligands of PD-1 and reduce expression of these receptors and ligands to achieve a decrease in inhibitory signal transduction in T cells, thereby activating T cells.

2. CTLA4 Antagonists

In some embodiments, the second therapeutic agent is an antagonist of CTLA4, for example an antagonistic anti-CTLA4 antibody. An example of an anti-CTLA4 antibody contemplated for use in the methods of the invention includes an antibody as described in PCT/US2006/043690 (Fischkoff et al., WO/2007/056539).

Dosages for anti-PD-1, anti-B7-H1, and anti-CTLA4 antibody, are known in the art and can be in the range of, for example, 0.1 to 100 mg/kg, or with shorter ranges of 1 to 50 mg/kg, or 10 to 20 mg/kg. An appropriate dose for a human subject can be between 5 and 15 mg/kg, with 10 mg/kg of antibody (for example, human anti-PD-1 antibody) being a specific embodiment.

Specific examples of an anti-CTLA4 antibody useful in the methods of the invention are Ipilimumab, a human anti-CTLA4 antibody, administered at a dose of, for example, about 10 mg/kg, and Tremelimumab a human anti-CTLA4 antibody, administered at a dose of, for example, about 15 mg/kg. See also Sammartino, et al., Clinical Kidney Journal, 3(2):135-137 (2010), published online December 2009.

In other embodiments, the antagonist is a small molecule. A series of small organic compounds have been shown to bind to the B7-1 ligand to prevent binding to CTLA4 (see Erbe et al., J Biol Chem, 277:7363-7368 (2002). Such small organics could be administered alone or together with an anti-CTLA4 antibody to reduce inhibitory signal transduction of T cells.

3. Potentiating Agents

In some embodiments, additional therapeutic agents include a potentiating agent. The potentiating agent acts to increase efficacy the immune response up-regulator, possibly by more than one mechanism, although the precise mechanism of action is not essential to the broad practice of the present invention.

In some embodiments, the potentiating agent is cyclophosphamide. Cyclophosphamide (CTX, Cytoxan®, or Neosar®) is an oxazahosphorine drug and analogs include ifosfamide (IFO, Ifex), perfosfamide, trophosphamide (trofosfamide; Ixoten), and pharmaceutically acceptable salts, solvates, prodrugs and metabolites thereof (US patent application 20070202077 which is incorporated in its entirety). Ifosfamide (MITOXANA®) is a structural analog of cyclophosphamide and its mechanism of action is considered to be identical or substantially similar to that of cyclophosphamide. Perfosfamide (4-hydroperoxycyclophosphamide) and trophosphamide are also alkylating agents, which are structurally related to cyclophosphamide. For example, perfosfamide alkylates DNA, thereby inhibiting DNA replication and RNA and protein synthesis. New oxazaphosphorines derivatives have been designed and evaluated with an attempt to improve the selectivity and response with reduced host toxicity (Liang J, et al., "Design of New Oxazaphosphorine Anticancer Drugs", Curr Pharm Des, 13(9):963-78 Review 2007). These include mafosfamide (NSC 345842), glufosfamide (D19575, beta-D-glucosylisophosphoramide mustard), S-(−)-bromofosfamide (CBM-11), NSC 612567 (aldophosphamide perhydrothiazine) and NSC 613060 (aldophosphamide thiazolidine). Mafosfamide is an oxazaphosphorine analog that is a chemically stable 4-thioethane sulfonic acid salt of 4-hydroxy-CPA. Glufosfamide is IFO derivative in which the isophosphoramide mustard, the alkylating metabolite of IFO, is glycosidically linked to a beta-D-glucose molecule. Additional cyclophosphamide analogs are described in U.S. Pat. No. 5,190,929 entitled "Cyclophosphamide analogs useful as anti-tumor agents" which is incorporated herein by reference in its entirety.

While CTX itself is nontoxic, some of its metabolites are cytotoxic alkylating agents that induce DNA crosslinking and, at higher doses, strand breaks. Many cells are resistant to CTX because they express high levels of the detoxifying enzyme aldehyde dehydrogenase (ALDH). CTX targets proliferating lymphocytes, as lymphocytes (but not hematopoietic stem cells) express only low levels of ALDH, and cycling cells are most sensitive to DNA alkylation agents.

Low doses of CTX (<200 mg/kg) can have immune stimulatory effects, including stimulation of anti-tumor immune responses in humans and mouse models of cancer (Brode & Cooke Crit Rev, Immunol, 28:109-126 (2008)). These low doses are sub-therapeutic and do not have a direct anti-tumor activity. In contrast, high doses of CTX inhibit the anti-tumor response. Several mechanisms may explain the role of CTX in potentiation of anti-tumor immune response: (a) depletion of CD4+CD25+FoxP3+ Treg (and specifically proliferating Treg, which may be especially suppressive), (b) depletion of B lymphocytes; (c) induction of nitric oxide (NO), resulting in suppression of tumor cell growth; (d) mobilization and expansion of CD11b+Gr-1+ MDSC. These primary effects have numerous secondary effects; for example, following Treg depletion macrophages produce more IFN-γ and less IL-10. CTX has also been shown to induce type I IFN expression and promote homeostatic proliferation of lymphocytes.

Treg depletion is most often cited as the mechanism by which CTX potentiates the anti-tumor immune response. This conclusion is based in part by the results of adoptive transfer experiments. In the AB1-HA tumor model, CTX treatment at Day 9 gives a 75% cure rate. Transfer of purified Treg at Day 12 almost completely inhibited the CTX response (van der Most et al., Cancer Immunol. Immunother, 58:1219-1228 (2009). A similar result was observed in the HHD2 tumor model: adoptive transfer of CD4+ CD25+ Treg after CTX pretreatment eliminated therapeutic response to vaccine (Taieb, J., J Immunol, 176:2722-2729 (2006)).

Numerous human clinical trials have demonstrated that low dose CTX is a safe, well-tolerated, and effective agent for promoting anti-tumor immune responses (Bas, & Mastrangelo Cancer Immunol, Immunother, 47:1-12 (1998)).

The optimal dose for CTX to potentiate an anti-tumor immune response, is one that lowers overall T cell counts by lowering Treg levels below the normal range but is sub-therapeutic (see Machiels et al., Cancer Res, 61:3689-3697 (2001)).

In human clinical trials where CTX has been used as an immunopotentiating agent, a dose of 300 mg/m2 has usually been used. For an average male (6 ft., 170 pound (78 kg) with a body surface area of 1.98 m2), 300 mg/m2 is 8 mg/kg, or 624 mg of total protein. In mouse models of cancer, efficacy has been seen at doses ranging from 15-150 mg/kg, which relates to 0.45-4.5 mg of total protein in a 30 g mouse (Machiels et al., Cancer Res, 61:3689-3697 (2001), Hengst et al., Cancer Res, 41:2163-2167 (1981), Hengst, Cancer Res, 40:2135-2141 (1980))).

For larger mammals, such as a primate, such as a human, patient, such mg/m² doses may be used but unit doses administered over a finite time interval may also be used. Such unit doses may be administered on a daily basis for a finite time period, such as up to 3 days, or up to 5 days, or up to 7 days, or up to 10 days, or up to 15 days or up to 20 days or up to 25 days, are all specifically contemplated by the invention. The same regimen may be applied for the other potentiating agents recited herein.

In other embodiments, the potentiating agent is an agent that reduces activity and/or number of regulatory T lymphocytes (T-regs), such as Sunitinib (SUTENT®), anti-TGFβ or Imatinib (GLEEVAC®). The recited treatment regimen may also include administering an adjuvant.

Useful potentiating agents also include mitosis inhibitors, such as paclitaxol, aromatase inhibitors (e.g. Letrozole) and angiogenesis inhibitors (VEGF inhibitors e.g., Avastin, VEGF-Trap) (see, for example, Li et al., Clin Cancer Res, November 15; 12(22):6808-16 (2006.)), anthracyclines, oxaliplatin, doxorubicin, TLR4 antagonists, and IL-18 antagonists.

EXAMPLES

Example I: 1. Generation of hGPC3-Specific mAbs that Bind HCC Tumor Cells

Materials and Methods

Cells

Peripheral blood mononuclear cells (PBMC) buffy coats were obtained from local blood bank and PBMC were separated by Ficoll-Hypaque column and frozen in aliquots in liquid nitrogen. Jurkat, HEK293T, and HepG2 cells were from the American Type Culture Collection; Huh7 cells were from Dr. Satyanayana Ande of Augusta University Georgia Cancer Center. Cells were checked for mycoplasma by a PCR test (Fisher Scientific) and cultured for no more than eight passages before use to assure their authenticity.

Mice

BalB/C mice were purchased from Charles River. The immunocompromised NOD-scid IL2Rgammanull (NSG) mice breeding pairs were obtained from Jackson Laboratory and bred in house. Animal protocols were approved by the Institutional Animal Care and Use Committee of Augusta University.

Generation of mAbs

The mAbs were generated as previously descried (Xiao H, et al., Blood Cells Mol Dis 44: 127-32 (2010)). Female BALB/c mice of age 6-10 weeks were immunized with 100 μg recombinant hGPC3 protein (AA25-560) with complete Freund's adjuvant (Sigma-Aldrich) by footpad injection. Three weeks later, mice were boosted twice or three times with 70 μg recombinant hGPC3 protein together with incomplete Freund's adjuvant (Sigma-Aldrich) by footpad injection at 2-week intervals. Anti-hGPC3 antibody titer in mouse serum was measured by ELISA. A final boost was carried out by tail vein injection of 50 μg/mouse recombinant hGPC3 in 100 μl PBS. Three days after the final boost, mice were sacrificed and splenocytes were generated to fuse with fusion partner NS-1 myeloma cells in the presence of 50% PEG1500. Hybridomas were selected by HAT medium, and the positive ones were screened by ELISA. Sub-cloning was performed three times using the limiting dilution method.

Statistical Analysis

Statistical analyses were performed using Student's t test or 2way ANOVA in the prism software (GraphPad Inc.).

Results

Figure 1E:
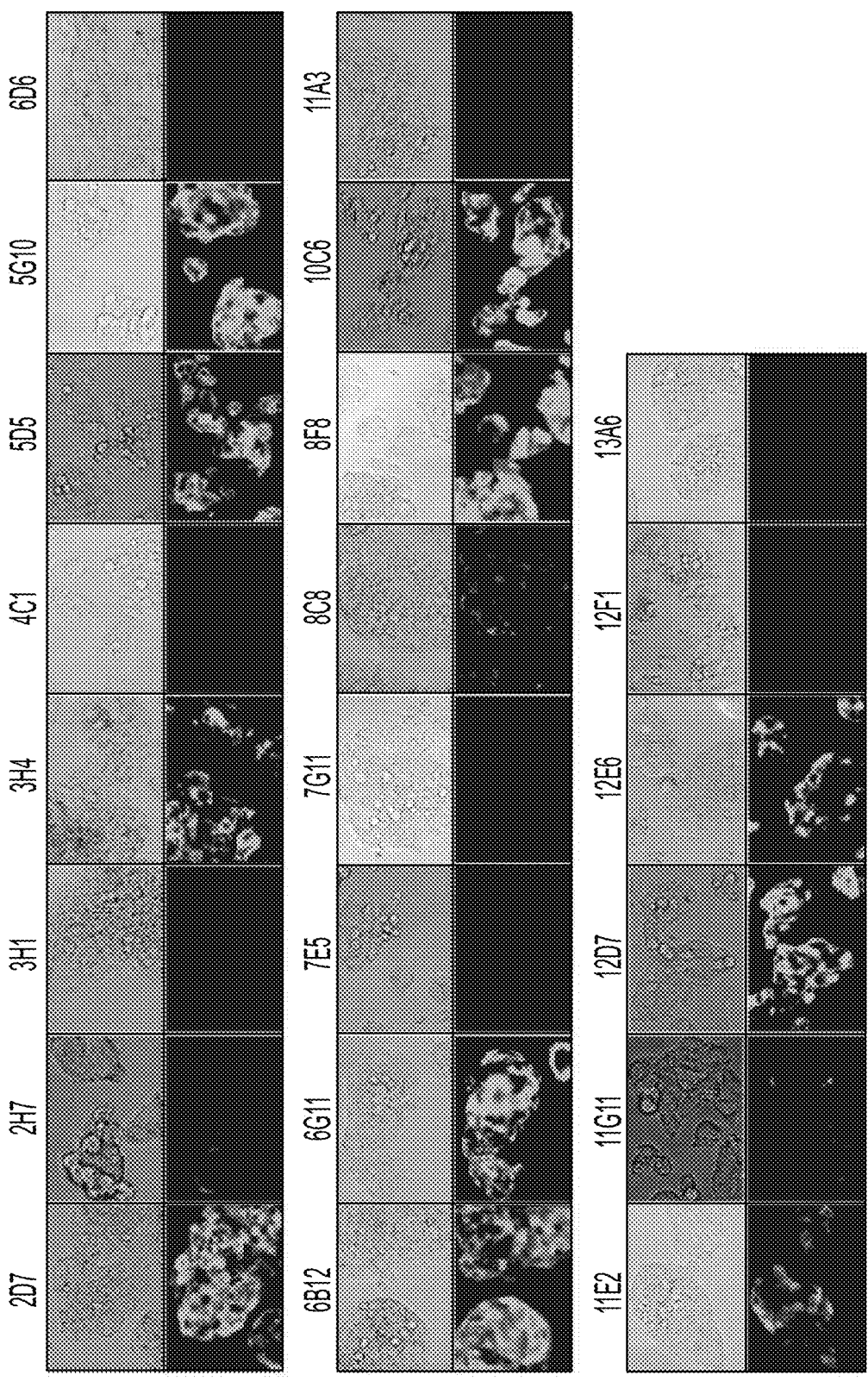
FIG. 1E is a panel showing immune fluorescent staining of HepG2 tumor cells with the indicated hGPC3-specific mAbs.
Figure 1F:
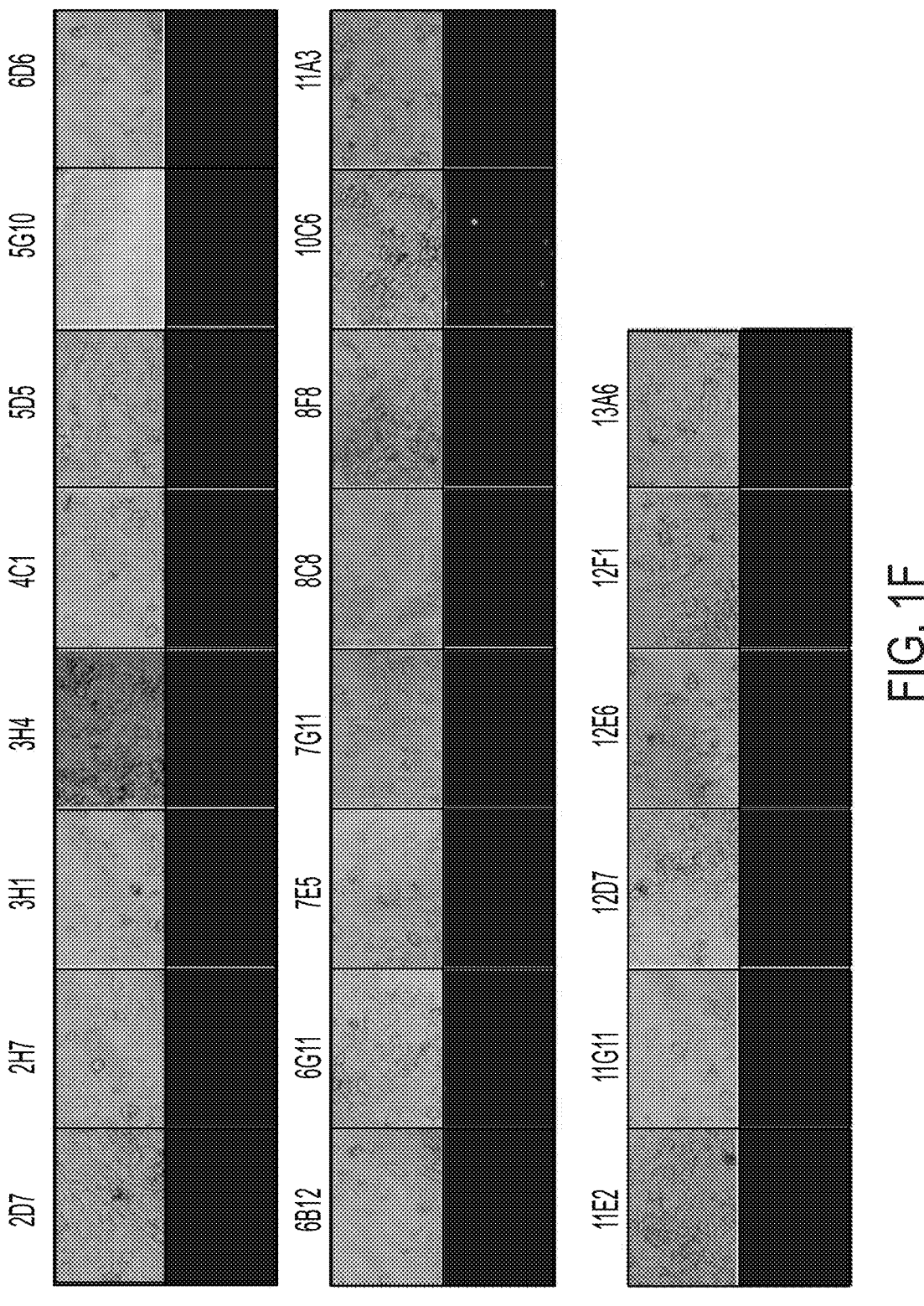
FIG. 1F is a panel showing immune fluorescent staining of the Huh7 cells by indicated hGPC3-specific mAbs.
Figure 1G:
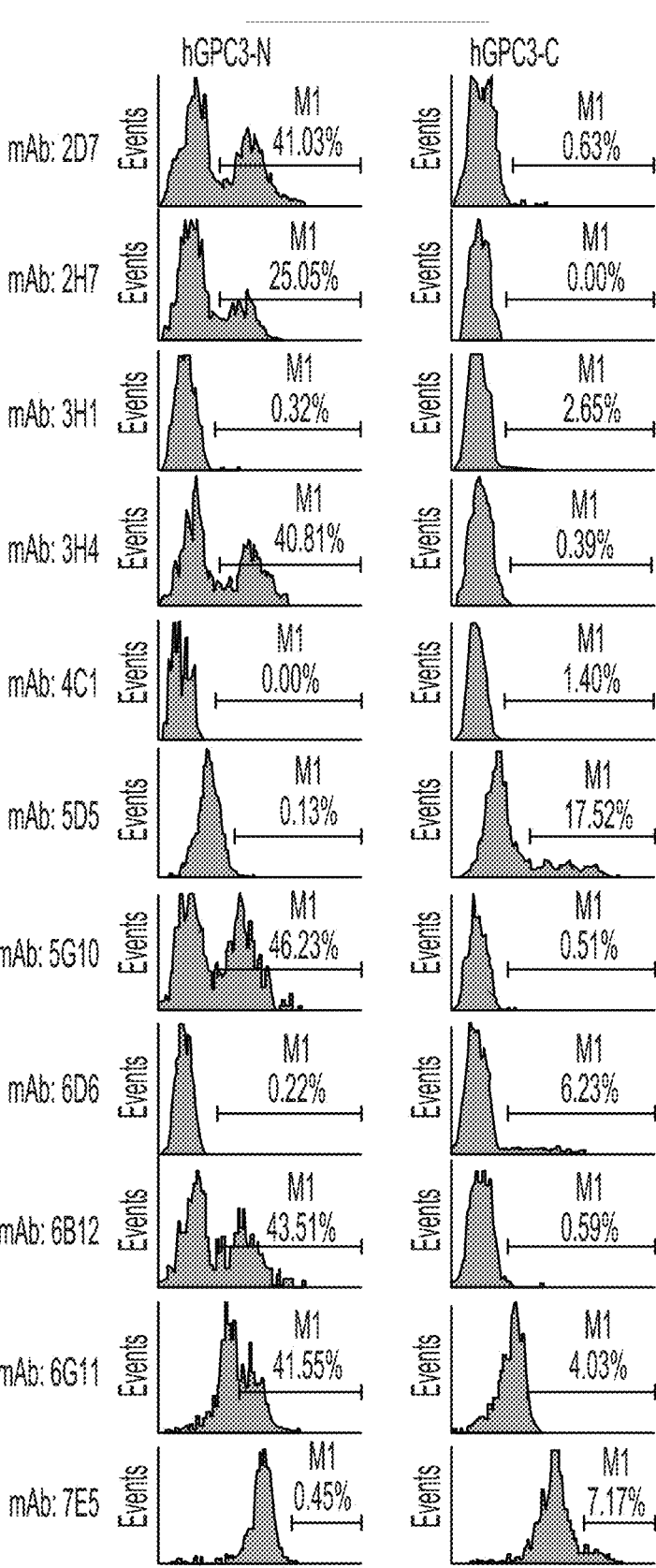
FIG. 1G is a panel of graphs showing intracellular staining of the 293T cells transfected with hGPC3-N or hGPC3-C fragment gene with different hGPC3 specific mAbs. The gate was set by the parental 293 cells without transfection.
Figure 1G:
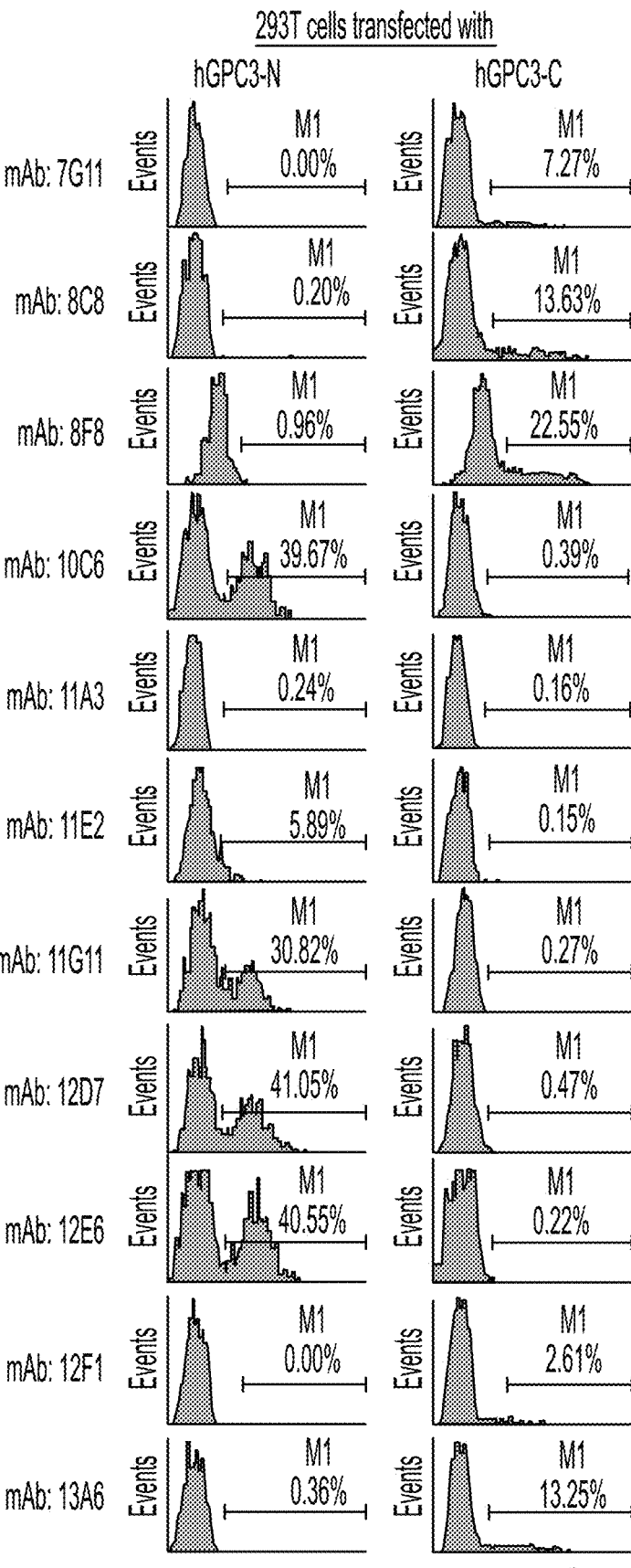

In the first set of experiments, hGPC3-specific mAbs that bound HCC tumor cells were developed. By ELISA, using soluble hGPC3 protein, we identified 22 mAbs (FIG. 1A). Based on heavy chains, there are 8 IgM, 7 IgG1, 3 IgG2a, 3 IgG2b, and 1 IgA. All the mAbs have the κ chain. Among them, 11 mAbs strongly, and 3 weakly, stained HepG2 cells (FIG. 1B). The other 8 mAbs were unable to stain HepG2 cells (FIG. 1E). Furthermore, 7 of them (2D7, 3H4, 5D5, 6G11, 8F8, 10C6, and 12D7) that positively stained HepG2 cells also stained the hGPC3low Huh7 cells albeit with a lower intensity (FIG. 1F). Because the hGPC3 molecule on cell surface can be cleaved into 40 Kd N- and 30 Kd C-fragments, we studied whether the mAbs bound to hGPC3 N- or C-fragments. To this end, we created two recombinant plasmids that expressed the amino acid (AA) 1-358 (hGPC3-N) and AA359-580 (hGPC3-C fragment), respectively (FIG. 1C). 293T cells were transfected with plasmid DNA and stained with mAbs. We found that out of the 14 mAbs that stained HepG2 tumor cells, 11 of them bound to the hGPC3-N, while only 3 bound to the hGPC3-C fragment (FIGS. 1D and 1G). This data suggests that N-terminal epitopes might be more accessible. The other 8 mAbs that were unable to stain HepG2 cells did not bind to either hGPC3-N or hGPC3-C fragment (FIG. 1G). The characterization of the 22 mAbs was summarized in FIG. 1A.

Example II: Identification of the mAbs that Stain Only the HCC Tumor but not Adjacent Normal Liver Tissues

Materials and Methods

Immunohistochemical Staining (IHC)

HCC and liver tissues were obtained from cancer clinics in Georgetown cancer center. Tissues were sectioned and stained in the clinical pathology lab of Georgetown cancer center. The paraformaldehyde-fixed and paraffin-embedded blocks of health liver, adjacent normal liver and HCC tissue are from cases operated at Lombardi Cancer Center of Georgetown University. All patients gave informed consent, and the study was authorized by the respective Hospital Ethics Committees. Pathologic slides were stained with one of the following purified mAbs (6G11, 12D7, and 12E6, 8C8 and 8F8). Secondary antibodies were either goat-anti-mouse IgM or goat-anti-mouse IgG (Vector Labs). Immunoscores were calculated by adding intensity and region of staining: 0, 1, 2, 3 correspond to no, weak, moderate, and high intensity staining; 0, 1, 2, 3 correspond to no, focal as less than 10% of cells, regional as 10%-50% of cells, and diffuse region as >50% of cells staining.

Figures 2A, 2B:
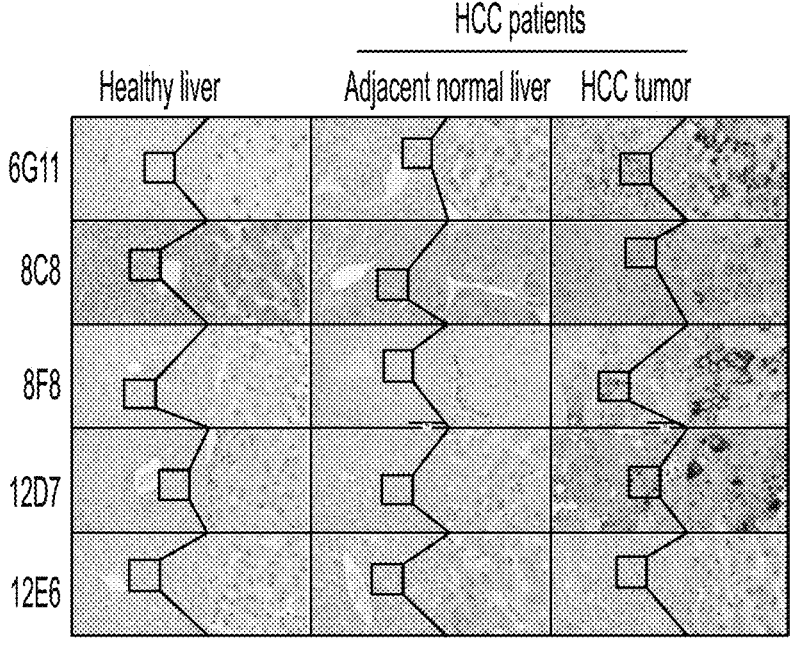
FIG. 2A is a panel of micrographs showing IHC staining of liver tissues. Representative IHC staining of healthy liver and the paired HCC and the adjacent normal tissues of the same livers. A low and high magnifications were presented. Dark spots indicated positive staining.
FIG. 2B is a table showing the summary of IHC staining of multiple tissue samples by 5 mAbs. ANL: adjacent normal liver tissues. The highest immunoscore is 8, the lowest score is 0.
Figure 2C:
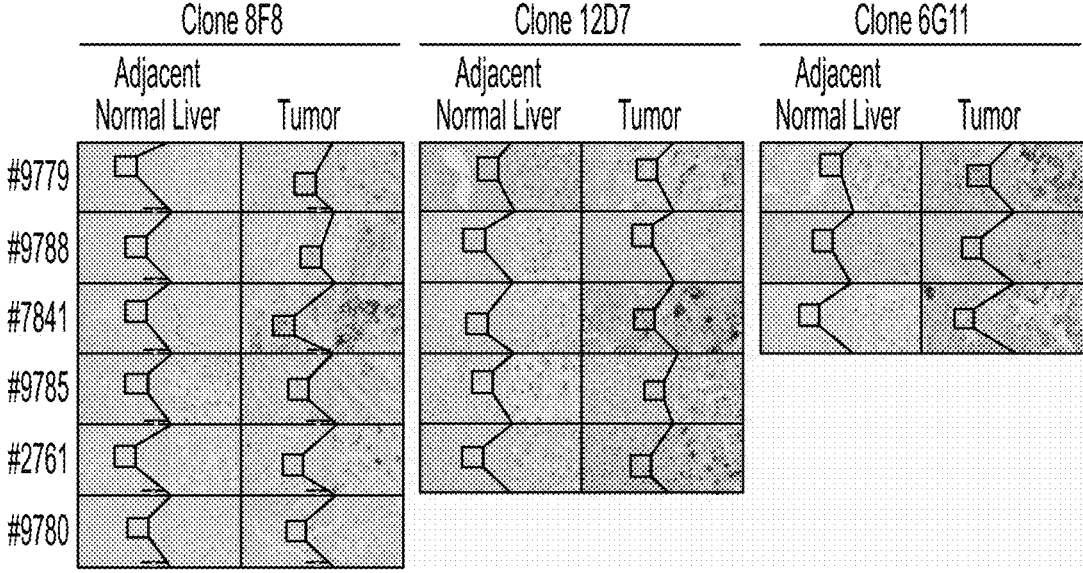
FIG. 2C is a panel of micrographs showing IHC staining of HCC tumor tissues and their paired adjacent normal liver tissues by mAbs by 5 mAbs. Some negative staining by mAbs were not presented.
Figure 2C:
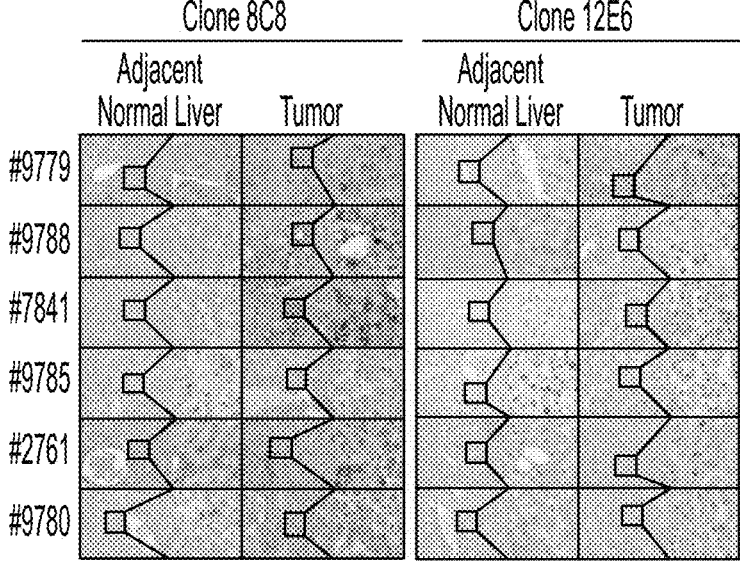

Results 5 mAbs, 3 for N-fragment (6G11, 12D7, and 12E6) and 2 for C-fragment (8C8 and 8F8), were purified and assayed IHC staining of the HCC tumor tissues and their paired adjacent normal tissues to further study their specificity. Healthy liver tissues were also included as controls. Our data showed that 3 of the mAbs (6G11, 8F8, and 12D7) were able to specifically stain HCC tumor tissues but not the adjacent normal liver tissues (FIGS. 2A-2C). However, the other two mAbs (8C8 and 12E6) had a higher non-specific staining of normal adjacent liver tissues and even healthy liver tissues. Thus, only the mAbs 6G11, 8F8, and 12D7 were used for further studies.

Example III: Identification of the mAb's cDNA Sequences

Materials and Methods

Identification of the mAb's cDNA Sequences

To obtain the cDNA sequences of mAbs, we used the technique of 5' rapid amplification of complementary DNA ends (5' RACE) (Walchli, S., et al., PLoS One 6: e27930 (2011); Zhu, W., et al., Hepatology 68: 574-89 (2018)). Briefly, total RNA was isolated from hybridomas, and complementary DNA was generated with an oligo di primer. PolyC was added to the 5' end of complementary DNA by terminal transferase. Then, PCR was conducted to amplify the cDNA by using the 5' pGI primer: CACCGGGIIGG-GIIGGGIIGG (SEQ ID NO: 25), and one of the following 3' primers corresponding to the constant (C) region of the mouse IgM heavy chain or the kappa chain:

1. For 6G11 and 12D7, IgM heavy chain primer (mIgM-OP) and chain primer (mIgk-OP) were designed as 3' primers.

```
a. Mouse IgM heavy chain primer (mIgM-MOP):
                                    (SEQ ID NO: 26)
   CCTGGATGACTTCAGTGTTGTTCTG;

b. Mouse κ chain primer (mIgk-OP):
                                    (SEQ ID NO: 27)
   CACTGCCATCAATCTTCCACTTG.
```

2. The PCR. products were purified and sequenced. Based on the preliminary sequences, internal 3' primers were designed. Together with 5' pGI primer, a second and more specific PCR was run.

```
a. Mouse IgM heavy chain internal 3' primer
   (mIgM-IP):
                                    (SEQ ID NO: 28)
   GGGGGAAGACATTTGGGAAGG;

b. Mouse κ chain internal 3' primer (mIgk-IP):
                                    (SEQ ID NO: 29)
   CACTGGATGGTGGGAAGATGG.
```

3. Because immunoglobulin class of IgG2a, different heavy chain 3' primers were used:

```
a. Mouse IgG2a heavy chain primer (mIgG2aH-OP):
                                    (SEQ ID NO: 30)
   GGTTACAGTCACTGAGCTGCTG;

b. Mouse IgG2a heavy chain internal primer
   (mIgG2aH-IP):
                                    (SEQ ID NO: 31)
   GGAGCCAGTTGTATCTCCACAC.
```

Results cDNA sequences of the heavy chain variable region (VH) and the light chain variable region (VL) of mAbs 6G11, 8F8, and 12D7 from their corresponding hybridoma clones were identified. The deduced AA sequences of the VL and VH were compared to the Ig sequences compiled in the international ImMunoGeneTics information system (IMGT) databank (37). The AA sequences showed that 6G11 VL has 99.64% homology with IGKV15-103*01 (1AA difference)

and its J region is identical to IGKJ1*01. In contrast, the 6G11 VH has 94.44% homology with IGHV1S5*01 and its J region has 96.3% of homology to IGHJ4*01. The 8F8 VL has 99% homology with IGK15-135*01 and its J region is identical to IGKJ5*01, while 8F8 VH has 94.9% homology with IGHV5-9-2*01 and its J region has 85.5% homology to IGHJ2*01. The 12D7 VL is identical to IGKV6-15*01 and IGKJ5*01, while 12D7 VH has 89.8% homology with IGHV1S5*01 and its J region has 85.7% homology with IGHJ3*01. The results were summarized in Table 1.

| mAbs | Chains | V | J |
|------|--------|---|---|
| 6G11 | L | IGKV15-103*01 (99.64% homology) | IGKJ1*01 (100% homology) |
| | H | IGHVS5*01 (94.44% homology) | IGHJ4*01 (96.30% homology) |
| 8F8 | L | IGKV15-135*01 (99% homology) | IGKJ5*01 (100% homology) |
| | H | IGHV5-9-2*01 (94.9% homology) | IGHJ2*01 (85.7% homology) |
| 12D7 | L | IGKV6-15*01 (100 homology) | IGKJ5*01 (100 homology) |
| | H | IGHV1S5*01 (89.8% homology) | IGHJ3*01 (85.7% homology) |

Example IV: Affinity of mAbs 6G11, 8F8, and 12D7

Materials and Methods

BioLayer Interferometry

Kinetics experiments were performed using the ForteBio Octet Red96 platform. All data were collected at 25° C. with orbital shaking at 1,000 rpm in 200 μL in 96-well black flat bottom plates (Greiner Bio-one). Anti-hIgG Fc Capture Sensor (ForteBio) were equilibrated for 10 min in 1×kinetics buffer prior to loading with 5 μg/mL of mAbs for 2 min. After the loading step, a 30 s baseline in 1×kinetics buffer was established before association with a range of concentrations of GPC3 for 2 min. Following mAbs association with GP, there was a 10-minute of dissociation step in kinetic buffer. For all experiments, two reference sensors without association to mAbs were used to account for nonspecific binding of analyte to the sensor and the system drift. All data were fit globally to a 1:1 Langmuir binding model using data analysis software 9.0 (ForteBio).

Results

Figure 3A:
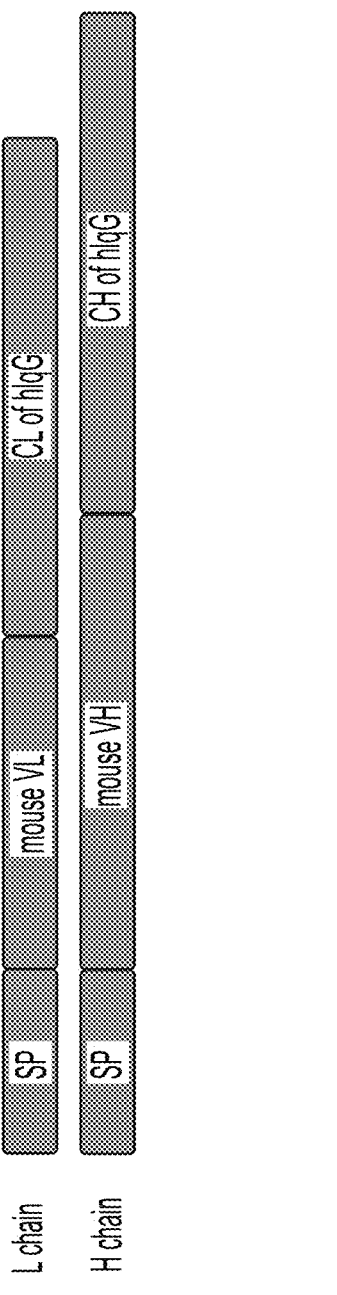
FIG. 3A is an illustration showing the schematic structure of the recombinant mAbs. SP: signal peptide of human IgG; VL: variable region of light chain; VH: variable region of heavy chain; CL: constant region of human IgG light chain; CH: constant region of human IgG heavy chain.
Figure 3B:
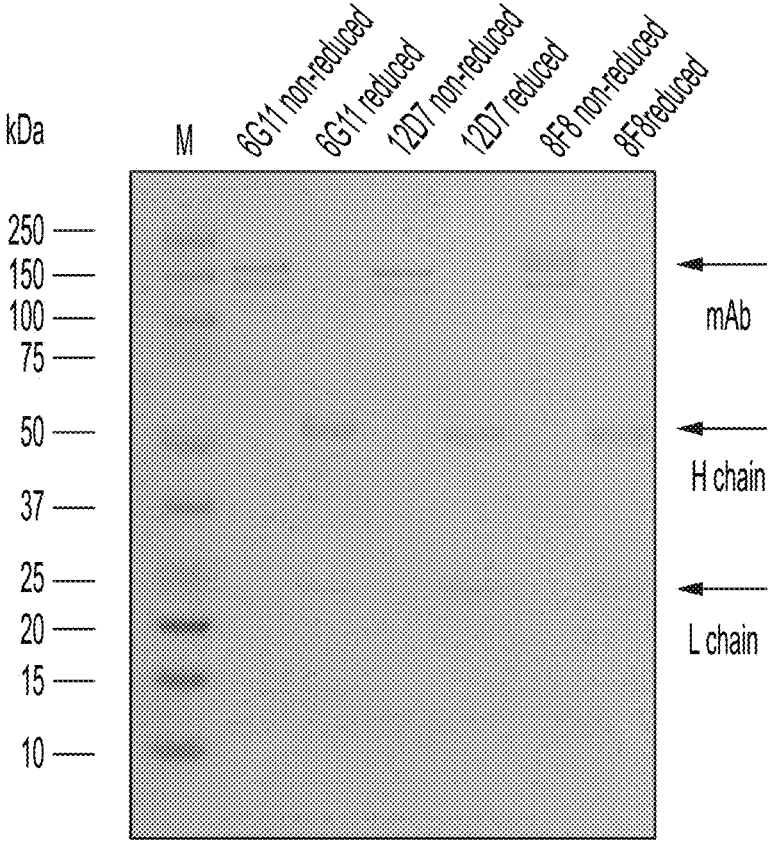
FIG. 3B is gel showing PAGE analysis of purified recombinant mAbs under reduced and non-reduced condition. mAbs were purified from the 293 cells after co-transfection of the L and H chain expressing plasmids. Gel was stained with SimplyBlue SafeStain.
Figure 3C:
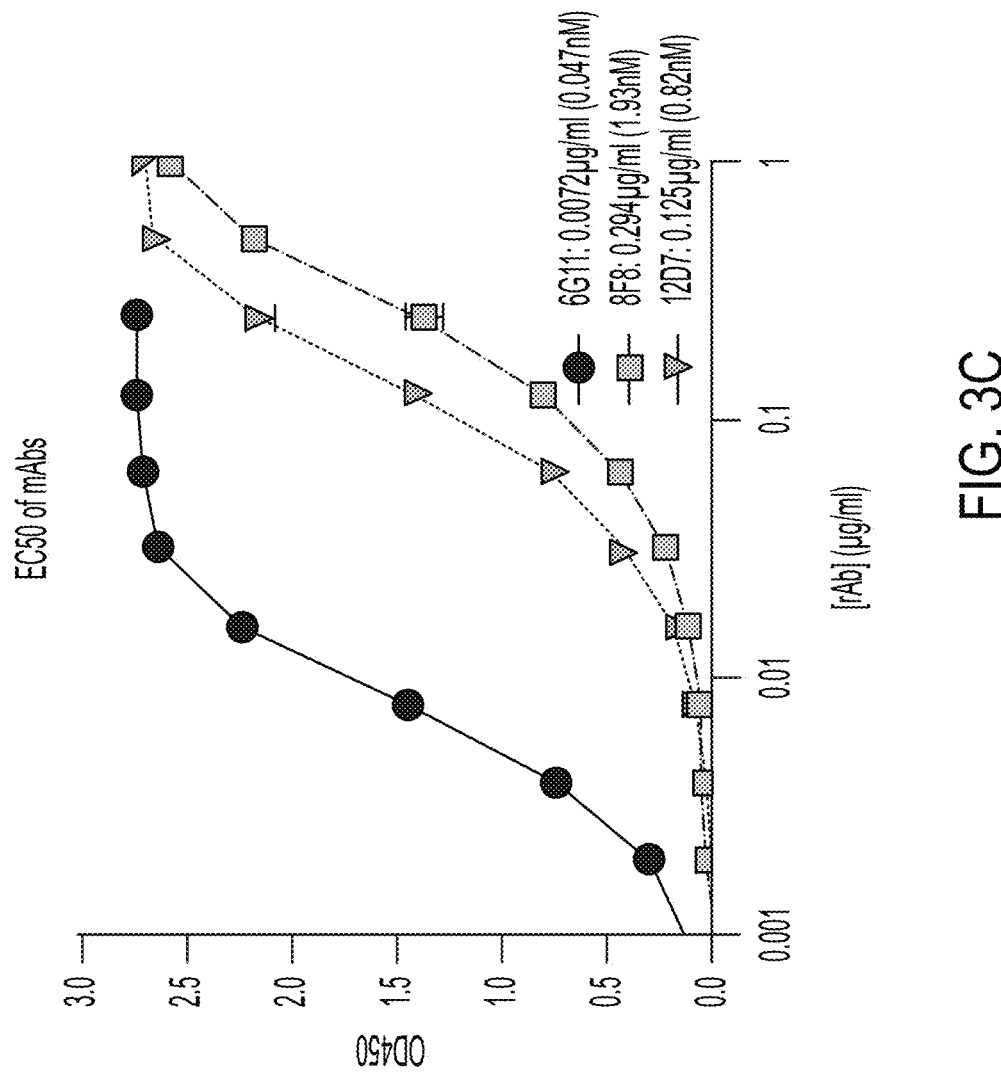
FIG. 3C is a graph showing the EC50 of recombinant mAbs by ELISA.
Figure 3D:
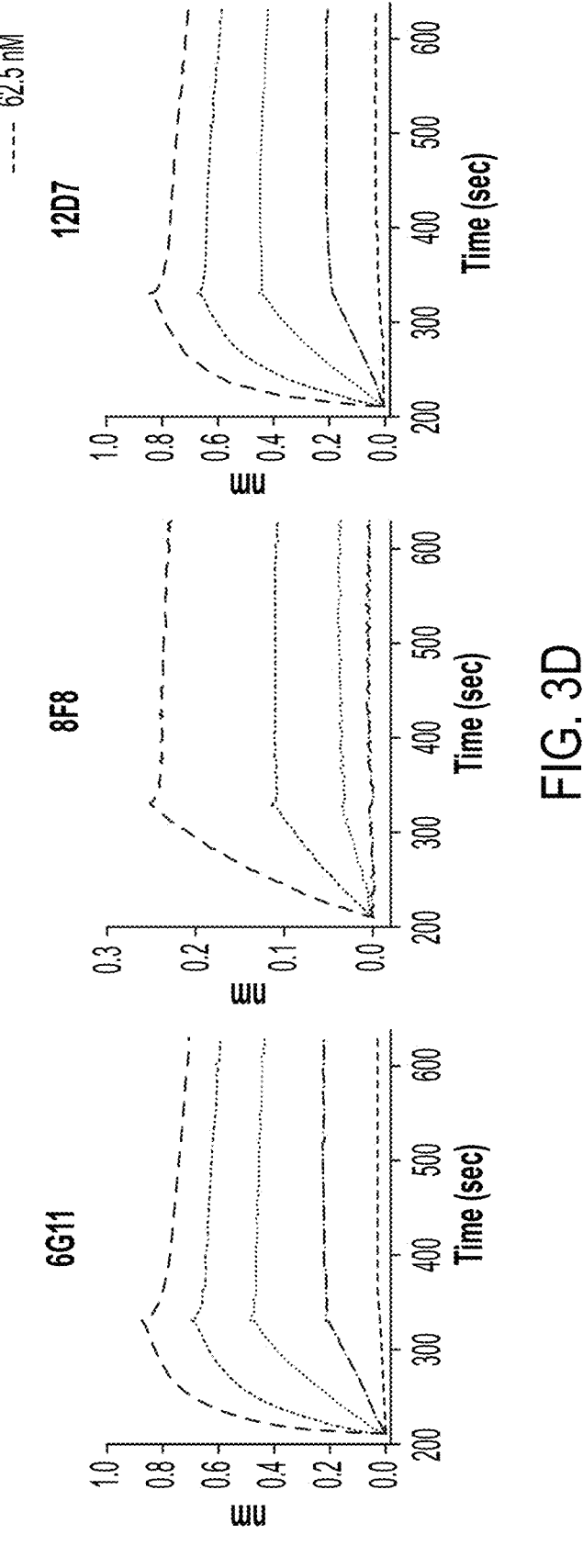
FIG. 3D is a panel of graphs showing the Kd value of each mAbs was measured by BLI. Each experiment was repeated at least 3 times and similar data were obtained.
Figure 3E:
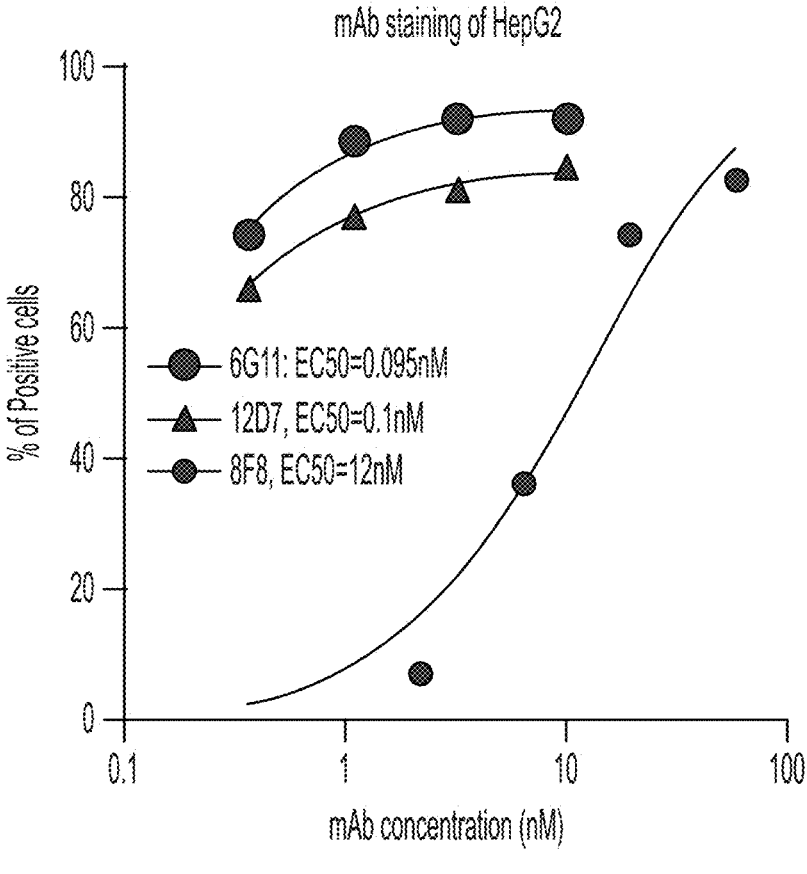
FIG. 3E is a graph showing the Kd value of mAbs 6G11, 8F8, and 12D7 for staining HepG2 tumor cells. Immunofluorescent staining was conducted for HepG2 tumor cells using the mAbs at different concentration. Based on the percent of positive cells and the mAb concentration, the Kd value was calculated by Prism software.

The 3 mAbs belong to different Ig classes, i.e., 6G11 and 12D7 are IgM, whereas 8F8 is IgG2a. To fairly compare their affinity, mAbs were generated recombinant using their VL and VH and a same human IgG constant region. FIG. 3A illustrates the structure of the recombinant mAbs. The mAbs were expressed and purified from 293 cells (FIG. 3B). The mAb's affinity was first studied by ELISA and the data showed that all 3 mAbs have high affinity for hGPC3 (FIG. 3C) (EC50 values in the range of subnanomolar to low nanomolar level). The mAb's affinity was also studied by BioLayer Interferometry (BLI). By this biophysical approach, the Kd value of these mAbs binding to hGPC3 were at nanomolar levels, 7.4 nM for 6G11, 9.8 nM for 12D7, and 23 nM for 8F8 (FIG. 3D). The affinity data obtained by ELISA assay and BLI are in the same order, i.e., 6G11>12D7>8F8. Because the purpose of developing the mAbs is to bind hGPC3 molecules on the tumor cell surface, we determined the affinity of the mAbs for hGPC3 on HepG2 cells. Consistent with the ELISA and BLI data, the 6G11 and 12D7 have high affinity (EC50: 0.095 nM and 0.1 nM, respectively), while 8F8 mAb has low affinity for hGPC3 on HepG2 tumor cells (EC50: 12 nM) (FIG. 3E).

Example V: Epitopes Recognized by the mAbs

Materials and Methods

ELISA Assay with Synthetic Peptides 96-well Flat-Bottom Immuno Plates (from Thermo Fisher) were coated with 4 ug of PBS-diluted peptides, overnight, at 40 C. 1 ug of rhGPC3 (from Creative Biomart) was used as positive control. The next day, peptides were discarded and plates were blocked with 100 μl of 5% non-fat milk in PBS. Then, the plates were washed with 300 μl/well of PBST (0.1% Tween20). Next, incubation with 100 uL/well of different antibody dilutions. This was followed by four washes with PBST. Then, incubation with 100 uL/well of anti-human IgG-HRP (From KPL) (1:2000 dilution). This was followed by four washes with PBST. Next, 100 uL/well of TMB (from Biolengend), incubation for 30 minutes. Then, 100 uL/well of 2N H2SO4. Lastly, OD450 nm was detected in an xMark™ Microplate Spectrophotometer (from BIO-RAD). If not indicated otherwise, incubations were performed for 1 hour at RT, and antibodies were diluted in 2% non-fat milk in PBS.

Results

Figure 4A:
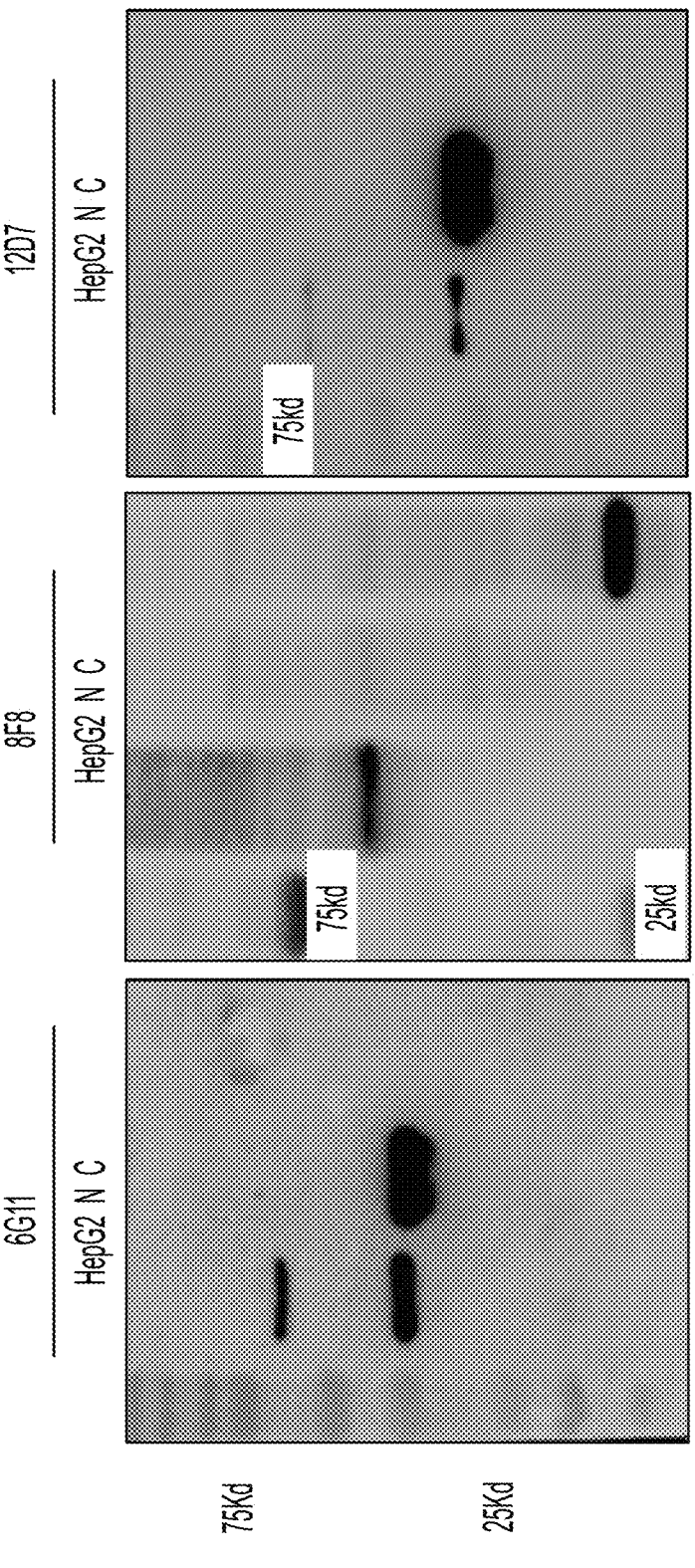
FIG. 4A shows West Blot analysis of the 293 cells transfected with hGPC3 N- or hGPC3 C-fragment.
Figure 4B:
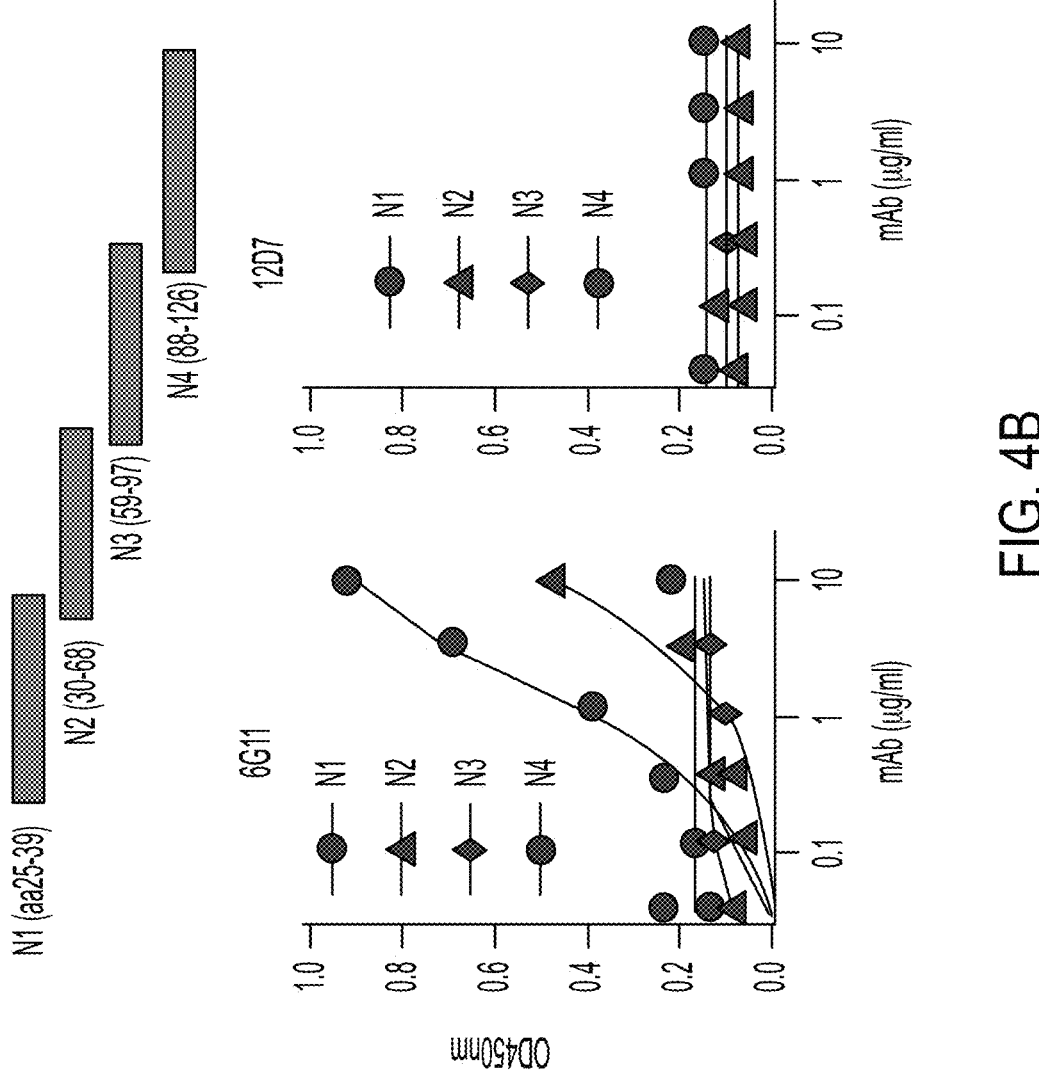
FIGS. 4B and 4C are shows graphs with data confirming that 6G11 and 12D7 bound to hGPC3 N-fragment and 8F8 bound to the hGPC3 C-fragment. HepG2 cell lysate was used as positive control. Mapping the 6G11 and 8F8 binding epitopes by overlapping peptides. The data showed 6G11 mAb bound to N1 peptide (AA25-39) (B) and 8F8 bound to C5 peptide (AA463-496).
Figure 4C:
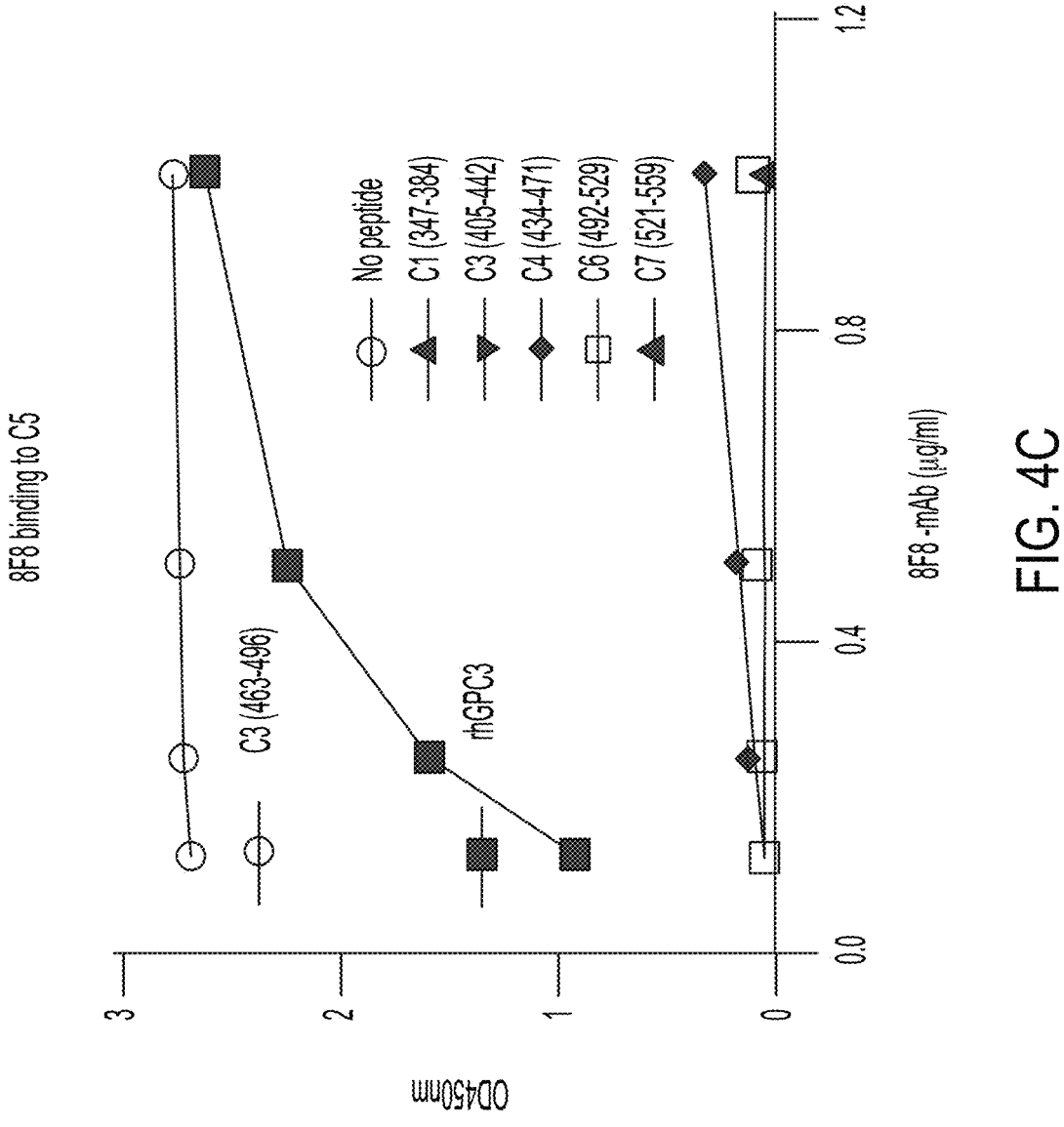
Figure 4D:
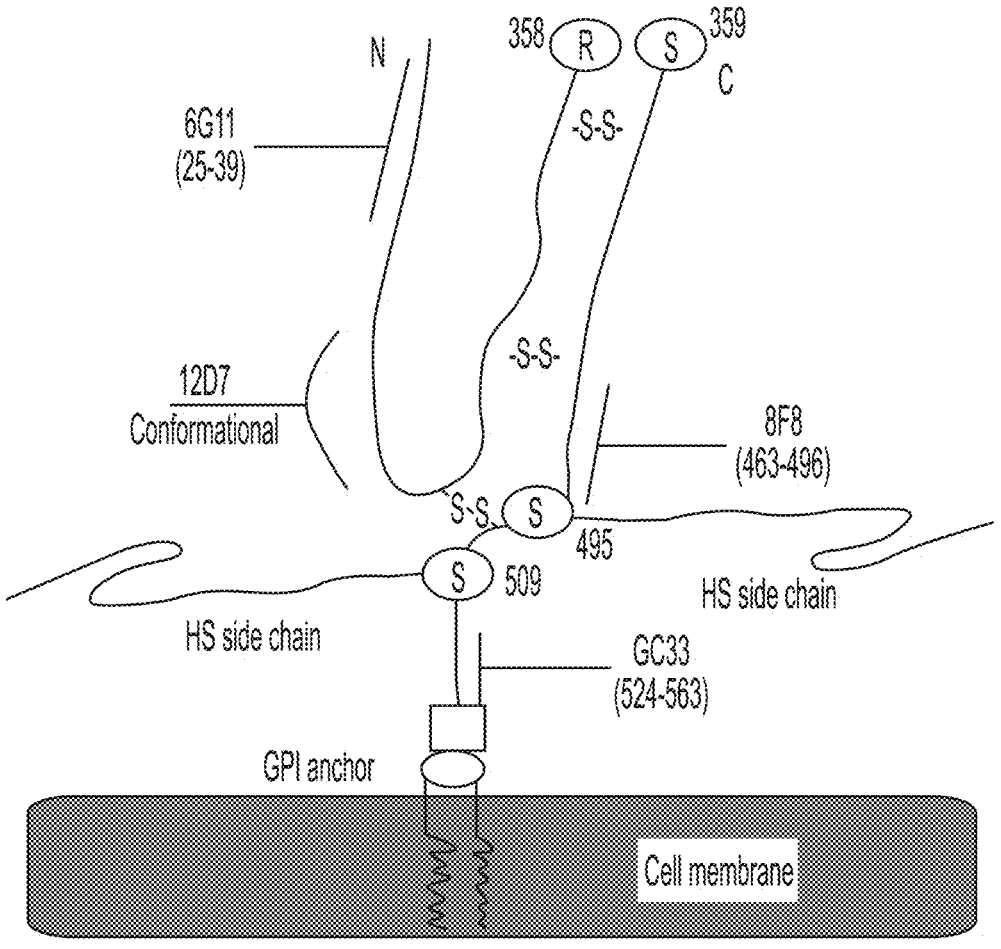
FIG. 4D is an illustration of the binding sites of mAbs on a schematic structure of hGPC3 derived from Haruyama and Kataoka (reference 25). As a reference, the GC33 mAb's epitope was indicated. The potential disulfide bonds between N-fragment and C-fragment of hGPC3 were also shown.

FIG. 1C shows that mAbs 6G11 and 12D7 bound to hGPC3 N-fragment (AA1-358), while the 8F8 bound to the hGPC3 C-fragment (AA359-580). To further map the mAb's epitopes, western blot analysis was constructed and confirmed that 6G11 and 12D7 mAbs bound hGPC3 N- and 8F8 bound hGPC3 C-fragment (FIG. 4A). Next, using overlapping synthetic peptides and ELISA assay, we determined that 6G11's epitope is AA25-39 of hGPC3 (FIG. 4B). By a similar strategy, the epitope for 8F8 was located in the AA463-496 of hGPC3 (FIG. 4C). However, no specific epitope was identified for 12D7. It is likely that 12D7 recognizes a conformational epitope in the hGPC3 N-fragment. The epitopes recognized by the mAbs are summarized and illustrated in FIG. 4D.

Example VI: Generation of CARTs

Materials and Methods

The second generation of CARs was constructed as follow. The CAR includes the leader sequence of human CD8 molecule, the VL and VH, a glycine and serine (GS) linker between the VL and VH, a fragment of CD8 hinge, the transmembrane domain of human CD28, and the 4-1BB and CD3 ξ chain signaling domains. The entire expression cassette was inserted behind the EF1α promoter in the lentivector (lv). Lentivector production was as described previously (4) by co-transfection of 293T cells with 4 plasmid DNA including the shuttle CAR expression shuttle plasmid, pLP1, pLP2 and pVSVG (Invitrogen). Virus particles in the media were concentrated by high speed centrifugation and sucrose gradient as previously described (4, 5). Virus titer was determined by transducing the Jurkat cells with a serial dilution of virus stock and anti-mouse Fab antibody staining (Jackson ImmunoReseach Lab).

Transduction of Human T Cells

Activation and transduction of primary human T cells were done as described (Zhu, W. et al., Hepatology 68: 574-89 (2018)). Briefly, human T cells were isolated from the buffy coat of healthy donors by negative selection (Stemcell Technologies, Inc) and activated by Dynabeads (Fisher Scientific) for 24 hrs. The activated T cells were transduced with lv at 20-40 MOI. The beads were removed 24 hrs after another 24 hours. Forty units of interleukin-2 (IL-2) were added to the RPMI medium every 3 days through the process.

Results

Figures 5A, 5B:
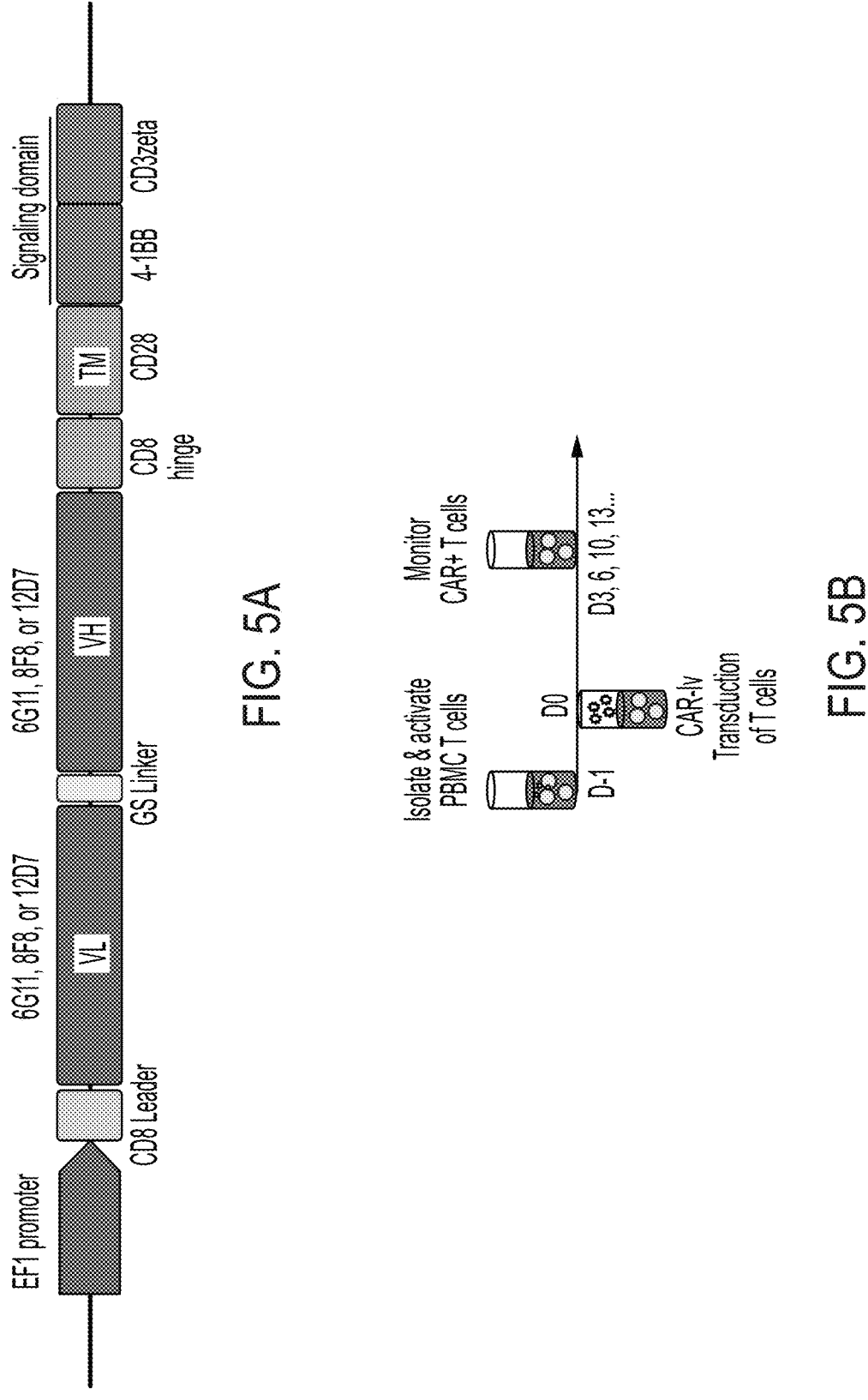
FIG. 5A shows the schematic structure of the second generation CAR-Ts built from 6G11, 8F8, and 12D7 was illustrated. GS linker: glycine-serine linker; TM:transmembrane domain of CD28.
FIG. 5B is an illustration of the experimental procedure. Human T cells were isolated from PBMC and activated by CD3/CD28 beads for 24 hrs. On day 0, T cells were transduced with lv and CAR expression was monitored from day 3-13.
Figure 5C:
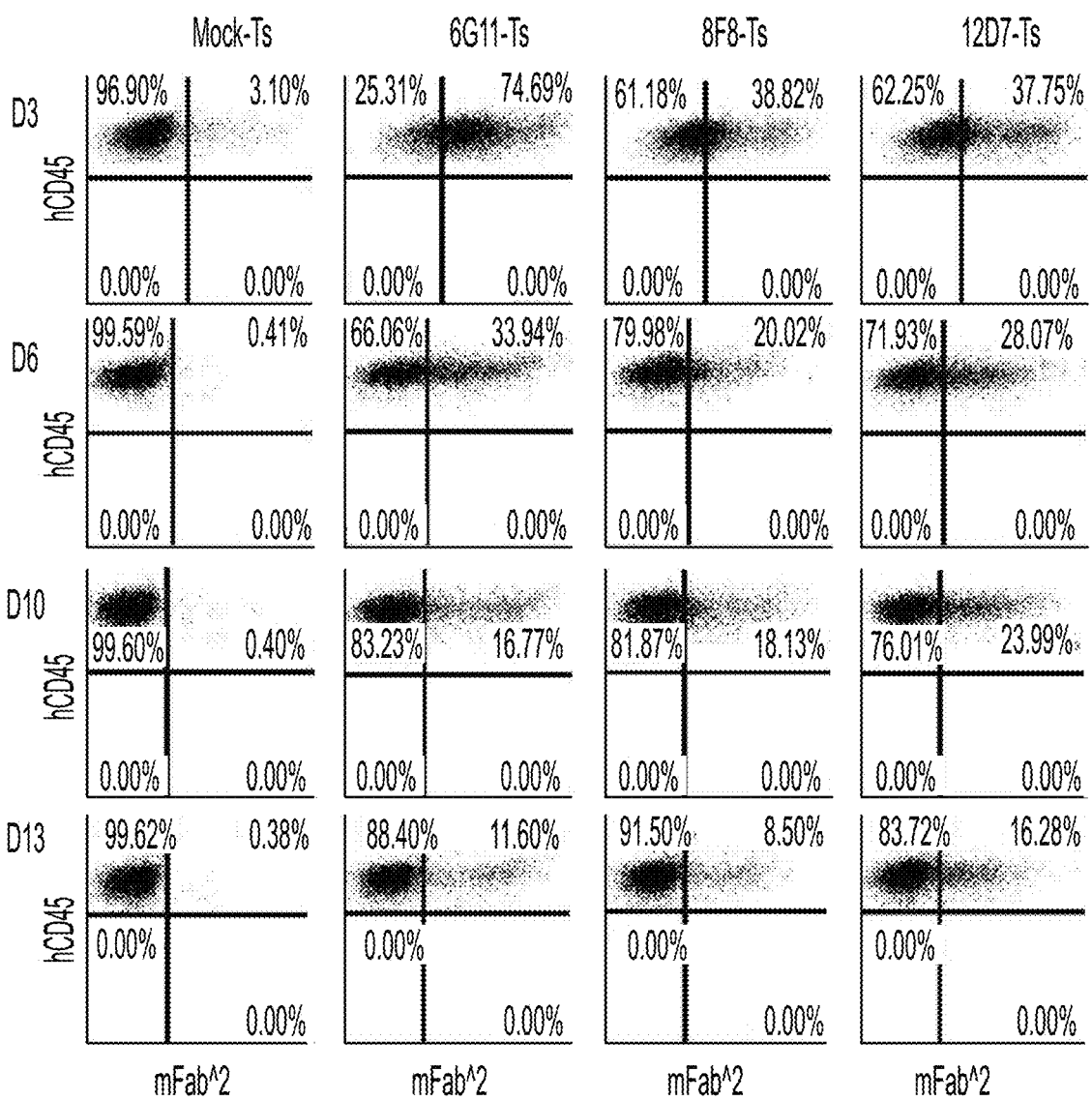
FIG. 5C is a panel of dot plots after CAR gene transduction at different time points were presented. CAR expression was detected by anti-mouse Fab antibody at indicated time points. This experiment was repeated at least 5 time with similar observations.

The second generation of CARTs was built using the cDNA sequences of 6G11, 8F8, and 12D7 mAbs. The CAR comprises a single-chain variable fragment derived of the mAbs, preceded by a CD8a leader peptide, followed by a CD28 transmembrane domain, linked to 41-BB and CD3 ξ intracellular signaling domains (FIG. 5A). The lentivectors expressing the CAR genes were used to transduce human primary T cells (FIG. 5B). All three CAR-expressing len-tivectors could effectively transduce primary human T cells (FIG. 5C). Three days after transduction, the 6G11, 8F8, and 12D7 CAR+ T cells were approximately 75%, 40%, and 40% of total T cells, respectively. However, the CAR expression on T cells was unstable. The % of CAR+ T cells gradually decreased and became stable when reaching 10-15% expression on day 13 after transduction (FIG. 5C). It was also found that CARs on T cells were capable of binding soluble hGPC3 protein (Supplementary FIG. 5C). The data showed that soluble hGPC3 could stain ~90% of 6G11 CARTs, but only ~40% of 8F8 and 12D7 CARTs. These data suggest that 6G11's epitope and 6G11 CAR are more accessible to each other.

Example VII: CARTs Expansion in Response to HepG2 Tumor Cell Stimulation, but with Significant Different Effector Function

Materials and Methods

Flow Cytometry Analysis

The following antibodies were used in the staining: anti-human CD45, anti-mouse CD45, anti-mouse Fab, hGPC3 protein. Cells were stained with indicated antibodies and analyzed on LSR flow cytometer. Goat anti-mouse Fab antibody (Jackson ImmunoReseach Lab) and FITC-labeled hGPC3 were used to determine CAR transduction and the binding of CAR to cognate antigen.

Results

Figure 6A:
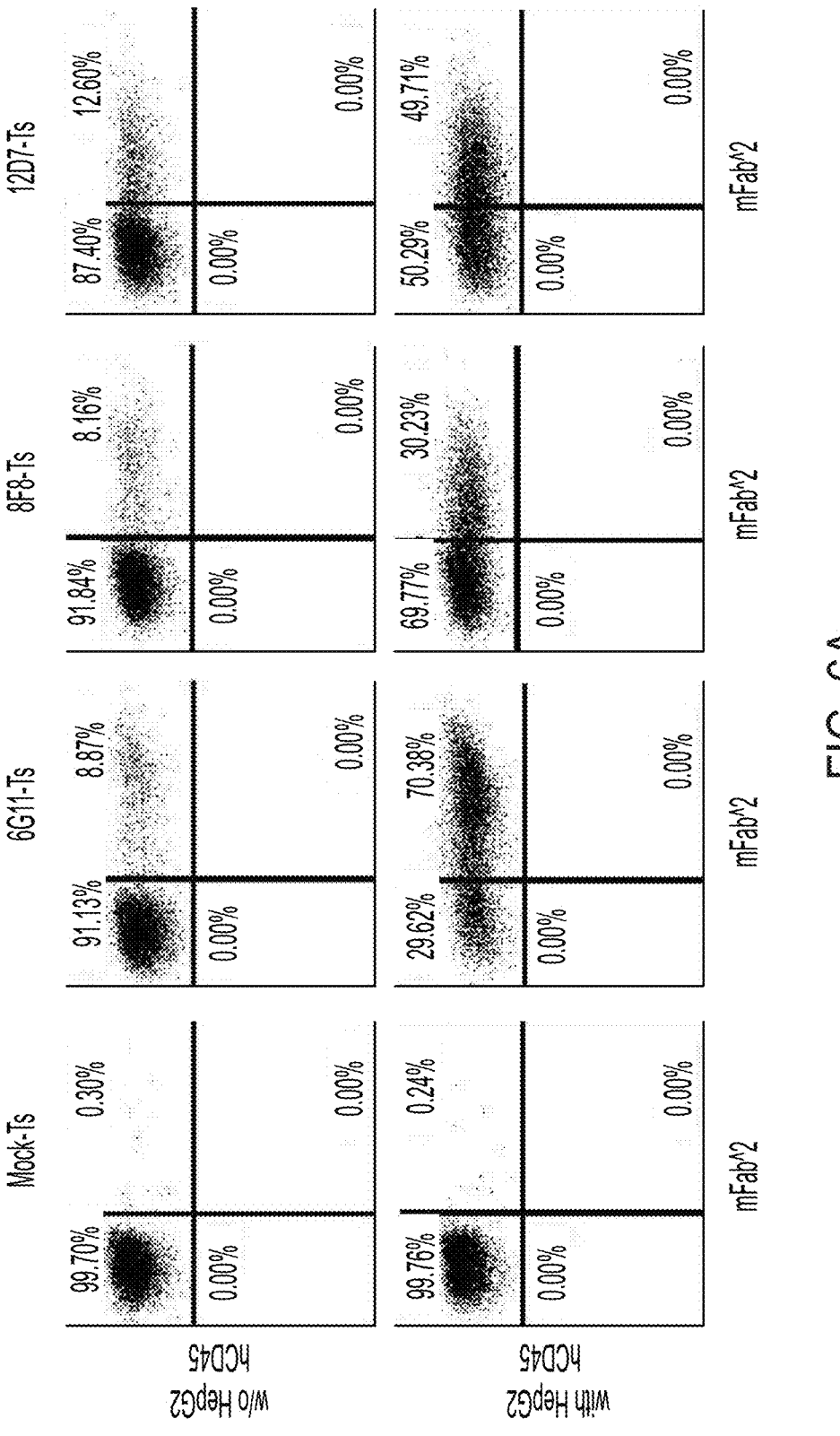
FIGS. 6A-6D show responsiveness of CAR-Ts to HCC tumor cell stimulation. CARTs were generated as described in FIG. 5. On Day 14 after transduction, CARTs were co-cultured with or without HepG2 tumor cell. The % of CAR+ T cells and their effector function were examined after 6 days.
Figure 6B:
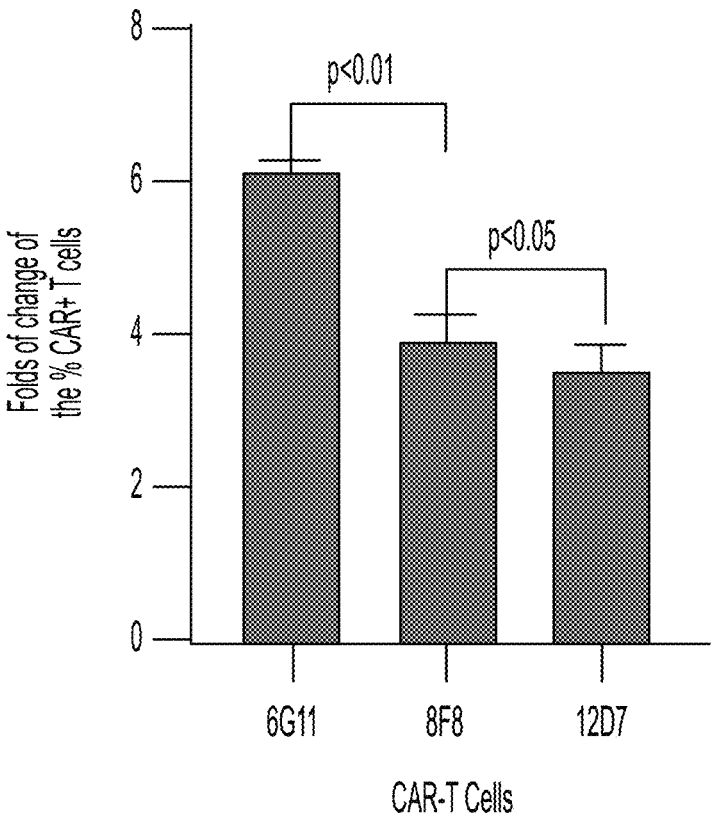
Figure 6C:
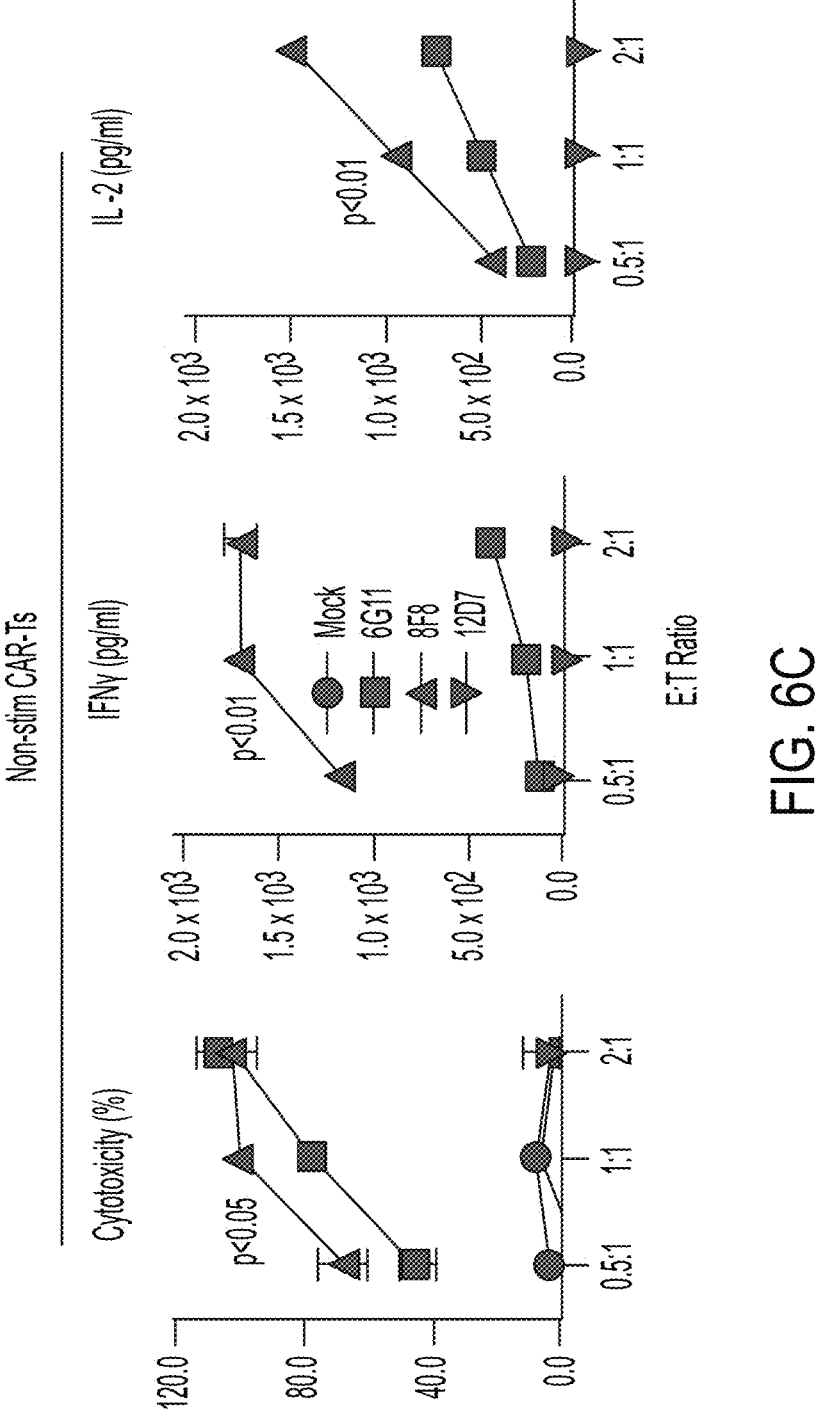
Figure 6D:
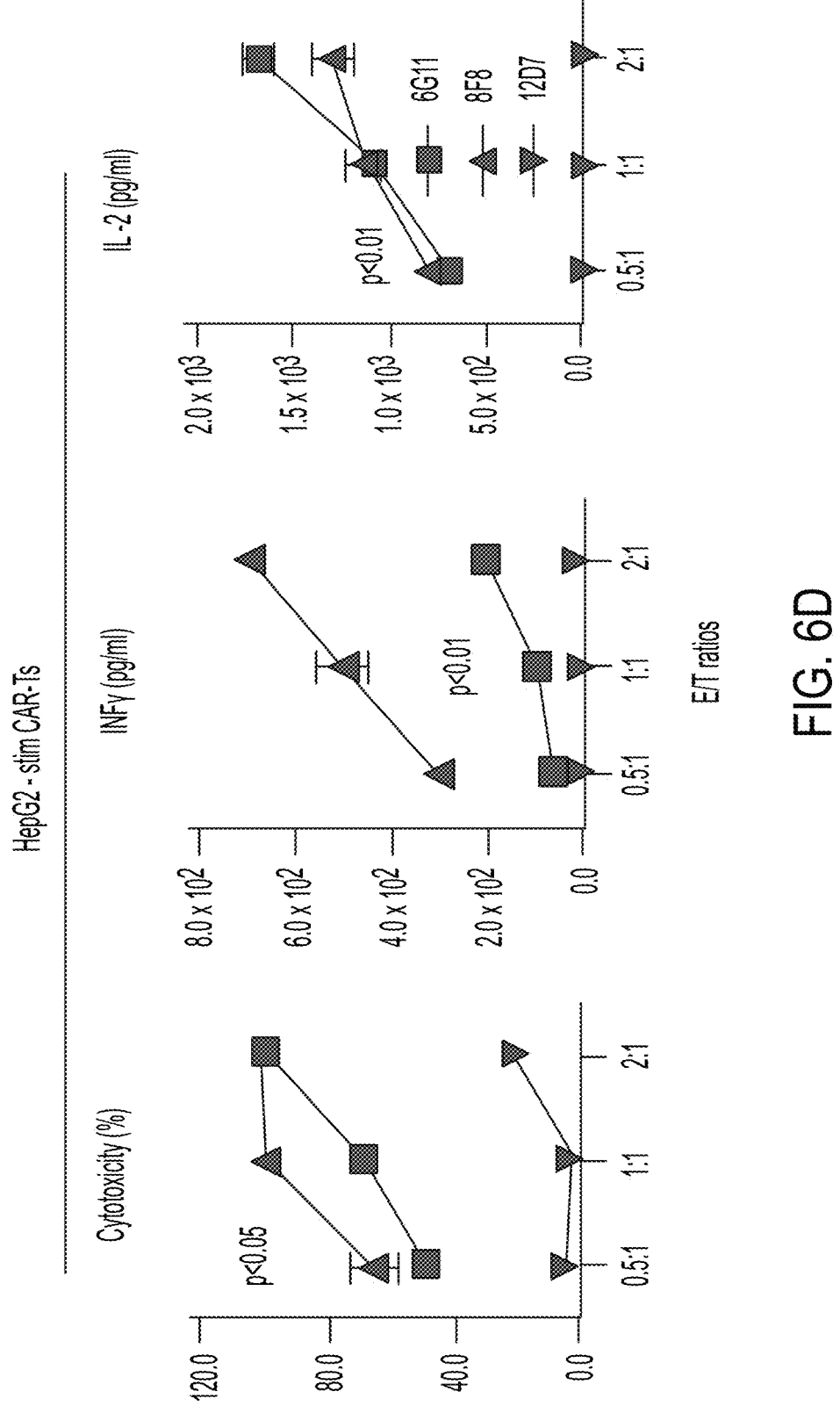

The responsiveness of CARTs to HCC tumor cells was studied. The data showed that all 3 CARTs could respond to HepG2 cell stimulation and undergo expansion (FIG. 6A-B). 6 days after HepG2 stimulation, the CAR+ T cells had increased from ~10% to as high as 70%. In fact, the % of 6G11 CAR+ Ts increased by 6 folds, and the % of 8F8 and 12D7 CAR+ Ts increased by ~4 folds. However, their effector functions were significantly different. The 8F8 CARTs generated the strongest cytotoxicity against HepG2, and produced the highest amount of IFNγ and IL2 (FIG. 6C). Albeit slightly weaker than 8F8 CARTs, the 6G11 CART also possessed potent cytotoxicity, but its cytokine produc-tion, especially IFNγ, was significantly lower than 8F8 CARTs. On the other hand, 12D7 CARTs has the weakest effector function with undetectable cytotoxicity and cyto-kine production (FIG. 6C). Importantly, following 6 days of antigen (HepG2 cell) stimulation, the 8F8 and 6G11 CARTs maintained their strong cytotoxicity and cytokine production (FIG. 6D). The IL2 production by 6G11 and 8F8 CARTs was enhanced after HepG2 stimulation. In contrast, even though 12D7 CARTs could be expanded by HepG2 cell stimulation (FIG. 6A-B), their cytokine production remained undetect-able. However, after 6-day HepG2 stimulation, 12D7

Figures 6E, 6F, 6G:
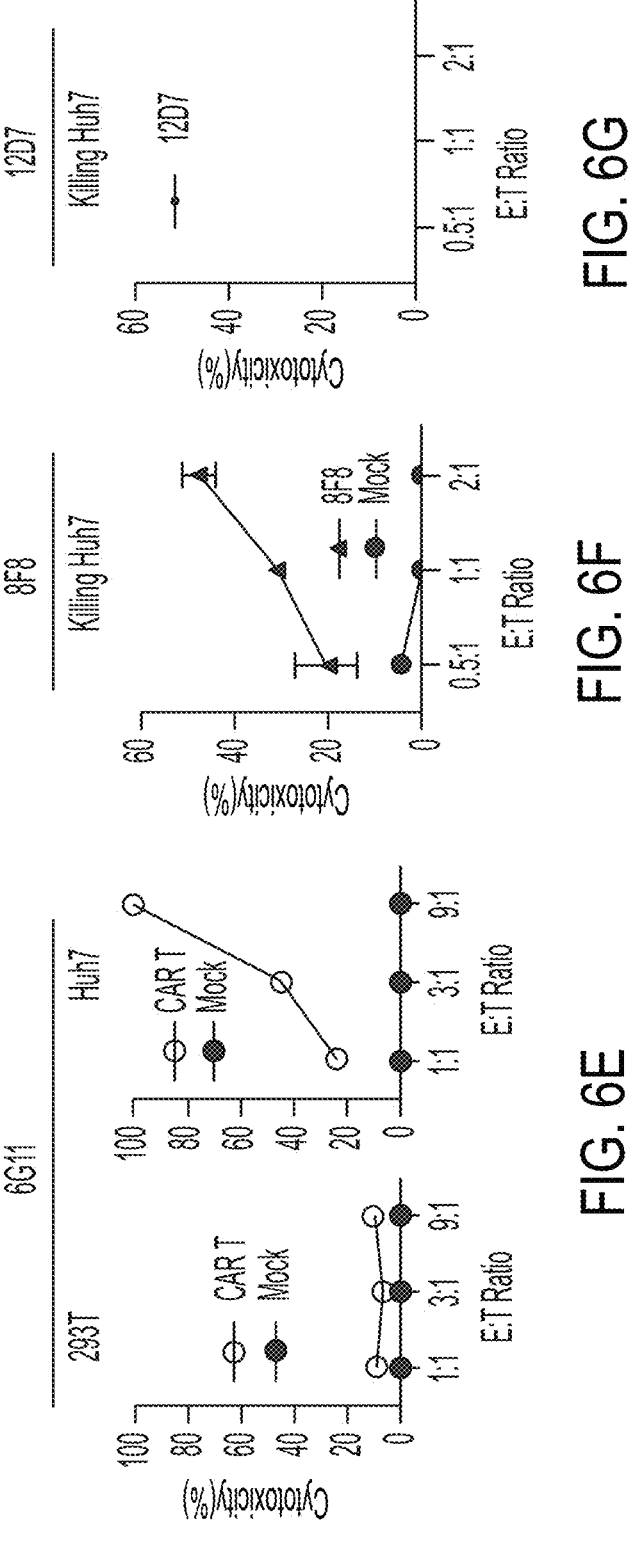
FIG. 6E-6G show the cytotoxicity of CARTs on Huh7 tumor cells.

CARTs did generate a low level of cytotoxicity (FIG. 6D). Furthermore, the 8F8 and 6G11 CARTs showed significant killing on the GPC3$^{low}$ Huh7 cells (FIGS. 6E-6G). Again, the 12D7 CARTs were unable to kill Huh7 tumor cells.

Example VIII: Soluble hGPC3 does not Activate CARTs, Nor Block CART's Activation by HCC Tumor Cells

Materials and Methods

LDH Assay and Cytokine ELISA Assay

HepG2 cells (5×103/well) were grown overnight on flat-bottom 96-well plates. CARTs were added at indicated effector to target cell ratios without addition of exogenous cytokines. After overnight co-culture, the cytotoxicity and effector cytokines of CARTs were measured by the lactate dehydrogenase (LDH) activity as indicated by the provider (Promega) and by ELISA (Biolegend).

Results

Figure 7A:
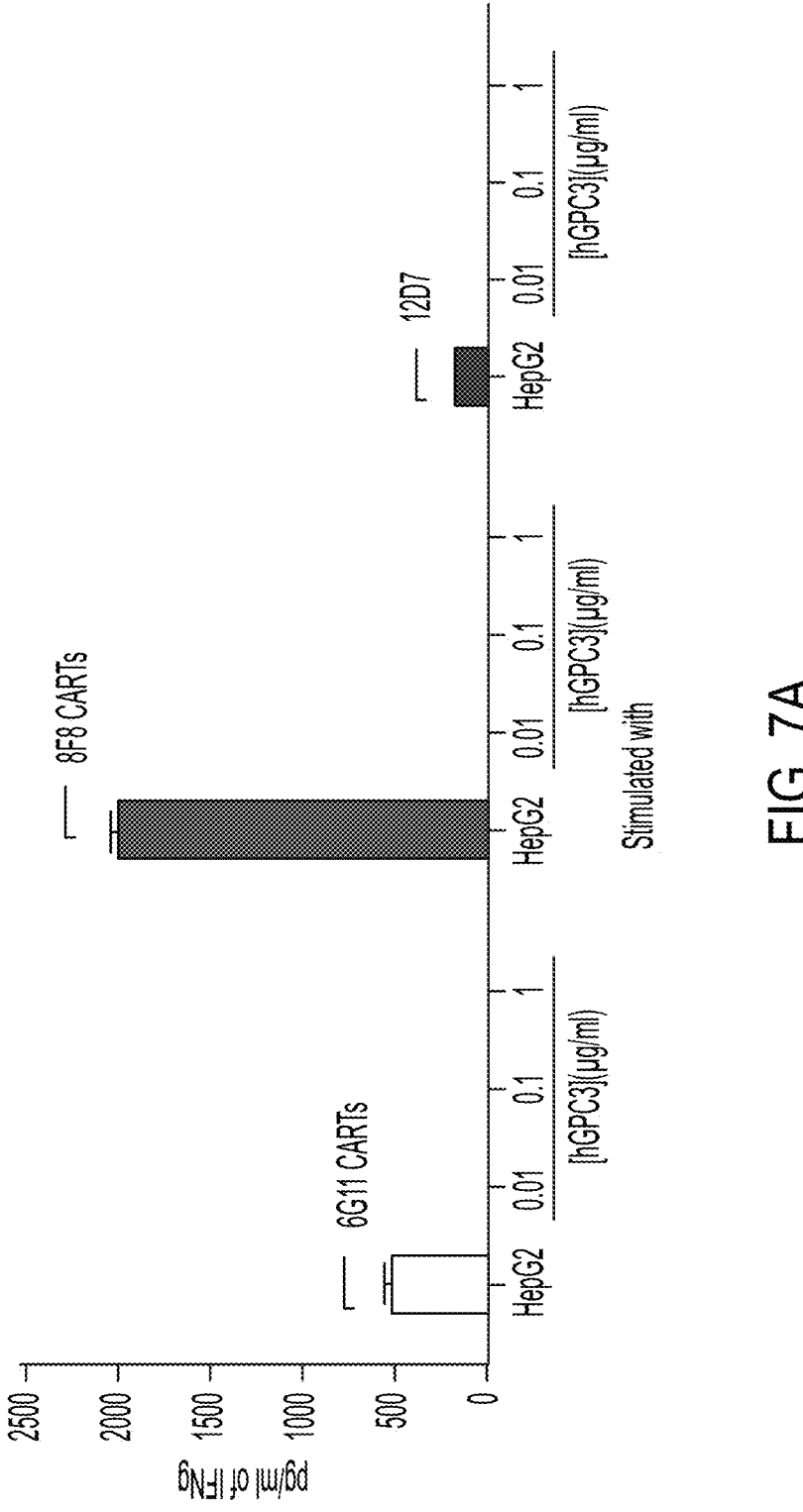
FIG. 7A-7C show soluble hGPC3 did not activate CARTs nor inhibit CART activation by HepG2.
Figure 7B:
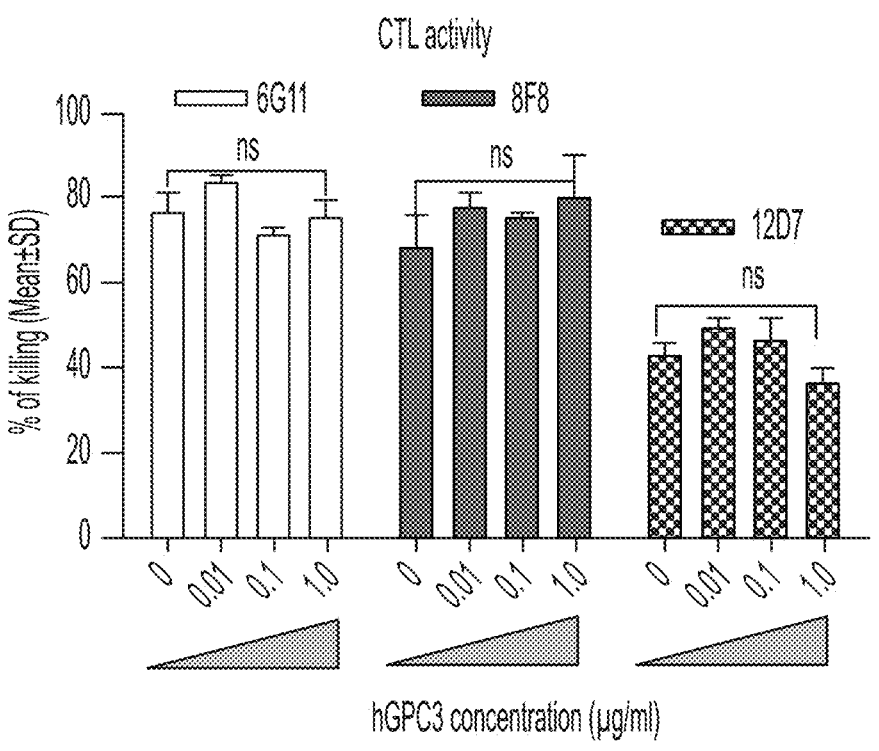
Figure 7C:
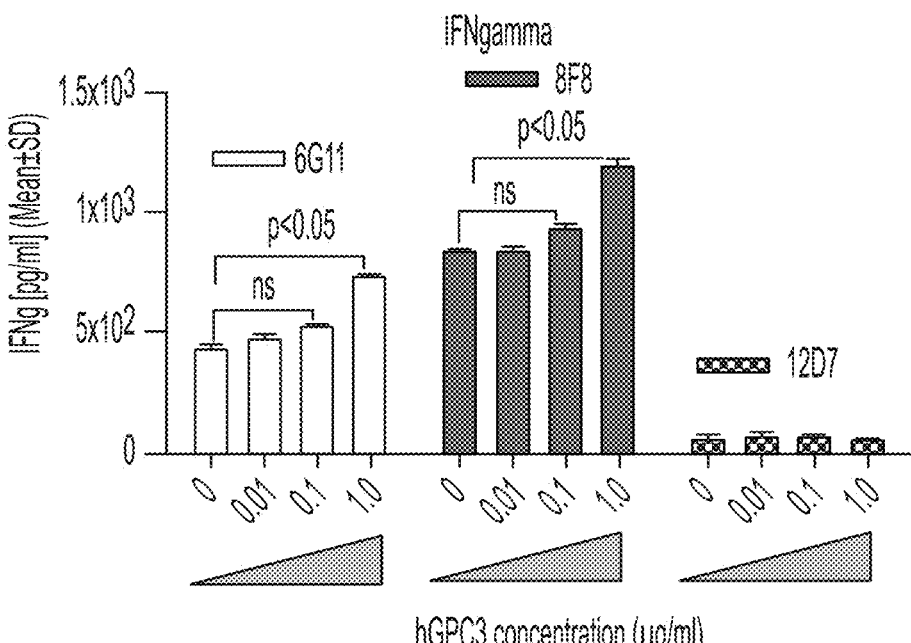

HCC patients normally have an elevated level of soluble GPC3 in their serum. Here, we investigated whether the CARTs would be activated by soluble GPC3 and whether the recognition and killing of HCC tumor cells could be blocked by the presence of soluble hGPC3. For this, we seeded 5×10$^3$ HepG2 cells on flat-bottom 96-well plates. The next day, CARTs with different concentrations of hGPC3 were added. CARTs plus soluble hGPC3 without HepG2 cells were used detect activation of the CARTs by the soluble protein alone. Our data showed that soluble hGPC3 did not activate CARTs (FIG. 7A), and that it did not affect the killing of HepG2 tumor cells by the CARTs (FIG. 7B). The cytokine production of CARTs in co-culture with HepG2 cells was not inhibited by low concentration of hGPC3 (0.01-0.1 μg/ml). However, a high concentration of soluble hGPC3 (1 μg/ml) modestly enhanced the HepG2-induced IFNγ production by CARTs (FIG. 7C).

Example IX: Adoptive Transfer of CARTs Eliminates HepG2 Tumor Xenografts in NSG Mice

Materials and Methods

Tumors and Adoptive Cell Transfer

HepG2 tumor xenografts were established as recently reported (Zhu, W., et al.). Two and half million (or 5 million) of HepG2 tumor cells were inoculated onto the shaved flank of NSG mice. Seven days later, CARTs with indicated numbers were transferred into the tumor-bearing NSG mice. Tumor growth was monitored by measuring the length, width, and height of the tumors. Tumor volume was calcu-lated as ½(length×width×height). CARTs in mouse blood were monitored by collecting tail vein blood and performing immunological staining with anti-human CD45 and anti-mouse Fab antibodies. Co-staining of the mouse CD45 cells was used as internal reference to estimate the change of human CD45+ cells.

Results

Figure 8A:
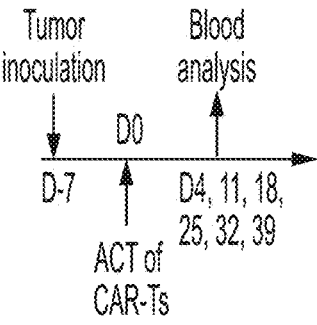
FIG. 8A-8F show adoptive transfer of CARTs generated potent antitumor effects correlating to CAR expansion in vivo.
Figure 8B:
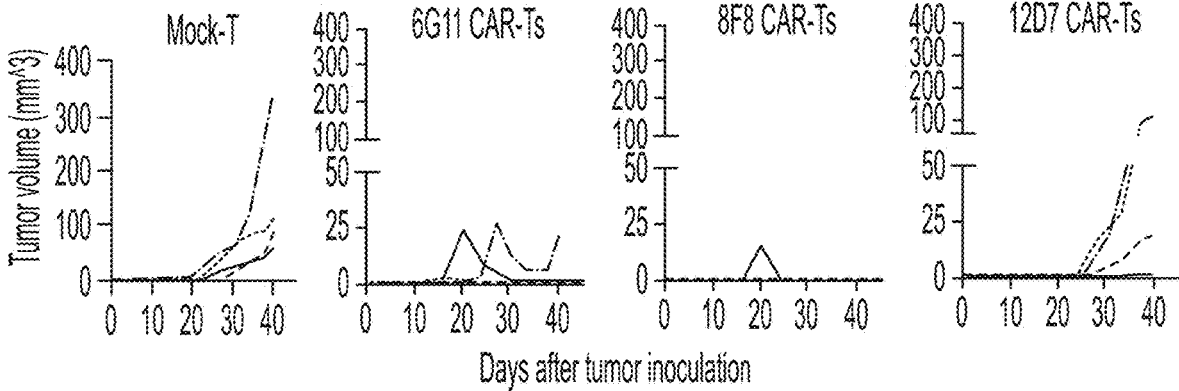

To study the in vivo antitumor effects of CARTs, NSG mice bearing the HepG2 xenografts were adoptively trans-ferred with CARTs. The tumor growth and the expansion and persistence of CARTs in NSG mouse blood were monitored (FIG. 8A). In the first in vivo experiment, HCC tumors were established by subcutaneous inoculation of 2.5 million HepG2 cells. 7 days later, mice were treated with 3 million of CARTs. Our data showed that, compared to the non-transduced Mock-Ts, all CARTs generated significant antitumor effects (FIG. 8B). Both 6G11 and 8F8 CARTs could eventually eradicate the tumors even though some tumors may experience transient growing (FIGS. 8B and 8F). 12D7 CARTs delayed and inhibited tumor growth, but did not eradicate the tumors (FIGS. 8B and 8F). In the second experiment, we doubled the number of HepG2 cells to 5 million for tumor inoculation. 7 days later, the tumor bearing mice were treated with the same dose of 3 million CARTs. We found that while 8F8 CARTs were still able to eradicate more than 90% of the tumors, 6G11 CARTs achieved complete eradication in only 20% of the mice (FIG. 8G). Increase of 6G11 CARTs dose to 10 million resulted in complete tumor eradication in ~90% of treated mice (Table 2). Thus, adoptive transfer of 1.2-2 fold of 6G11CARTs (compared to the number of inoculated HepG2 cells) can result in complete eradication of HCC tumors in 75-90% of treated mice. The 8F8 CARTs are significantly more effective and result in complete eradication in more than 90% of the mice even when 0.6 fold of 8F8 CARTs are transferred. Table 2 summarizes the antitumor effects of 5 in vivo experiments. These in vivo antitumor effect data are in agreement with the in vitro data (FIG. 6), which showed that 8F8 CARTs generated the strongest cytotoxicity and cytokine production, while 12D7 CARTs had the weakest effector function.

TABLE 2

| Groups | No. of Tumor cells | No. of CARTs | Ratios of CART/ Tumor cells | Tumor free/ Total Tumors | % of tumor free |
|---|---|---|---|---|---|
| 6G11 | $5 \times 10^6$ | $10 \times 10^6$ | 2 | 7/8 | 87.5 |
| | $2.5 \times 10^6$ | $3 \times 10^6$ | 1.2 | 3/4 | 75 |
| | $5 \times 10^6$ | $3 \times 10^6$ | 0.6 | 1/5 | 20 |
| 8F8 | $2.5 \times 10^6$ | $3 \times 10^6$ | 1.2 | 4/4 | 100 |
| | $5 \times 10^6$ | $3 \times 10^6$ | 0.6 | 14/15 | 93 |
| 12D7 | $2.5 \times 10^6$ | $3 \times 10^6$ | 1.2 | 0/4 | 0 |
| | $5 \times 10^6$ | $3 \times 10^6$ | 0.6 | 0/5 | 0 |

Figure 8C:
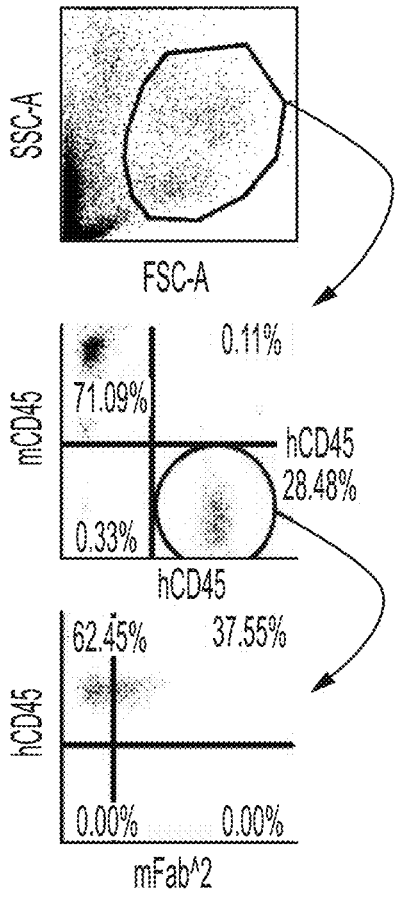
Figure 8D:
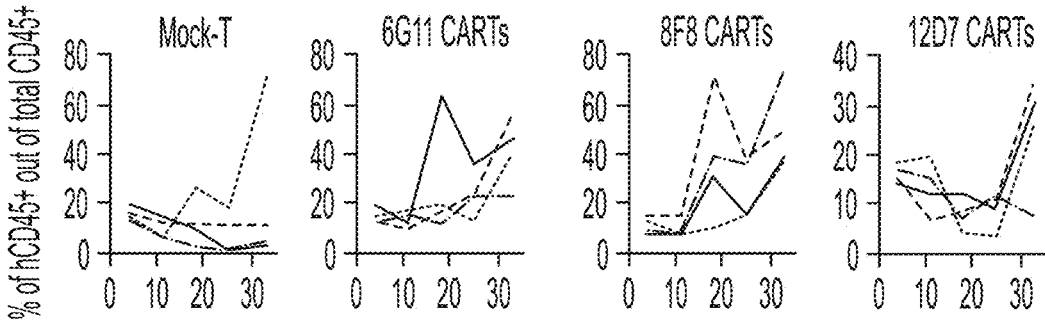
Figure 8E:
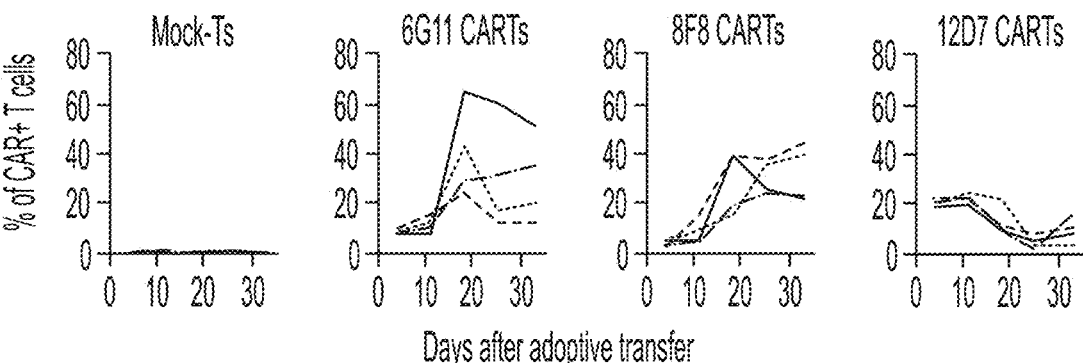
Figure 8F:
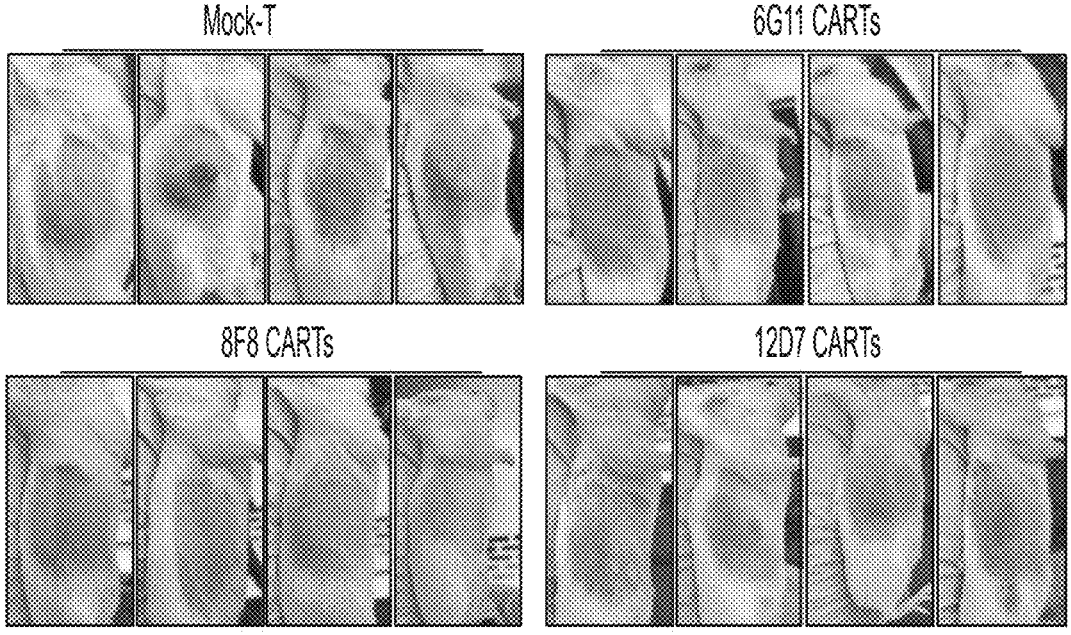
Figure 8G:
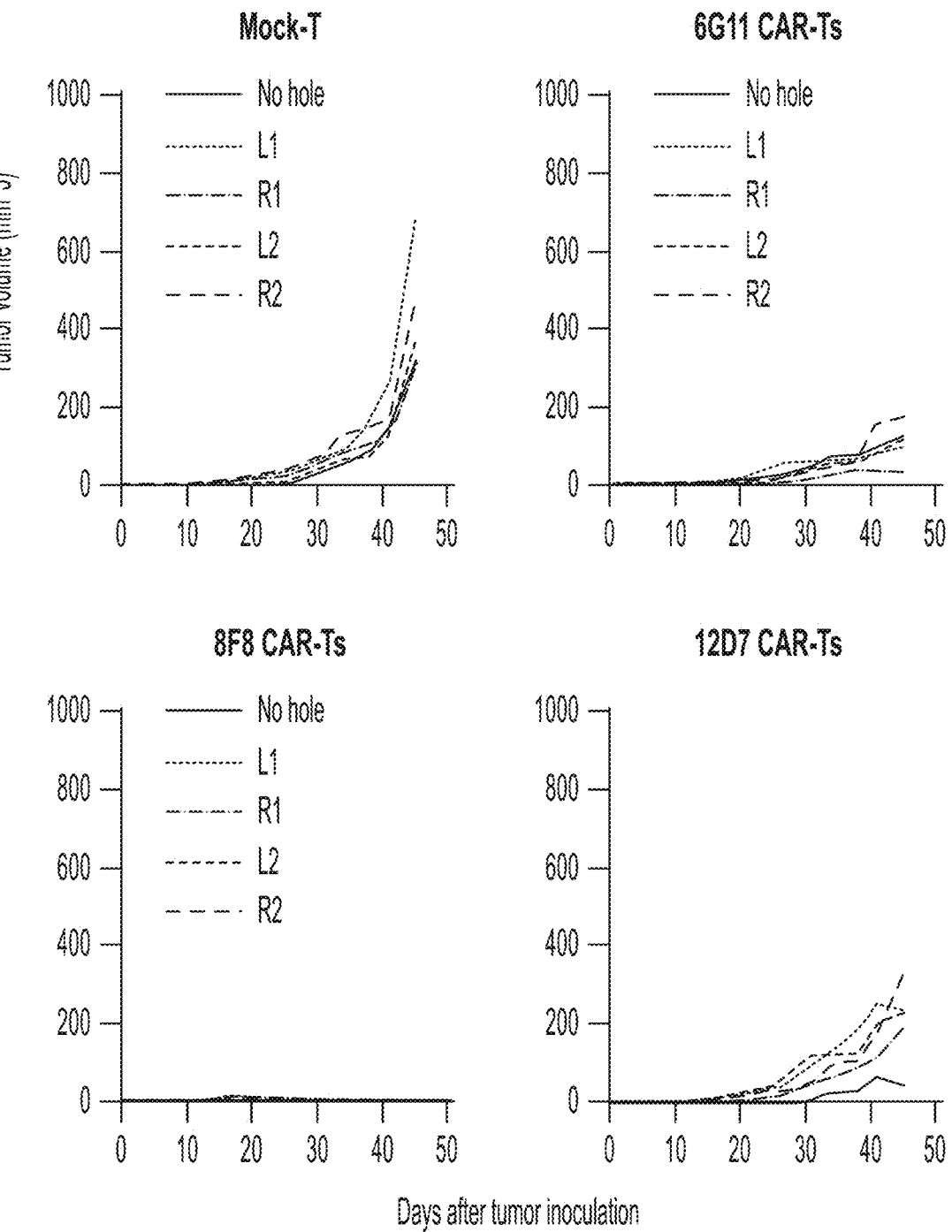
FIG. 8G are graphs showing the antitumor effect of CARTs when a lower effector/tumor load (0.6 CARTs vs 1 HepG2 tumor cells) was used. HCC xenografts were established with 5 million HepG2 tumor cells inoculation. Seven days later, 3 millions of CARTs were adoptively transferred into the tumor bearing mice. Even at the lower E/T ratio of 0.6, all CARTs generated significant inhibition of tumor growth. However, only the 8F8 CAR-Ts were able to completely eradicate HCC tumor xenografts. In contrast, only 20% of 6G11 CART treated mice were tumor free.
Figure 9:
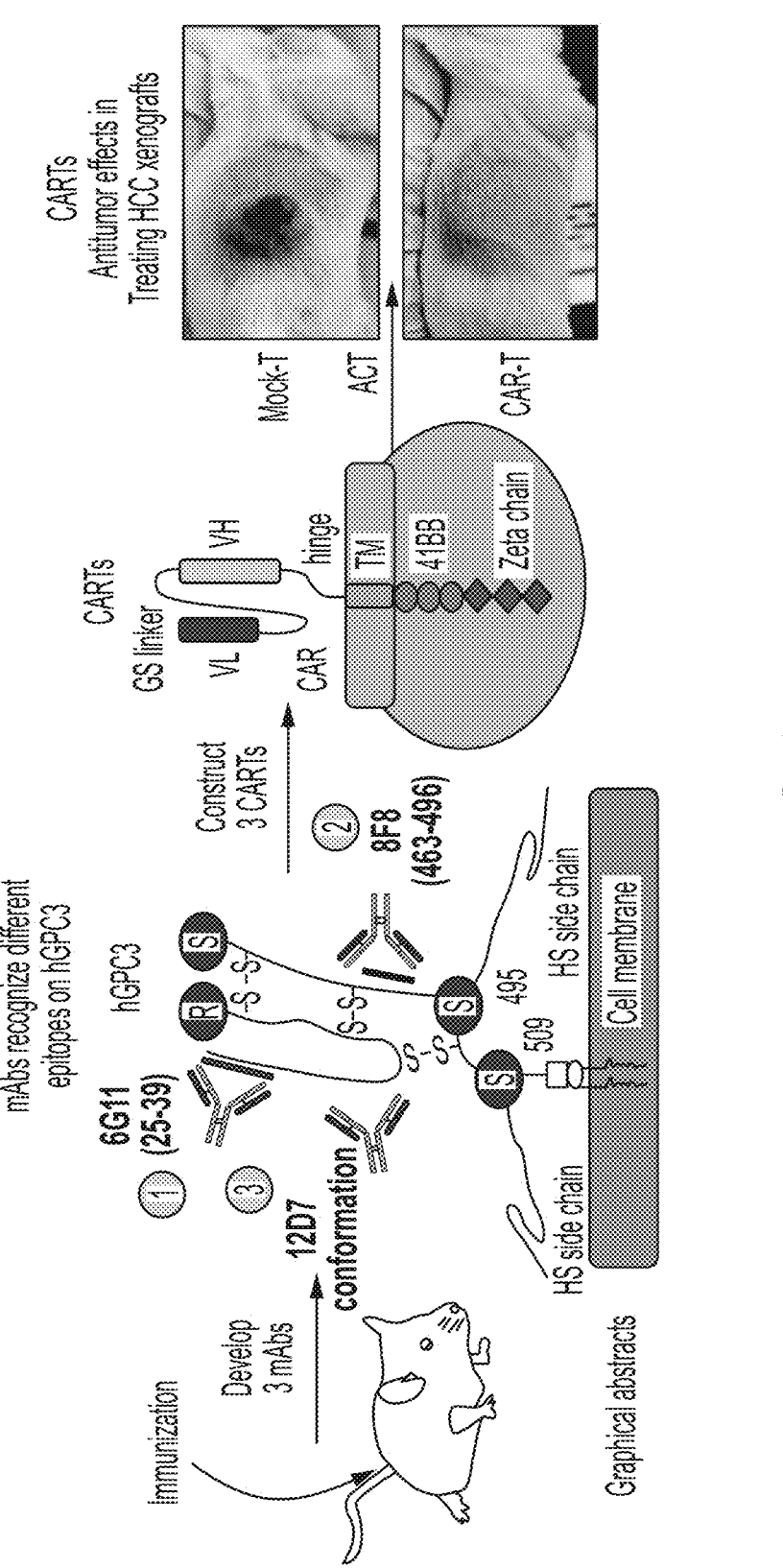
FIG. 9 is an illustration showing development and administration of CARTs.
Figure 10:
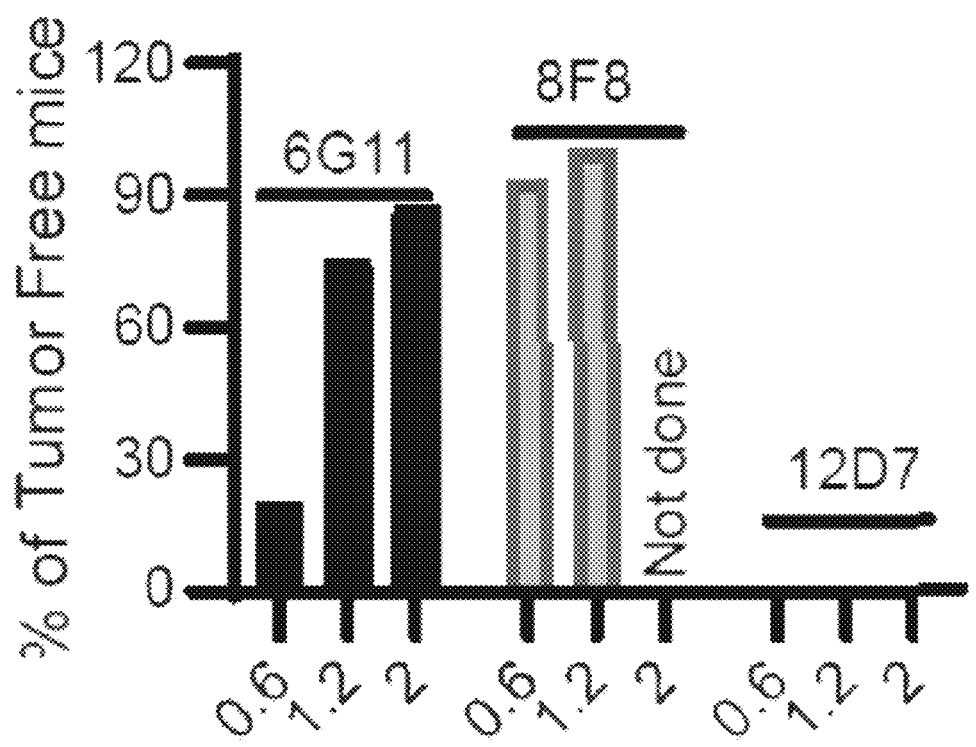
FIG. 10 is a graph showing the summary of antitumor effects of the indicated CARTs.
Figure 11A:
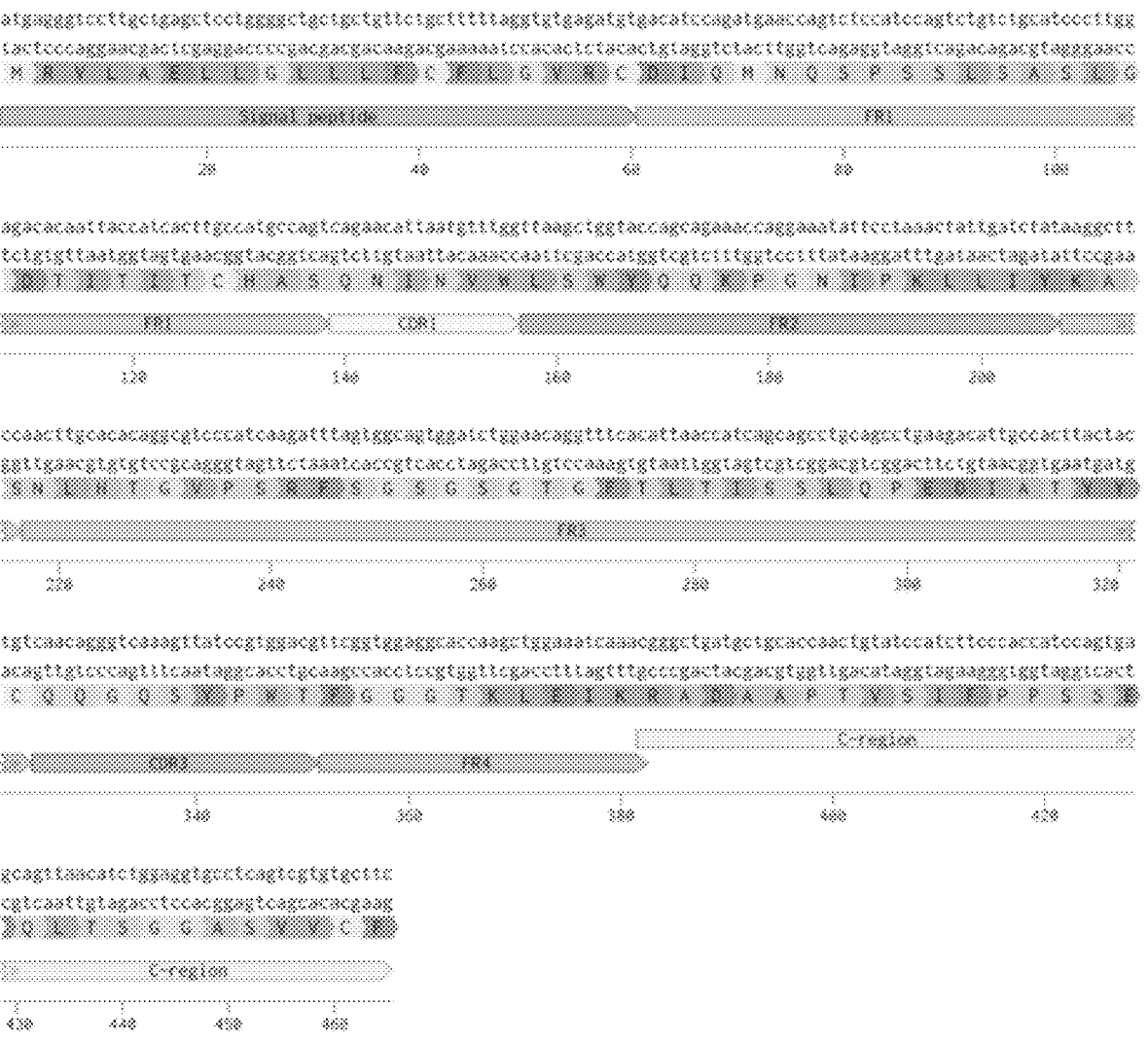
FIGS. 11A-11F show the nucleotide sequences of the 6G11 (FIGS. 11A-11B), 8F8 (FIGS. 11C-11D), and 12D7 (FIGS. 11E-11F) variable region of light chain (VL) and heavy chain (VH) of monoclonal antibodies (mAbs), respectively in order of appearance.
Figure 11B:
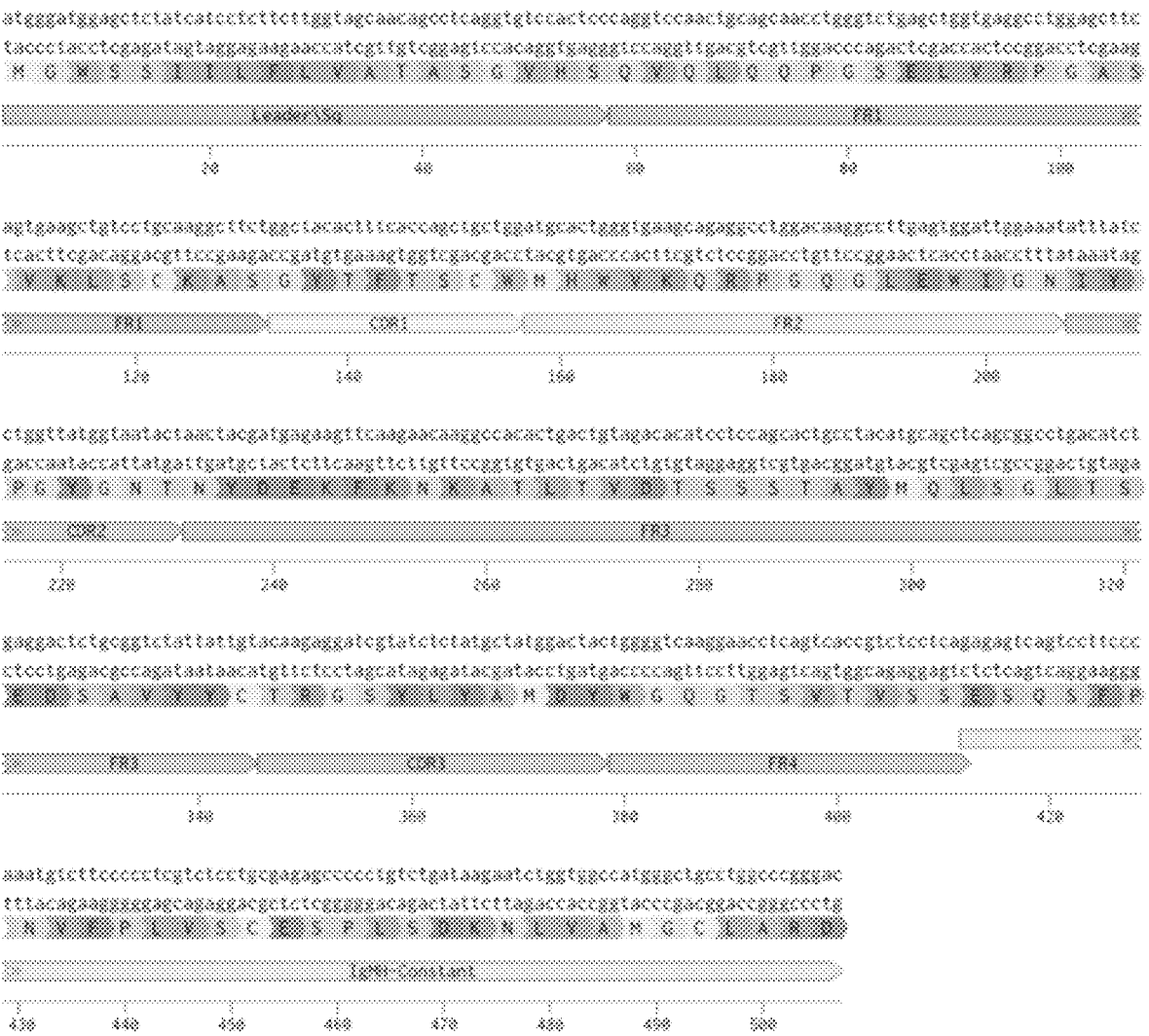
Figure 11C:
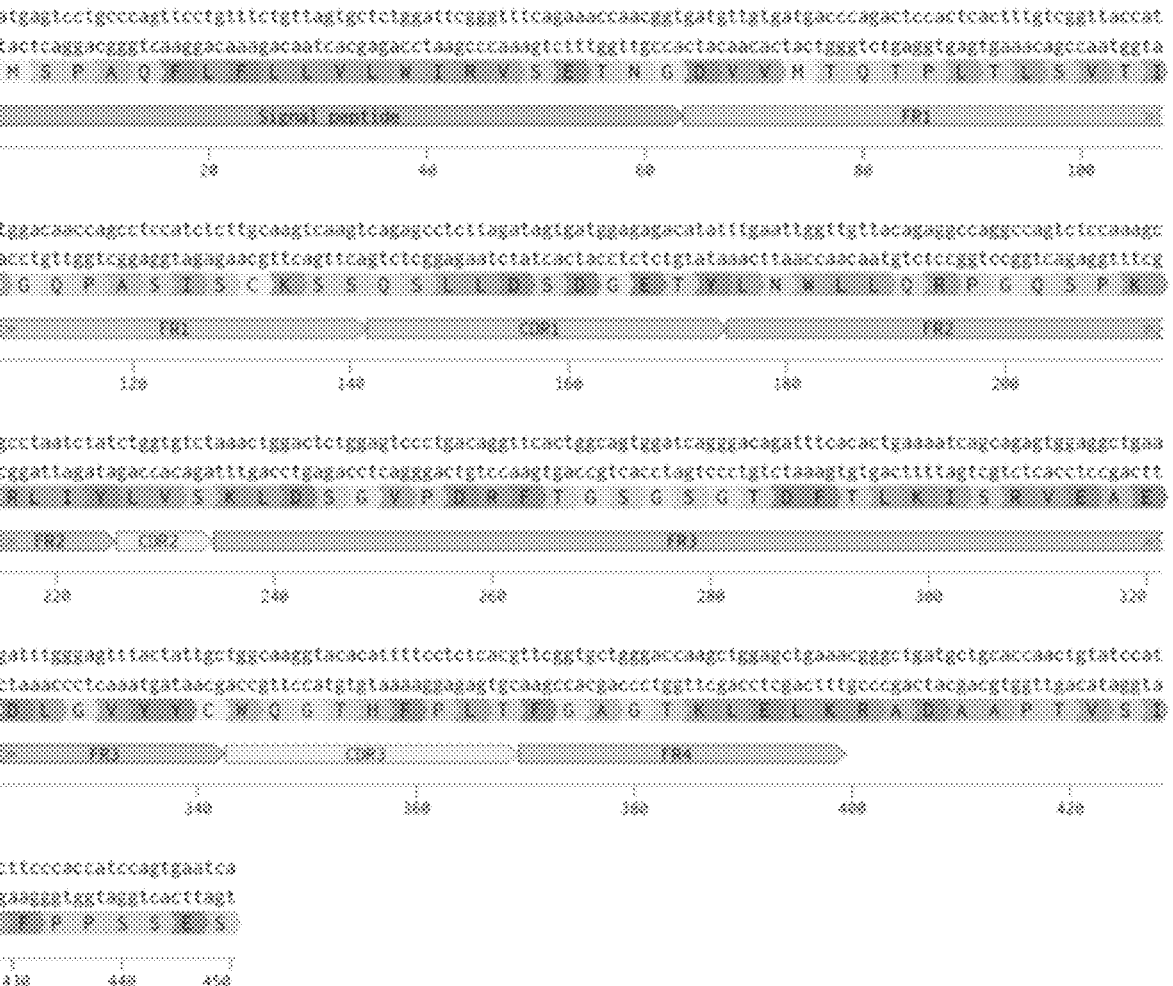
Figure 11D:
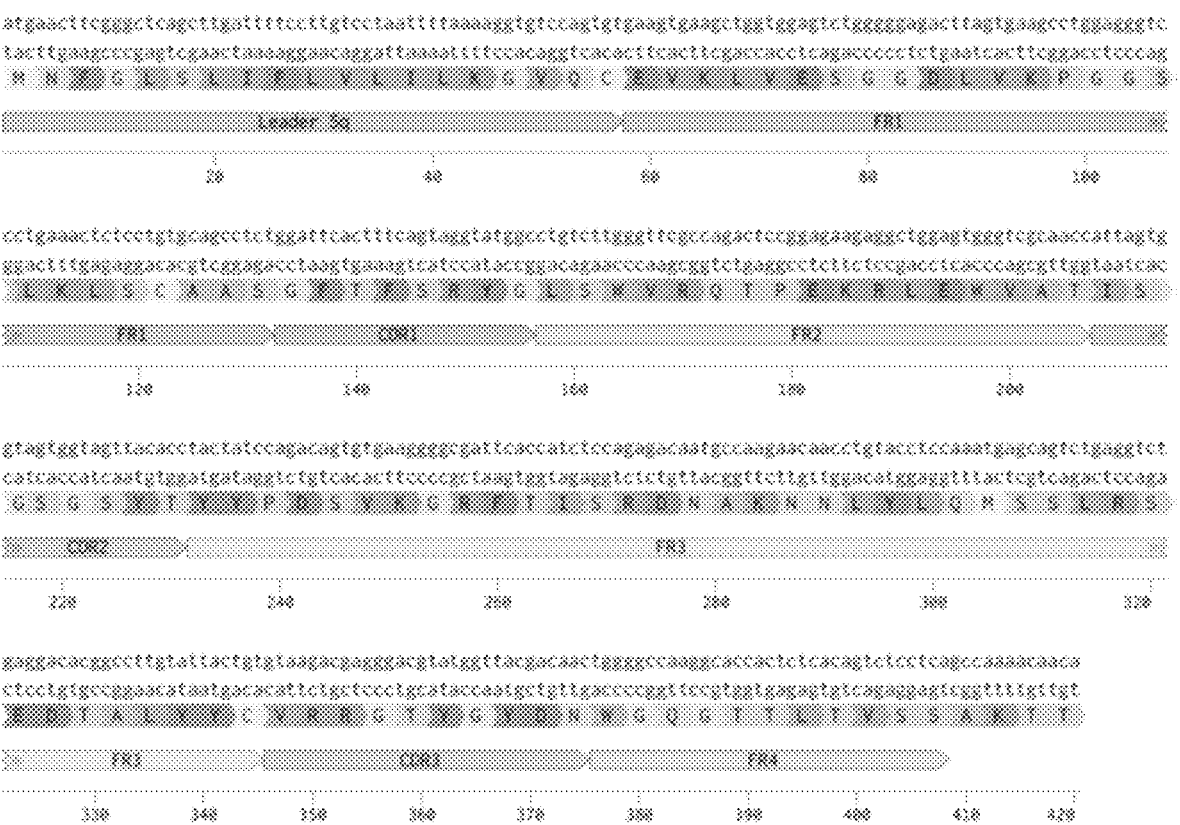
Figure 11E:
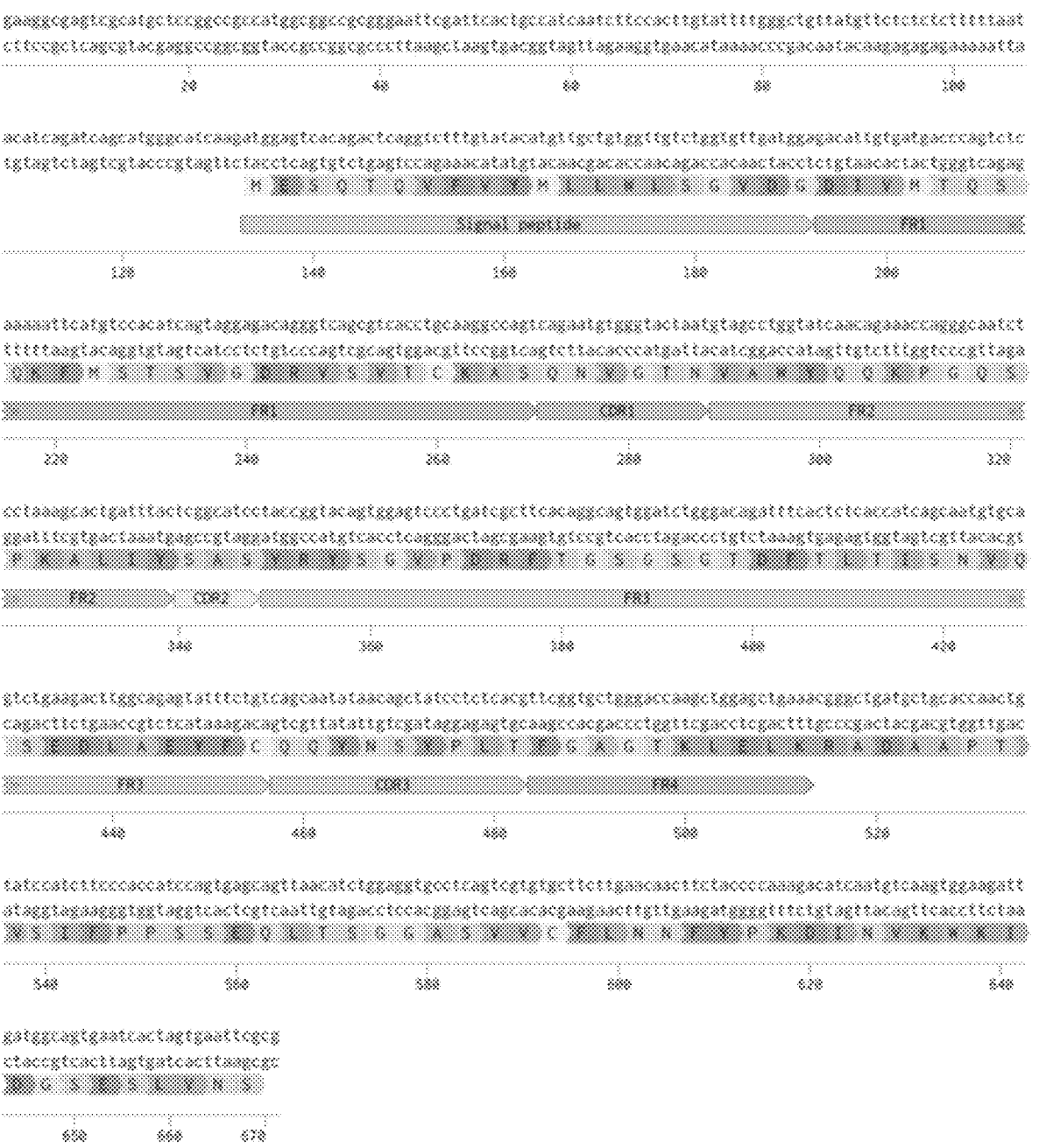
Figure 11F:
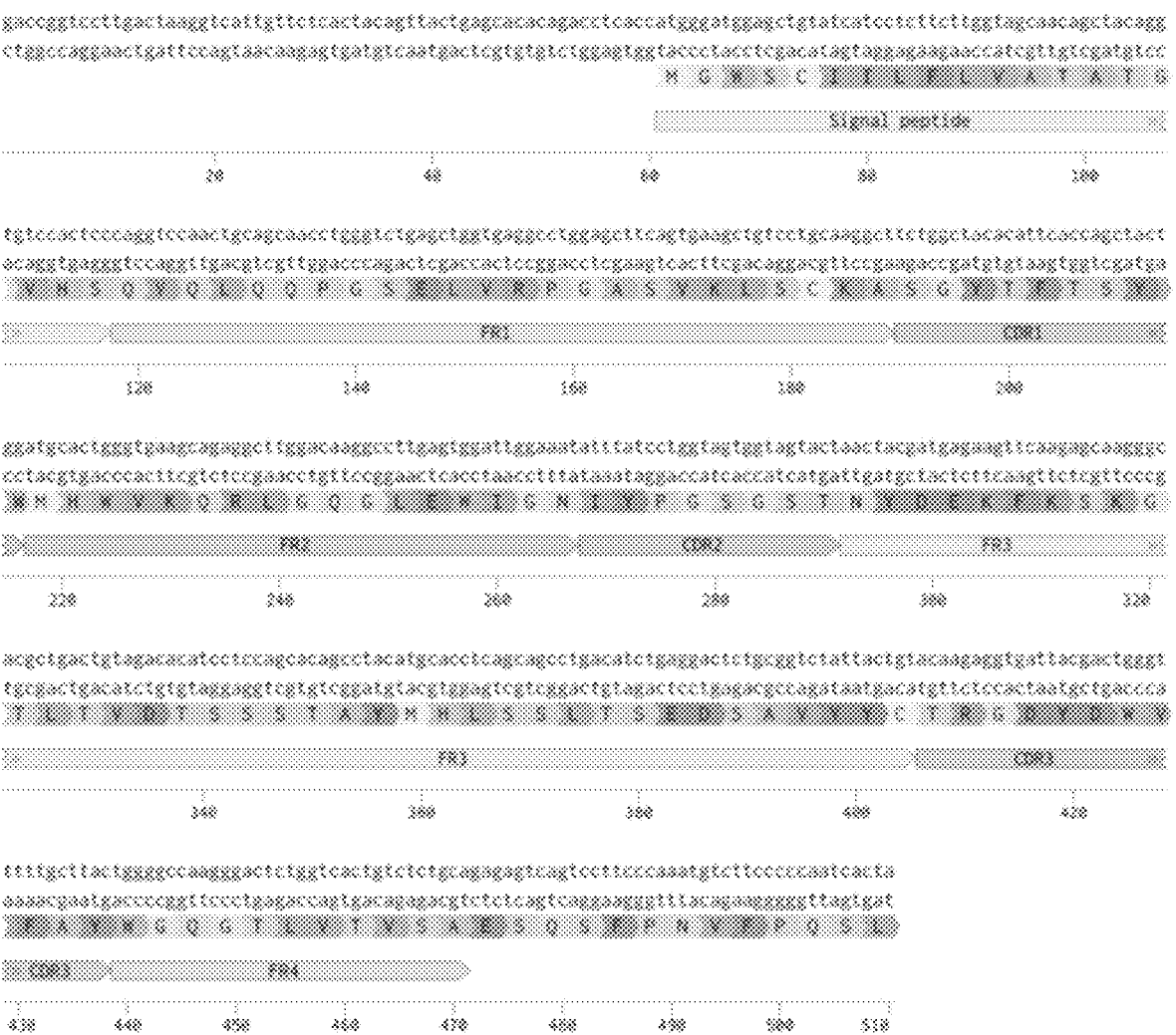

The expansion and persistence of CARTs in tumor bearing NSG mice were monitored (FIG. 8C-E). The data showed that between days 11-25 after transfer, the human T cells (FIG. 8D) and the percentage of the CAR+ T cells (FIG. 8E) significantly increased in the groups treated with 6G11 and 8F8 CARTs. The CAR+ T cells in the groups treated with 6G11 and 8F8 CART cells increased from 10-15%, prior to the inoculation, to 30-60%, 2 weeks after adoptive transfer (FIG. 8E). In contrast, the group treated with 12D7 CARTs showed no increase of adopted human T cells and the % of CAR+ T cells. The data suggests that 6G11 and 8F8 CARTs are activated and expanded when they meet HCC tumor cells in vivo, correlating to their effective antitumor effects and tumor regression.

Example X: CART Production Overview

1. Total RNA was isolated from monoclonal hybridoma cells. The cDNA was synthesized and amplified by PCR using 5' RACE technique. The PCR products were sequenced. The nucleotide sequences of the variable region of light chain (VL) and heavy chain (VH) of monoclonal antibodies (mAbs) 6G11, 8F8, and 12D7 were presented Table 1 and FIGS. 11A-11F. The amino acid sequences deduced from the cDNA were compared to IMGT databank. And the designated frame region (FR) and complementarity determining region (CDR) of each mAb were also presented (FIGS. 11A-11F).

TABLE 1

| | | |
|---|---|---|
| nucleotide sequences of the variable region of light chain (VL) and heavy chain (VH) of monoclonal antibodies (mAbs) 6G11, 8F8, and 12D7 | | |
| mAB | SEQ ID NOs: Respectively, in order of appearance | Corresponding Figure |
| 6G11-VL | 4 and 5 | FIG. 11A |
| 6G11-VH | 6 and 7 | FIG. 11B |
| 8F8-VL | 8 and 9 | FIG. 11C |
| 8F8-VH | 10 and 11 | FIG. 11D |
| 12D7-VL | 12 and 13 | FIG. 11E |
| 12D7-VH | 14 and 15 | FIG. 11F |

Figure 12A:
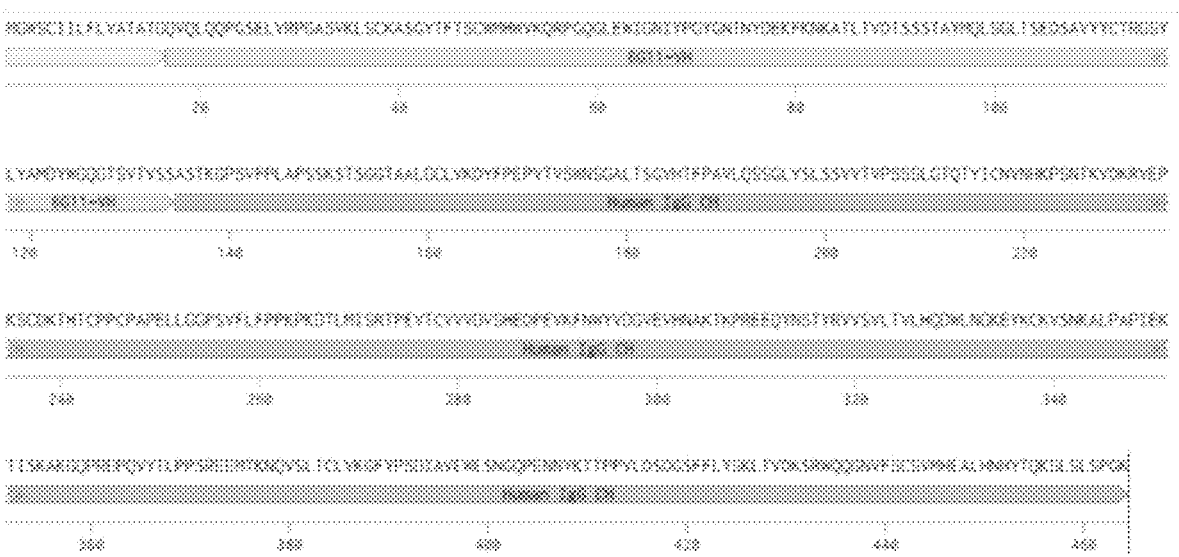
FIGS. 12A-12C show the recombinant mAb generated by fusing the human IgG leader sequences, the VL or VH sequences of each mAbs (6G11 (FIG. 12A), 8F8 (FIG. 12B), and 12D7 (FIG. 12C)), and the constant (C) region of human IgG.
Figure 12A:
Figure 12B:
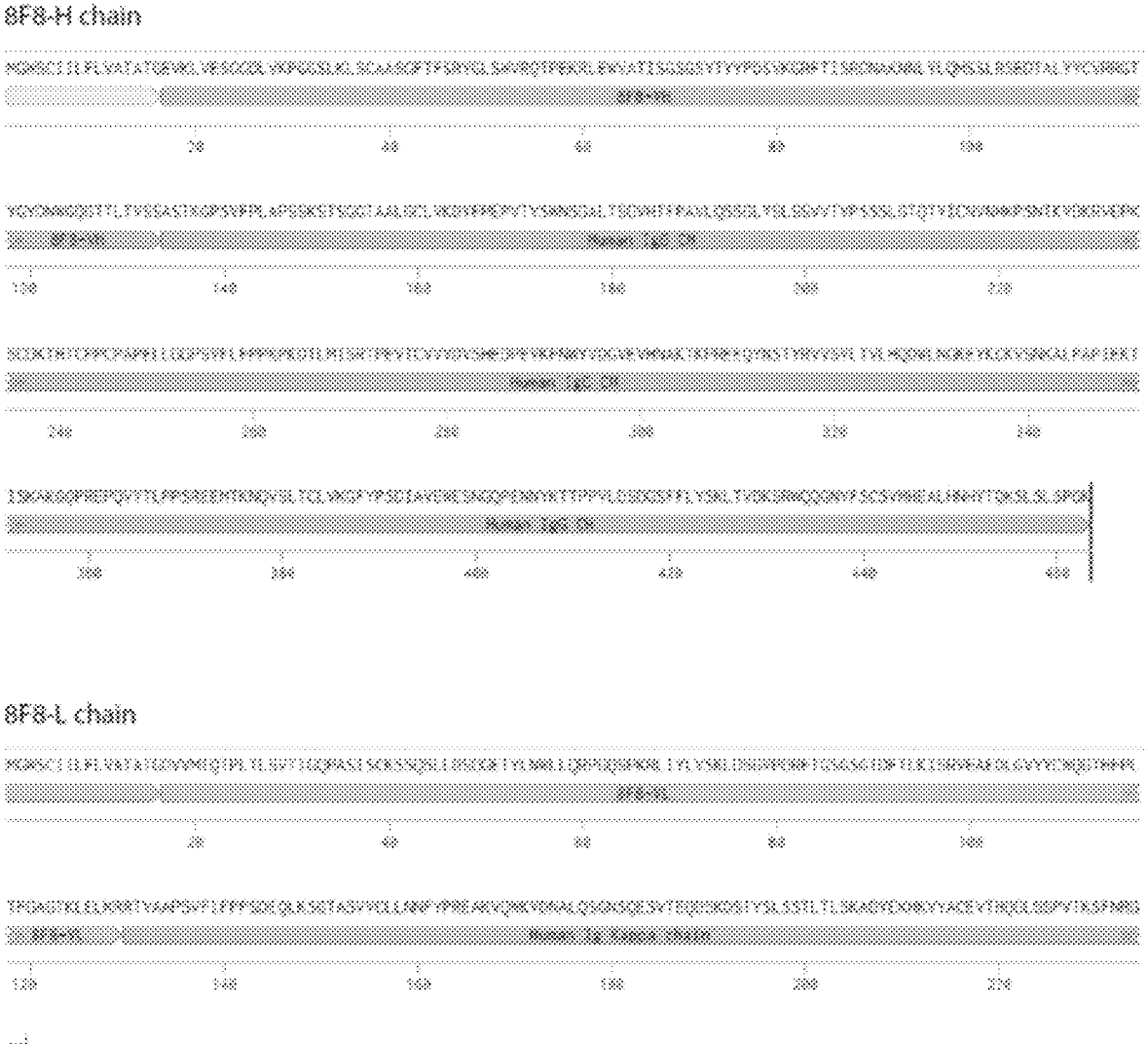
Figure 12C:
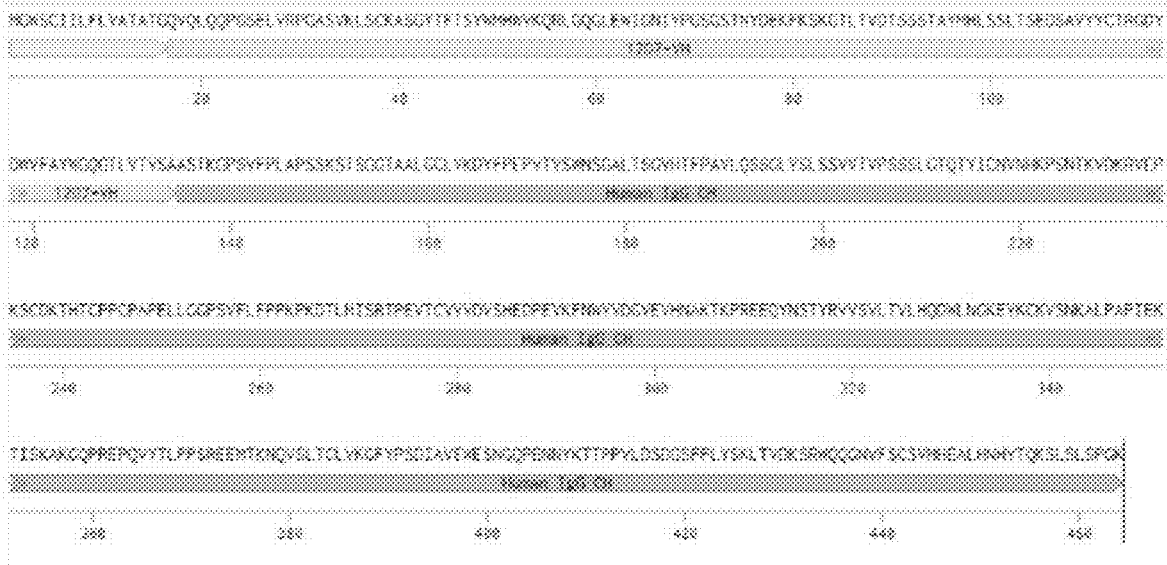
Figure 12C:
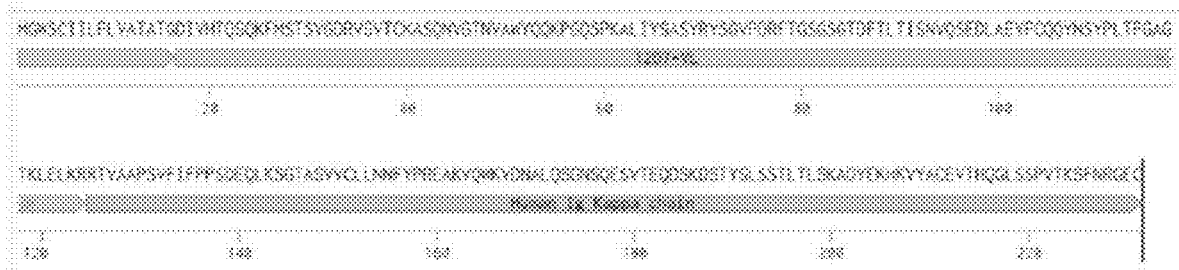

2. Next, we generated recombinant mAb by fusing the human IgG leader sequences, the VL or VH sequences of each mAbs (6G11, 8F8, and 12D7), and the constant (C) region of human IgG. The amino acid sequences of each recombinant H and L chain were presented Table 2 and FIGS. 12A-12C.

TABLE 2

| | | |
|---|---|---|
| Recombinant mAb of each mAb (6G11, 8F8, and 12D7) | | |
| Recombinant mAb | SEQ ID NOs: Respectively, in order of appearance | Corresponding Figure |
| 6G11 | 16 and 17 | FIG. 12A |
| 8F8 | 18 and 19 | FIG. 12B |
| 12D7 | 20 and 21 | FIG. 12C |

Figure 13A:
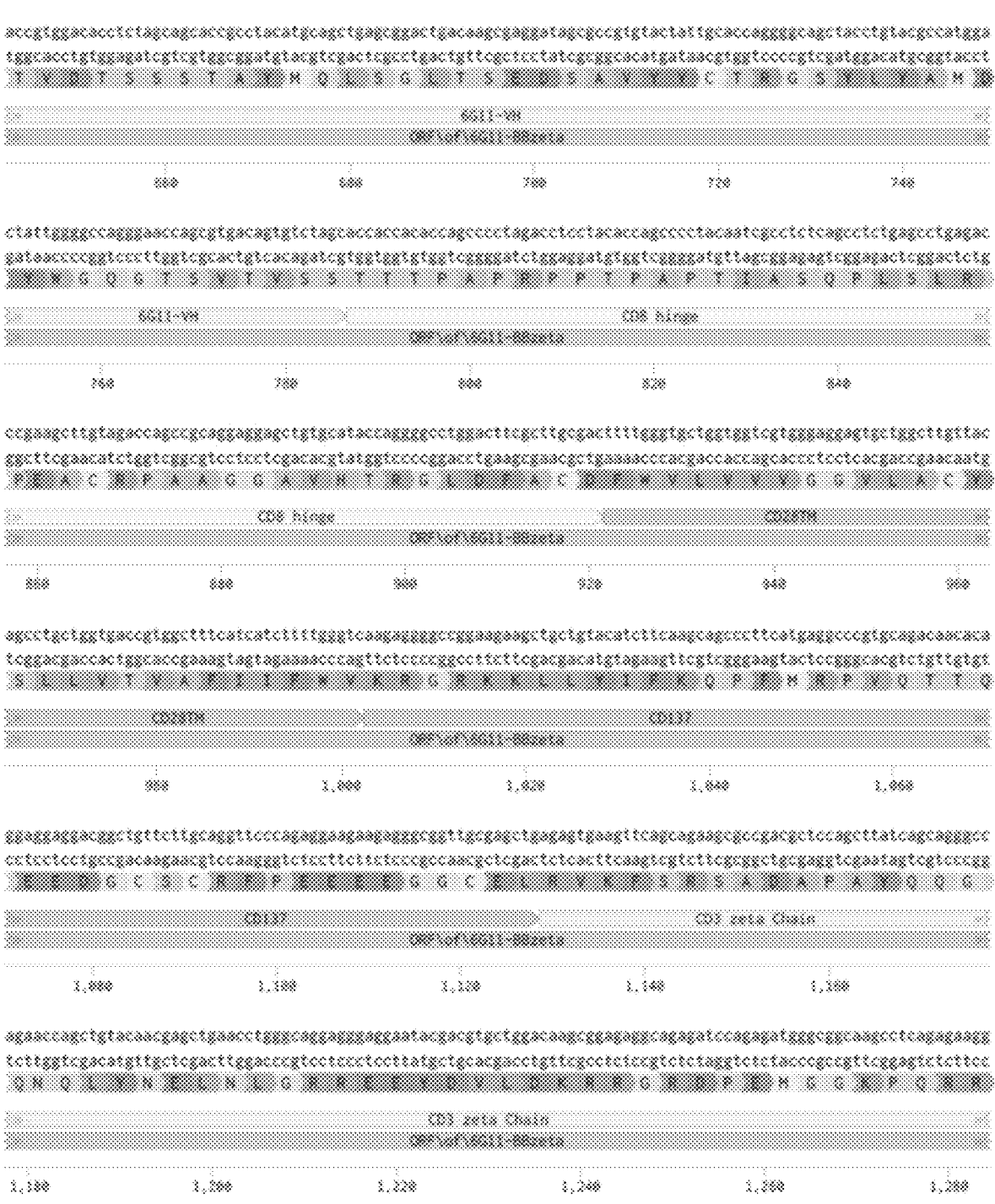
FIGS. 13A-13C show the second generation of CAR from the mAb 6G11 (FIG. 13A), 8F8 (FIG. 13B), and 12D7 (FIG. 13C) VL and VH sequences.
Figure 13A:
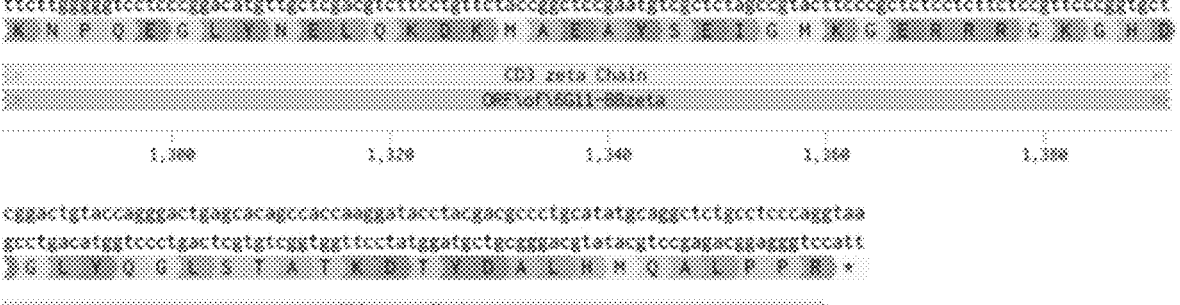
Figure 13B:
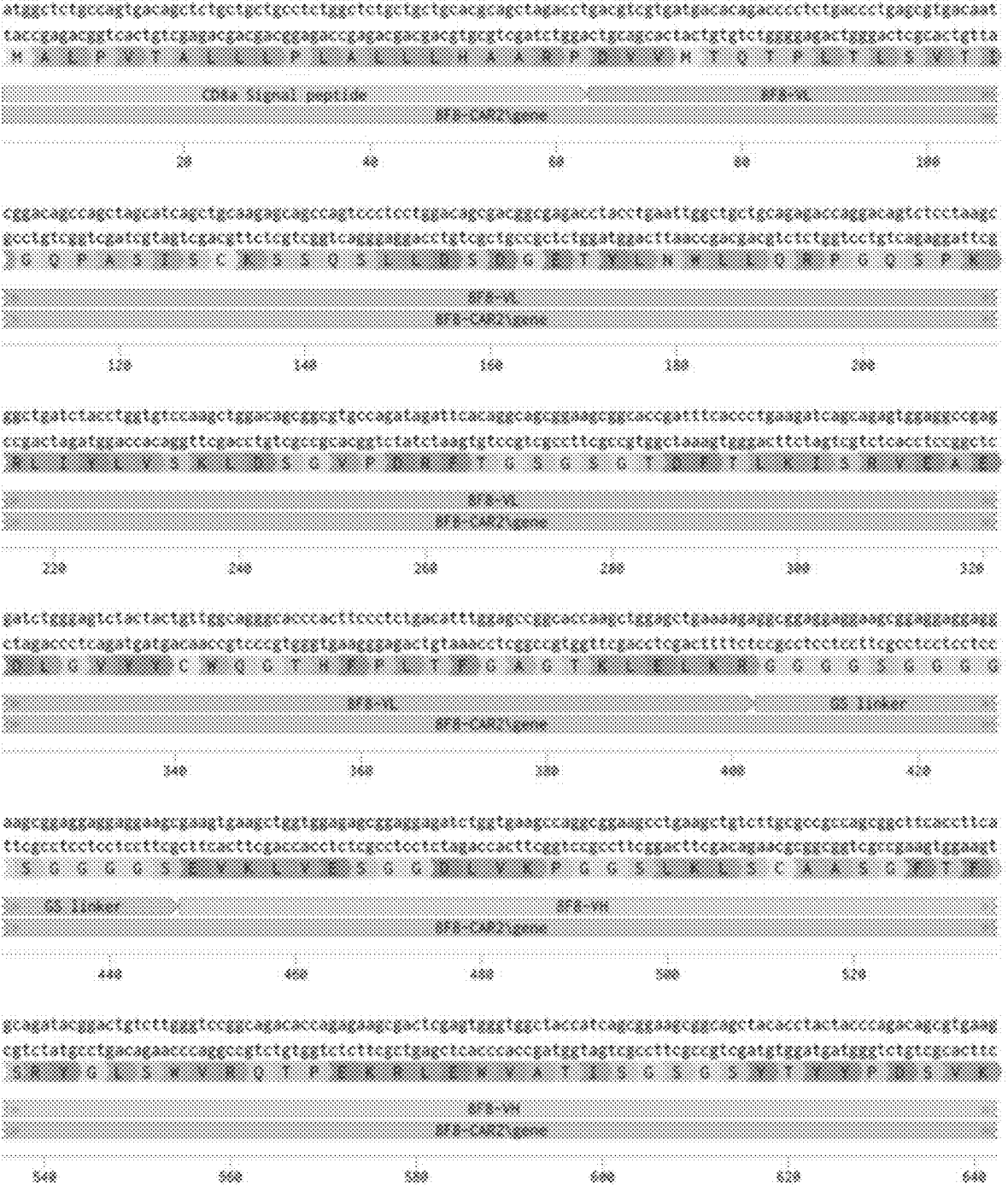
Figure 13B:
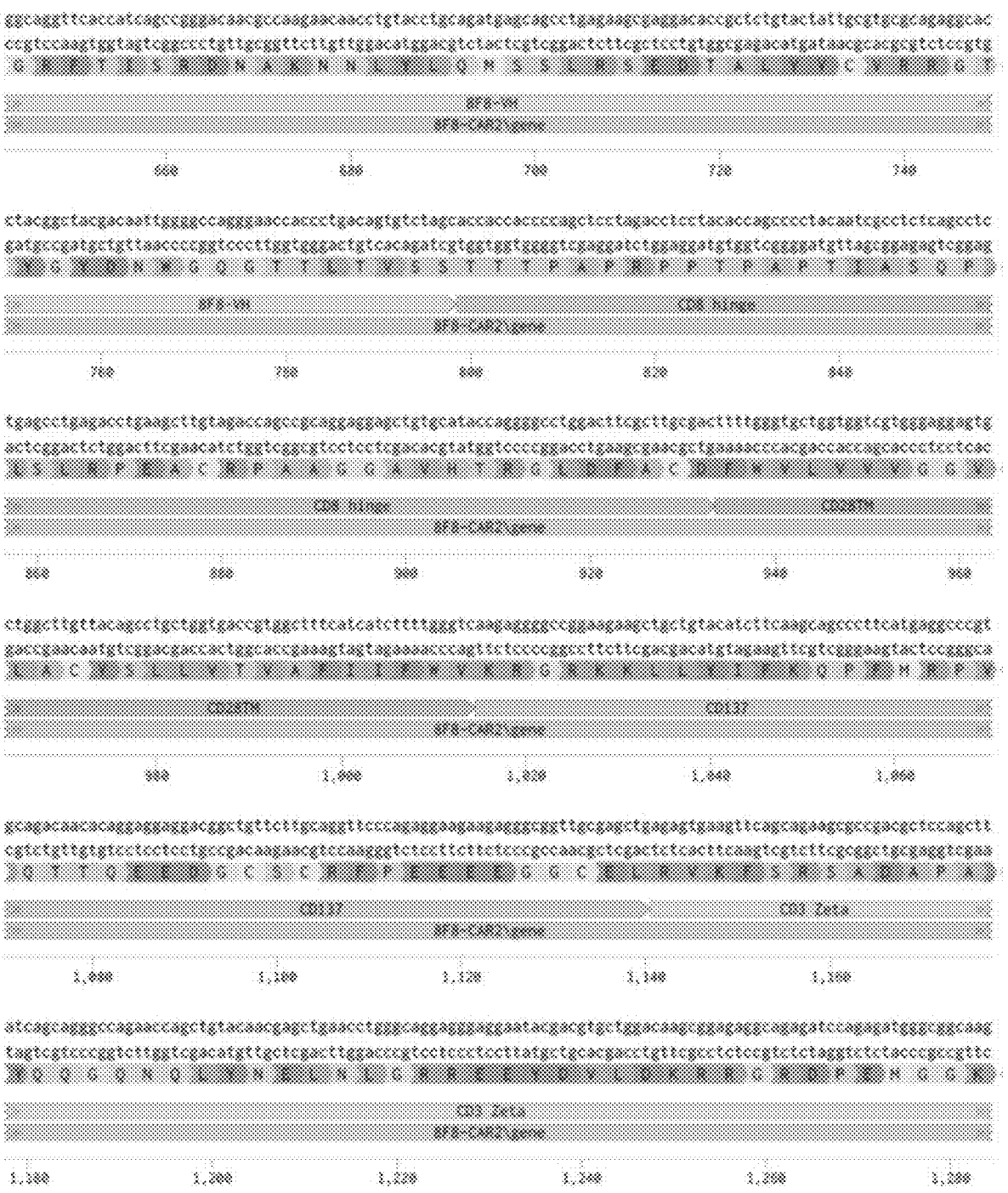
Figure 13B:
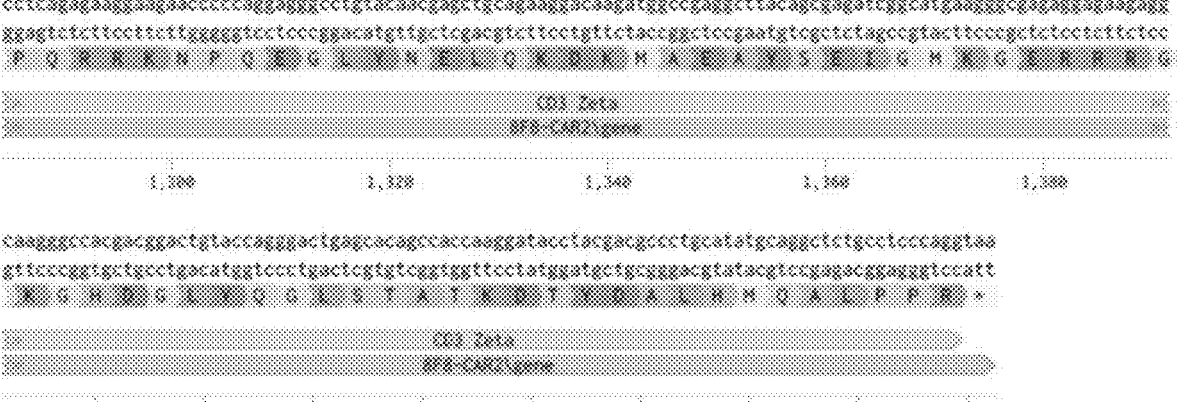
Figure 13C:
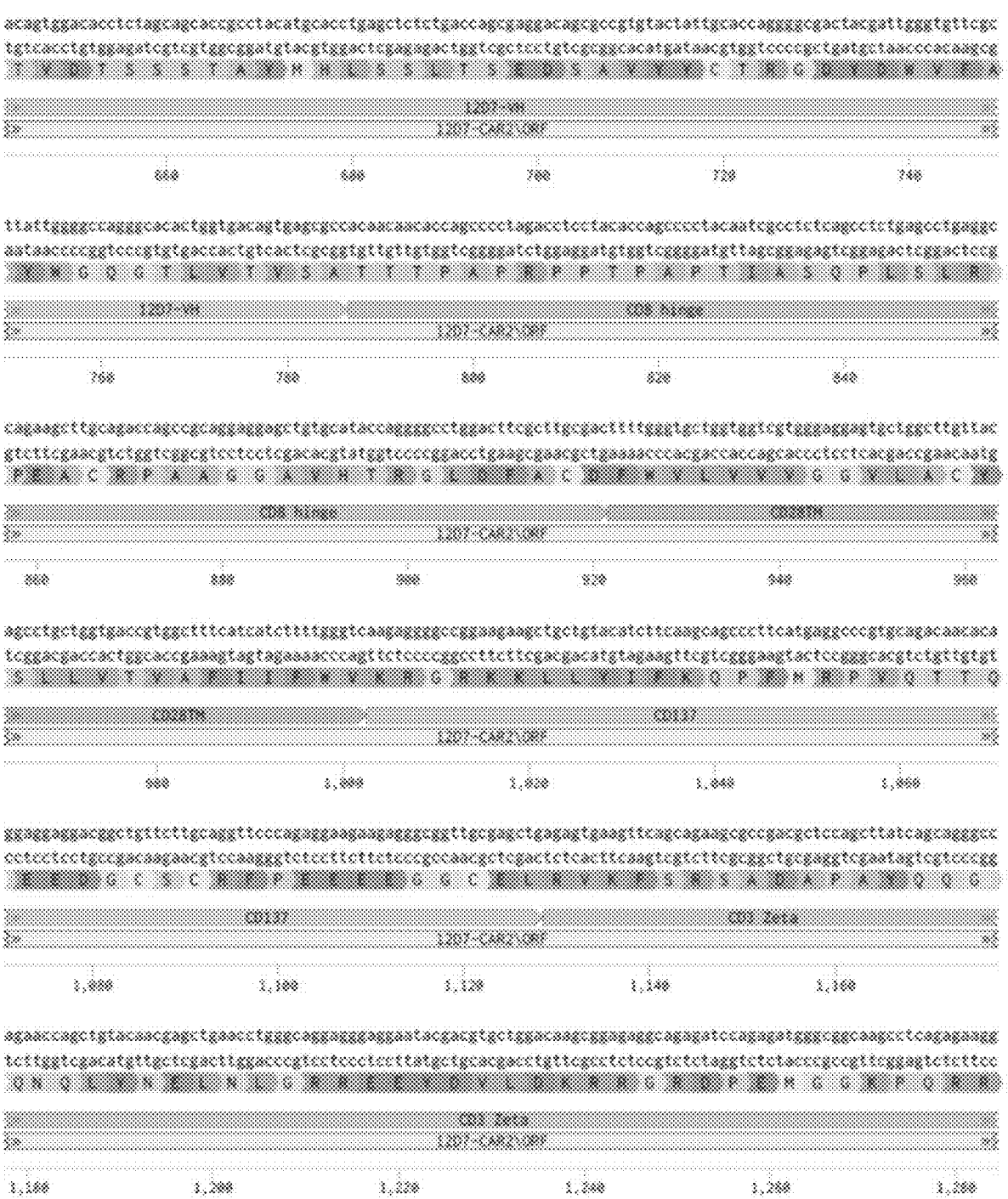
Figure 13C:
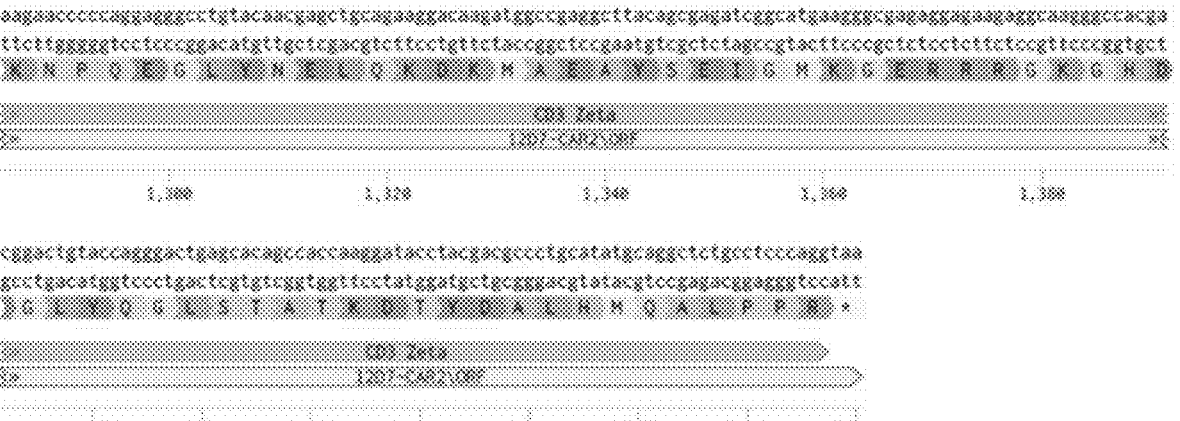

3. We next built the second generation of CAR from the mAb 6G11, 8F8, and 12D7 VL and VH sequences. Both the DNA and protein sequences of the 3 CARs were presented in Table 3 and FIGS. 13A-13C.

TABLE 3

| | | |
|---|---|---|
| Second generation CAR Sequences | | |
| 2nd Generation CAR Sequences | SEQ ID NOs: Respectively, in order of appearance | Corresponding Figure |
| 6G11-CAR | 1 and 22 | FIG. 13A |
| 8F8-CAR | 2 and 23 | FIG. 13B |
| 12D7-CAR | 3 and 24 | FIG. 13C |

DISCUSSION

The goal of the study was to develop novel effective CARTs for HCC immunotherapy by targeting different hGPC3 epitopes. To this end, 3 mAbs (6G11, 8F8, and 12D7) were generated that recognize the N-, C-, and a conformational epitope of hGPC3, respectively. These mAbs are highly specific and able to distinguish HCC tumors from the adjacent normal liver tissues. Then, CARTs were built from the mAbs, and it was found that all 3 CARTs could undergo expansion in response to HCC tumor cell stimulation. But, their effector functions were markedly different. The 8F8 CARTs generated the strongest cytotoxicity and the highest production of IFNγ after HCC tumor cell stimulation. Compared to 8F8 CARTs, the 6G11 CARTs underwent an even greater in vitro expansion, but with a slight weaker cytotoxicity and significant lower IFNγ and IL2 production. In contrast, the 12D7 CARTs showed the weakest cytotoxicity and produced the least amount of IFNγ and no IL2. Adoptive transfer of 6G11 and 8F8, but not 12D7, CARTs generated potent antitumor effects and resulted in complete eradication of HCC tumor xenografts in NSG mice, which correlated to their in vivo expansion.

Figures 5D, 5E:
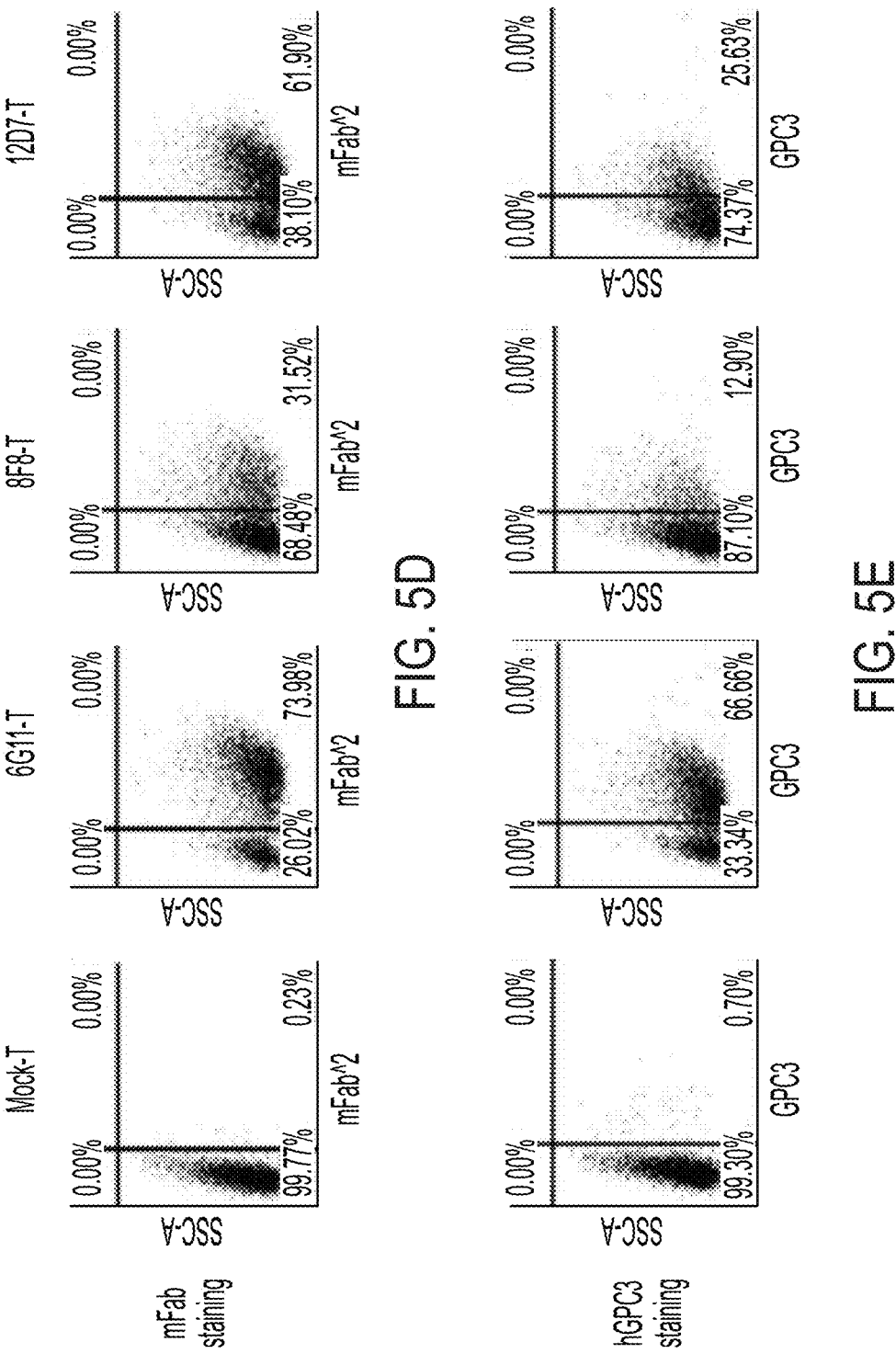
FIGS. 5D and 5E are dot plots showing CAR molecules on the transduced T cells were stained with anti-mouse Fab antibody (A) or FITC-labeled hGPC3. Mock transduced T cells were used as control.
Figure 5F:
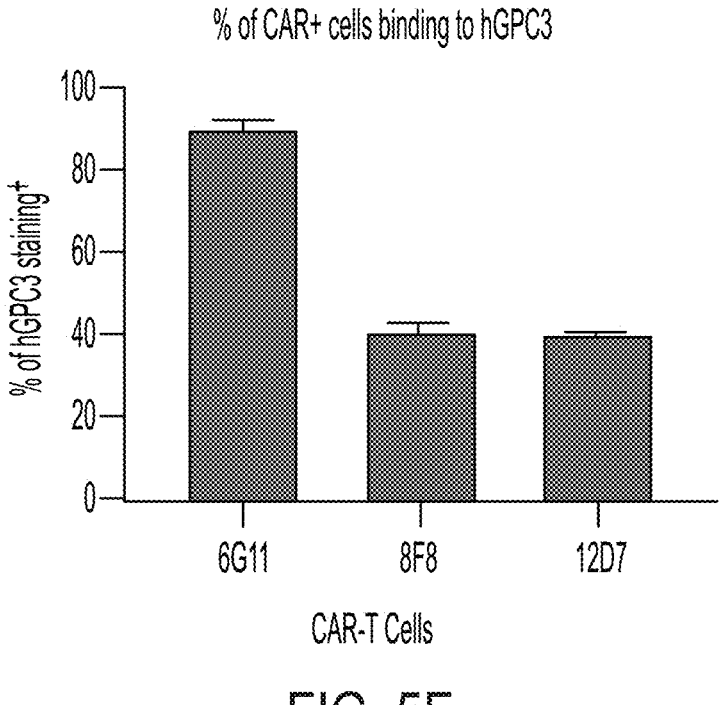
FIG. 5F is a graph showing the percent of CAR+ T cells that could bind hGPC3 protein.

Several factors may contribute to the different effector functions of the CARTs. The first reason could be the epitope location in the target antigen. Previous reports showed that the position of the epitope within the target molecule determined the efficiency of CART activation (38, 39). The membrane-proximal epitopes may facilitate efficient immunological synapse between targets and CARTs (40). This explanation fits well with 8F8 CARTs, which bind the membrane-proximal C-epitope (AA463-496) of hGPC3 and possess the strongest cytotoxicity and produces the highest amount of cytokines. However, the 6G11 CARTs recognize an epitope at the beginning of the N-terminus (AA25-39) that is conceivably membrane-distal. Nevertheless, it undergoes stronger expansion after HCC tumor stimulation and possesses potent effector function, albeit it is slightly weaker than 8F8 CARTs. These data suggest that the engagement of CARTs with hGPC3 N-terminal epitopes is also sufficient to initiate CART activation and effector function. One reason that may explain why 6G11 CARTs, targeting the membrane-distal epitope also generate potent effector function and antitumor effect, is its accessibility to target antigen. In fact, our data showed that 90% of 6G11 CAR+ T cells could bind hGPC3, while only about 40% of 8F8 CAR+ and 12D7 CAR+ T cells were able to bind hGPC3, suggesting that 6G11 CAR on T cells and 6G11' epitope on hGPC3 are more accessible to each other (FIGS. 5D-F). Thus, more CAR and hGPC3 engagement might generate stronger signaling to activate CARTs even though the target epitope may not be in membrane-proximity. Another factor that may affect CART's function is the mAb's affinity (41). According to the data from two measurements (BLI and ELISA), the affinity order of the 3 mAbs is 6G11>12D7>8F8. The high affinity of 6G11 for hGPC3 may also help generate stronger interaction of CARTs and tumor cells even if the epitope is membrane-distal. Thirdly, hGPC3 N-fragment is linked to the C-fragment by disulfide bonds (25, 42, 43), which may bring the N-terminal epitope closer to cell membrane than expected to generate stronger interaction between CARTs and tumor cells. However, as recent studies (44, 45) demonstrated that strong T cell signaling may lead to premature exhaustion, it will be interesting to determine the signaling strength of these CARTs and its relevancy to the epitope position and effector functions.

Different from 6G11 and 8F8 that recognize specific region of hGPC3, the 12D7 CARTs recognize a conformational epitope on the hGPC3 N-fragment and have the lowest effector function. These data are in agreement with a recent report showing that the HN3 CARTs targeting a conformational epitope of GPC3 did not generate antitumor efficacy even though no detailed analysis was provided in the meeting abstract (46). In the study, the 12D7 CARTs underwent expansion as good as 8F8 CARTs in response to HepG2 cell stimulation (FIG. 6A-B), but they did not produce effector cytokines, and had weak cytotoxicity (FIG. 6C-D). It is likely that the engagement of 12D7 CARTs with the hGPC3 conformational epitope generates sufficient signaling to drive CART proliferation, but not enough to fully activate CARTs to have effector functions. The lack of cytokine production, especially IL-2, may explain the incapability of 12D7 CARTs to expand in vivo (FIGS. 8E and 8F), which correlates to their weaker in vivo antitumor effects.

Even though the 8F8 mAb has the lowest affinity for hGPC3, the 8F8 CARTs generated the strongest cytotoxicity and produced the highest amount of cytokines after HepG2 tumor cell stimulation. On the other hand, the 6G11 and 12D7 mAbs have a similar affinity, but their effector functions are dramatically different (FIG. 6). Furthermore, soluble hGPC3 does not activate CARTs nor block the CART activation by tumor cells (FIG. 7). Together, these data suggest that several parameter might affect CART activation, and that immunological synapse may play a dominant role in the CART's effector function (40, 47).

Most of the current and previous studies are mainly focused on the signaling transduction domains, including the $1^{st}$ to $3^{rd}$ generations of CARs, to improve CAR-T's efficacy (48). The role of antibody domains in the generation of potent CARTs has been less investigated. The 3 new CARTs, targeting different regions of hGPC3, and having different affinities, not only offer more arsenal for HCC immunotherapy, but also provide us materials and opportunities to extend the study of the mechanism of CARTs and target tumor cells interaction. Future studies are required to analyze the subsets of each CART and to investigate the immunological synapse and the signaling strength they generate. These different CARTs properties may help us reveal the mechanisms behind the relation between of CART expansion, activation and effector functions, and enable us to further improve their antitumor efficacy.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

We claim:

1. A chimeric antigen receptor comprising an extracellular domain comprising an antigen binding domain that immunospecifically binds to Glypican 3 (GPC3), the antigen binding domain comprising a light chain variable region comprising the three complementarity determining regions (CDRs) of SEQ ID NO:9 and heavy chain variable region comprising the three CDRs of SEQ ID NO:11.

2. The chimeric antigen receptor of claim 1, wherein the chimeric antigen receptor further comprises a transmembrane domain and an intracellular domain.

3. The chimeric antigen receptor of claim 2, wherein the transmembrane domain comprises the transmembrane domain of CD28.

4. The chimeric antigen receptor of claim 2, wherein the intracellular domain comprises an activation domain.

5. The chimeric antigen receptor of claim 2, wherein the intracellular domain comprises a costimulatory domain.

6. The chimeric antigen receptor of claim 2, wherein the intracellular domain comprises an activation domain and a costimulatory domain.

7. The chimeric antigen receptor of claim 5, wherein the intracellular domain comprises one or more activation and/or costimulatory domains from CD28, CD137, CD35, 4-1BBL, OX40L, CD70, LIGHT, and CD30L, or an Ig superfamily ligand optionally CD80 and CD86, and combinations thereof.

8. The chimeric antigen receptor of claim 7, comprising 4-1BB and CD32 chain signaling domains.

9. The chimeric antigen receptor of claim 1, wherein the extracellular domain further comprises a hinge domain.

10. The chimeric antigen receptor of claim 9, wherein the hinge domain comprises a hinge domain from CD8.

11. The chimeric antigen receptor of claim 1, wherein antigen binding domain is a single chain antibody (scFv).

12. The chimeric antigen receptor of claim 1, wherein the antigen binding domain comprises the light chain variable region of SEQ ID NO:9 or a humanized form thereof and the heavy chain variable region of SEQ ID NO:11 or a humanized form thereof.

13. The chimeric antigen receptor of claim 12, wherein the antigen binding domain is a single chain antibody (scFv).

14. A chimeric antigen receptor comprising an extracellular domain comprising an antigen binding domain that immunospecifically binds to Glypican 3 (GPC3) linked to a hinge domain linked to transmembrane domain linked to an intracellular domain, wherein the antigen binding domain comprises a light chain variable domain comprising the three complementarity determining regions (CDRs) of SEQ ID NO:9 and heavy chain variable domain comprising the three CDRs of SEQ ID NO:11, the hinge domain comprises a hinge domain from CD8, the transmembrane domain comprises the transmembrane domain of CD28, and the intracellular domain comprises 4-1BB and CD3ζ chain signaling domains.

15. The chimeric antigen receptor of claim 14 comprising the amino acid sequence of (i) SEQ ID NO:23 or (ii) SEQ ID NO:23 wherein the antigen binding domain is humanized.

16. A nucleic acid encoding the chimeric antigen receptor of claim 1.

17. A lentiviral vector comprising the nucleic acid of claim 16.

18. An immune cell expressing the chimeric antigen receptor of claim 1, optionally wherein the cell is a T cell or Natural Killer (NK) cell.

19. A method of treating liver cancer comprising administrating to a subject in need thereof an effective amount of the cells of claim 18.

20. The method of claim 19, wherein the liver cancer is hepatocellular carcinoma.

\* \* \* \* \*